US010822409B2

(12) United States Patent
Kim et al.

(10) Patent No.: US 10,822,409 B2
(45) Date of Patent: Nov. 3, 2020

(54) COMPOSITIONS AND METHODS FOR MEASURING NMU AND FOR TREATMENT USING ANTI-NMU AGENTS

(71) Applicant: The Board of Trustees of the Leland Stanford Junior University, Stanford, CA (US)

(72) Inventors: Seung K. Kim, Stanford, CA (US); Sangbin Park, Stanford, CA (US); Ronald Alfa, Salt Lake City, UT (US); Cecile Jacovetti, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/294,668

(22) Filed: Mar. 6, 2019

(65) Prior Publication Data
US 2019/0218286 A1   Jul. 18, 2019

Related U.S. Application Data

(62) Division of application No. 15/418,550, filed on Jan. 27, 2017, now Pat. No. 10,294,297.

(60) Provisional application No. 62/288,985, filed on Jan. 29, 2016.

(51) Int. Cl.
*C07K 16/26* (2006.01)
*G01N 33/74* (2006.01)
*G01N 33/68* (2006.01)
*G01N 33/564* (2006.01)

(52) U.S. Cl.
CPC .......... *C07K 16/26* (2013.01); *G01N 33/564* (2013.01); *G01N 33/6893* (2013.01); *G01N 33/74* (2013.01); *C07K 2317/51* (2013.01); *C07K 2317/515* (2013.01); *C07K 2317/76* (2013.01); *C07K 2317/92* (2013.01); *G01N 2333/575* (2013.01); *G01N 2800/042* (2013.01); *G01N 2800/067* (2013.01); *G01N 2800/50* (2013.01)

(58) Field of Classification Search
CPC ................................ C07K 16/26; G01N 33/74
See application file for complete search history.

(56) References Cited

U.S. PATENT DOCUMENTS

2014/0206574 A1   7/2014   Chapman et al.

FOREIGN PATENT DOCUMENTS

WO   2014118634 A1   8/2014

OTHER PUBLICATIONS

Chamov and Ashkanazi, TIBTECH 14: 52-60, (1996).*
Rudikoff et al., Proc. Natl. Acad. Sci. 79: 1979-1983, (1982).*
Alfa et al., "Suppression of insulin production and secretion by a decretin hormone", Cell Metabolism, Feb. 3, 2015, pp. 323-333, vol. 21, Issue 2, Elsevier, Amsterdam, Netherlands.
Arda et al., "Age-dependent pancreatic gene regulation reveals mechanisms governing human β cell function", Cell Metabolism, May 10, 2016, pp. 909-920, vol. 23, Issue 5, Elsevier, Amsterdam, Netherlands.
Blodgett et al.,"Islet β-Cell Transcriptome and Integrated-omics", Curr Opin Endocrinol Diabetes Obes., Apr. 2014, pp. 83-88, 21(2), Wolters Kluwer Health, Inc. Philadelphia, PA.
Campbell et al., "Pharmacology, physiology, and mechanisms of incretin hormone action", Cell Metabolism, Jun. 4, 2013, pp. 819-837, vol. 17, Issue 6, Elsevier, Amsterdam, Netherlands.
Kaczmarek et al., "Neuromedin U receptor 1 expression in the rat endocrine pancreas and evidence suggesting neuromedin U suppressive effect on insulin secretion from isolated rat pancreatic islets", Int J Mol Med., Nov. 2006, pp. 951-955, 18(5), Spandidos Publications, London, United Kingdom.
Kaczmarek et al., "Does Somatostatin Confer Insulinostatic Effects of Neuromedin U in the Rat Pancreas?", Pancreas, Mar. 2009, pp. 208-212, vol. 38, No. 2, Lippincott Williams & Wilkins, Philadelphia, PA.
Van Der Meulen et al., "Urocortin3 mediates somatostatin-dependent negative feedback control of insulin secretion", Nat Med., Jul. 2015, pp. 769-776, 21(7) , Macmillan Publishers Limited, London, United Kingdom.
Van Der Meulen et al., "The role of transcription factors in the transdifferentiation of pancreatic islet cells", J Mol Endocrinol., Apr. 2015, pp. R103-R117, 54(2), Society for Endocrinology, Washington, DC.

(Continued)

*Primary Examiner* — Gyan Chandra
(74) *Attorney, Agent, or Firm* — Kyle A. Gurley; Bozicevic, Field & Francis LLP

(57) ABSTRACT

The inventors have produced two high specificity and high affinity monoclonal antibodies that bind to human neuromedin U (NMU). Methods and compositions are provided for treating an individual in need thereof (e.g., an individual who is obese and/or has diabetes) by administering an anti-NMU/NMUR agent (e.g., an anti-NMU antibody). For example, methods and compositions are provided for increasing circulating insulin in an individual. Methods and compositions are also provided for detecting neuromedin U (NMU) (e.g., in a biological sample such as serum). Methods and compositions are also provided for predicting whether an individual will develop diabetes and/or PDAC, and for identifying an individual who would benefit from administration of an anti-NMU/NMUR agent.

15 Claims, 31 Drawing Sheets
(20 of 31 Drawing Sheet(s) Filed in Color)
Specification includes a Sequence Listing.

(56) References Cited

OTHER PUBLICATIONS

Ketterer et al., "Neuromedin U is overexpressed in pancreatic cancer and increases invasiveness via the hepatocyte growth factor c-Met pathway", Cancer Lett., May 8, 2009, pp. 72-81, 277(1), Elsevier, Amsterdam, Netherlands.
Product manual for ELISA Kit for Neuromedin U (NMU) (stated revision date: Jul. 2013), pp. 1-8.
Sandwich ELISA, Protocols from abcam® website (available as of at least Aug. 24, 2014), pp. 1-2.
Chamow and Ashkenazi, Tibtech, Immunoadhesins: principles and applications, vol. 14, Feb. 1996, pp. 52-60.
Rudikoff, et al., Single Amino Acid Substitution Altering Antigen-Binding Specificity, Proc. Natl. Acad. Sci., vol. 79, Mar. 1982, pp. 1979-1983.

\* cited by examiner

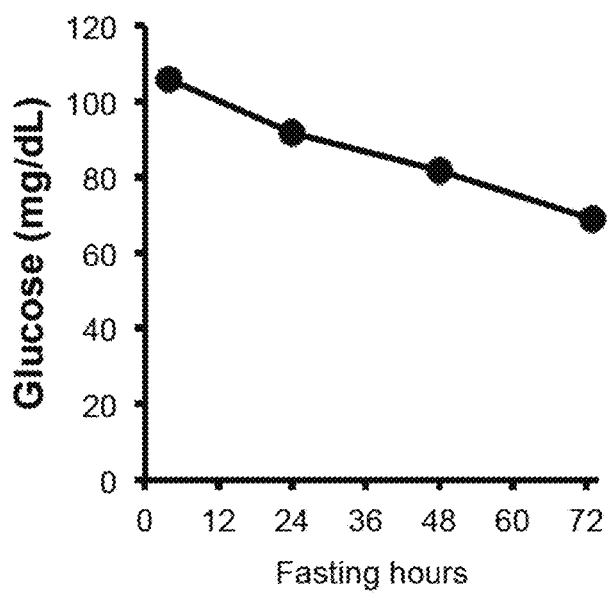
Fig. 1A Glucose
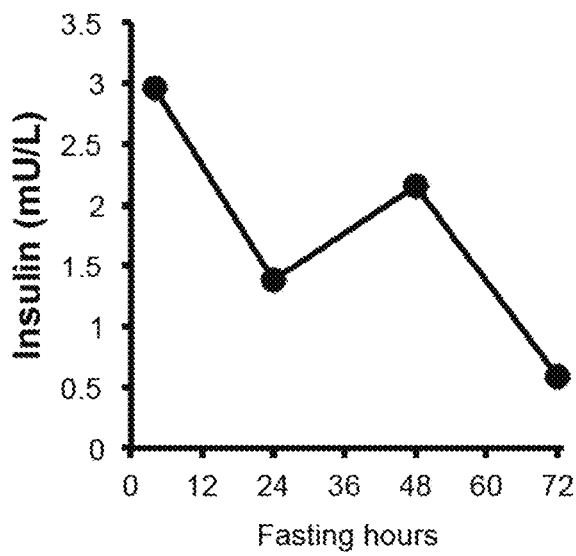
Fig. 1B Insulin
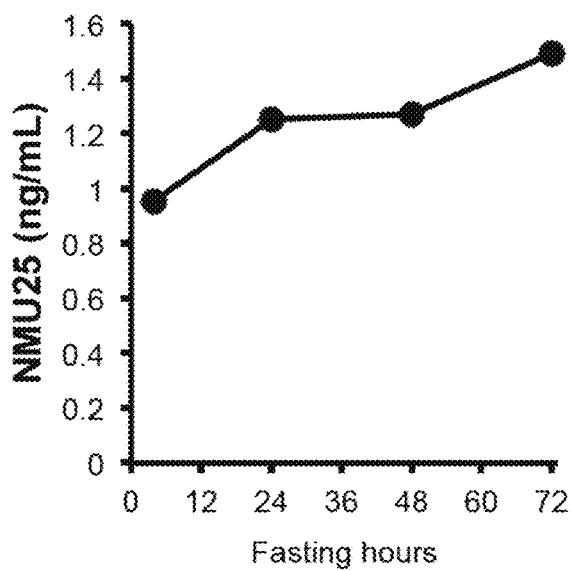
Fig. 1C NMU

* Significantly different from 3h fasting

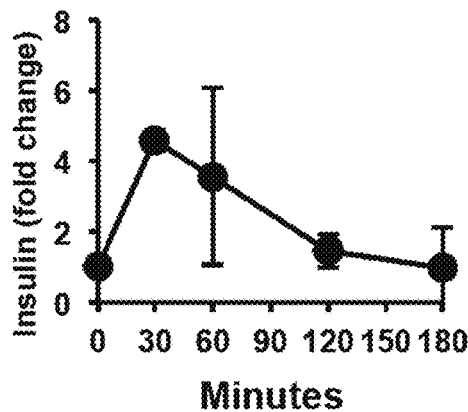
Fig. 2A Insulin
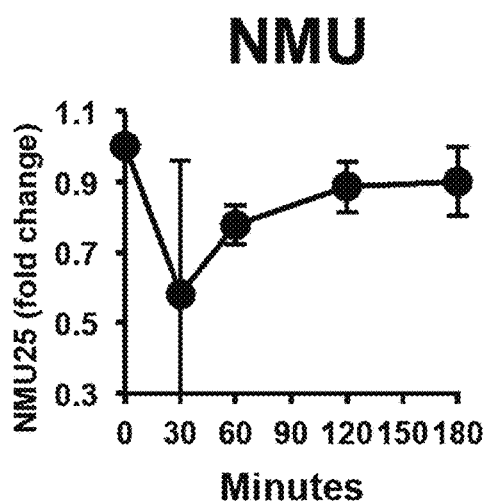
Fig. 2B NMU
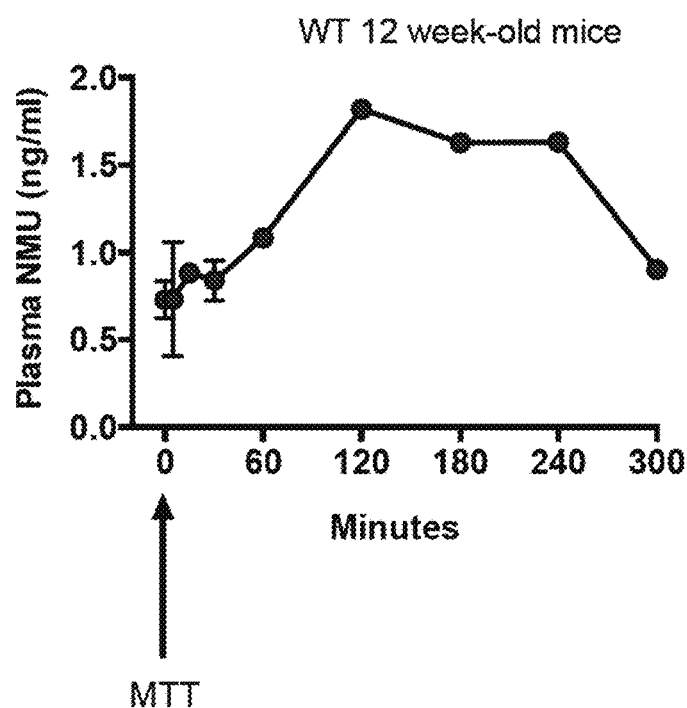
Fig. 2C WT 12 week-old mice
MTT

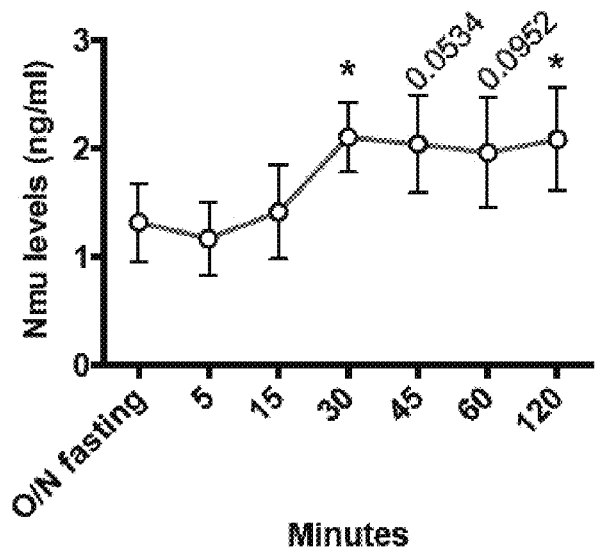
Fig. 2D NMU excursion-OGTT
* Significantly different from O/N fasting condition
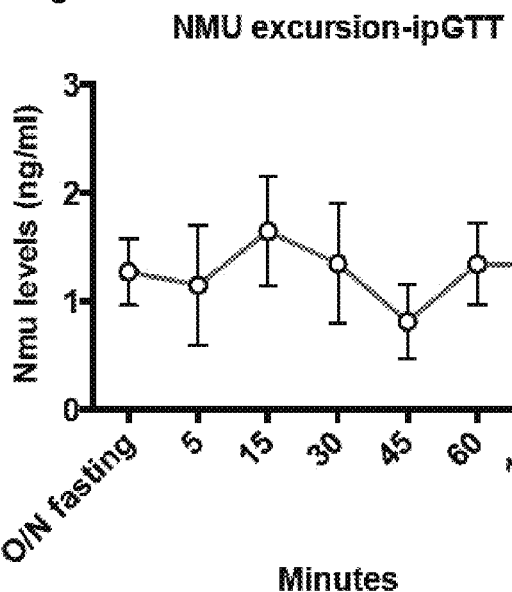
Fig. 2E NMU excursion-ipGTT
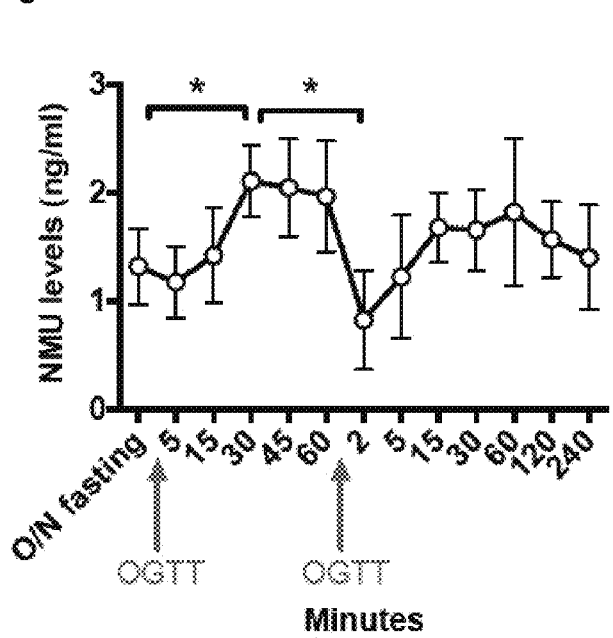
Fig. 2F ● Chow diet
□ HFD

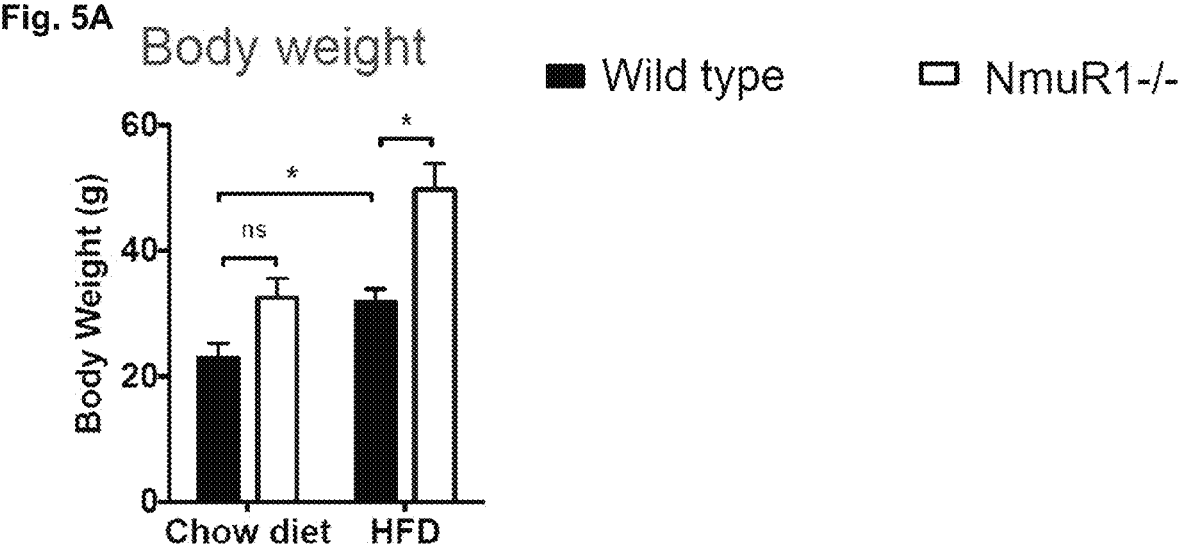
Fig. 5A Body weight
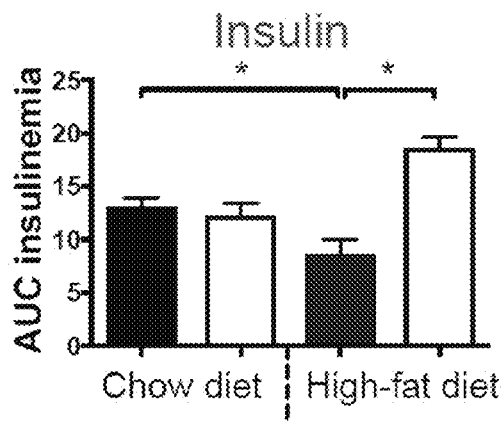
Fig. 5B Insulin
Oral glucose challenge
Fig. 5C Glucose
Oral glucose challenge

Fig.10

Antibody C578 (anti-NMU, recognizes mouse and human NMU)
Bioactive human NMU peptide:
    FRVDEEFQSPFASQSRGYFLFRPRN-NH$_2$  (SEQ ID NO:33)

C578 recognizes QSRGYFLFRPRN (SEQ ID NO: 34) (underlined above)

Antibody C578 Light Chain
(FR1 - CDR1 - FR2 - CDR2 - FR3 - CDR3 - FR4)

MESQTQVLMFLLLWVSGACANIVMTQSPSSLAMSIGQKVTMSCRSSQSLLNSSNQKNYLA**WYQQK
PGQSPKLLVYFASTRESGVPARFIGSGSGTDFTLTISSVQAEDLADYFCQQHYSTPFTFGSGTKL
EIK**  (SEQ ID NO: 1)

NIVMTQSPSSLAMSIGQKVTMSCRSSQSLLNSSNQKNYLAWYQQKPGQSPKLLVYFASTRES**GVP
ARFIGSGSGTDFTLTISSVQAEDLADYFCQQHYSTPFTFGSGTKLEIK**  (SEQ ID NO: 36)

```
CDR1(CDR-L1): RSSQSLLNSSNQKNYLA          (SEQ ID NO: 2)
CDR2(CDR-L2): FASTRES                    (SEQ ID NO: 3)
CDR3(CDR-L3): QQHYSTPFT                  (SEQ ID NO: 4)

FR1: NIVMTQSPSSLAMSIGQKVTMSC             (SEQ ID NO: 5)
FR2: WYQQKPGQSPKLLVY                     (SEQ ID NO: 6)
FR3: GVPARFIGSGSGTDFTLTISSVQAEDLADYFC    (SEQ ID NO: 7)
FR4: FGSGTKLEIK                          (SEQ ID NO: 8)
```

Antibody C578 Heavy Chain
(FR1 - CDR1 - FR2 - CDR2 - FR3 - CDR3 - FR4)

MKCSWVIFFLMAVVIGINSEVQLQQSGAELVRSGASVKLSCAASGFNIKDYYIH**WVKQRPEQGLE
WIGWIDPENGDNECAPKFQGKATMTADTSSNTAYLQLTSLTSEDTAVYYCNAGKGDYWGQGTTLT
VSS**  (SEQ ID NO: 9)

EVQLQQSGAELVRSGASVKLSCAASGFNIKDYYIHWVKQRPEQGLEWIGWIDPENGDNECAPKFQ
GKATMTADTSSNTAYLQLTSLTSEDTAVYYCNAGKGDYWGQGTTLTVSS  (SEQ ID NO: 37)

```
CDR1(CDR-H1): DYYIH                        (SEQ ID NO: 10)
CDR2(CDR-H2): WIDPENGDNECAPKFQG            (SEQ ID NO: 11)
CDR3(CDR-H3): GKGDY                        (SEQ ID NO: 12)

FR1: EVQLQQSGAELVRSGASVKLSCAASGFNIK       (SEQ ID NO: 13)
FR2: WVKQRPEQGLEWIG                        (SEQ ID NO: 14)
FR3: KATMTADTSSNTAYLQLTSLTSEDTAVYYCNA     (SEQ ID NO: 15)
FR4: WGQGTTLTVSS                           (SEQ ID NO: 16)
```

Fig.10 (Cont.)

Antibody 2A16 (anti-NMU, recognizes human NMU)
Bioactive human NMU peptide:
    <u>FRVDEEFQSPFAS</u>QSRGYFLFRPRN-NH$_2$    (SEQ ID NO:33)

2A16 recognizes FRVDEEFQSPFAS (SEQ ID NO: 35) (underlined above)

Antibody 2A16 Light Chain
(FR1 - <u>CDR1</u> - FR2 - <u>CDR2</u> - FR3 - <u>CDR3</u> - FR4)

MDMRAPAQIFGFLLLLFPGTRCDIQMTQSPSSLSASLGERVSLTC<u>RASQDIGSNLN</u>**WIQQEPDGT
IKRLIY<u>ATSTLDS</u>GVPKRFSGSRSGSDYFLTISSLESEDFVDYYC<u>LQFDSSPLT</u>FGAGTKLELK**
(SEQ ID NO: 17)

DIQMTQSPSSLSASLGERVSLTC<u>RASQDIGSNLN</u>WIQQEPDGTIKRLIY<u>ATSTLDS</u>**GVPKRFSGS
RSGSDYFLTISSLESEDFVDYYC<u>LQFDSSPLT</u>FGAGTKLELK** (SEQ ID NO: 38)

| | | |
|---|---|---|
| CDR1(CDR-L1): RASQDIGSNLN | (SEQ ID NO: 18) | |
| CDR2(CDR-L2): ATSTLDS | (SEQ ID NO: 19) | |
| CDR3(CDR-L3): LQFDSSPLT | (SEQ ID NO: 20) | |
| FR1: DIQMTQSPSSLSASLGERVSLTC | (SEQ ID NO: 21) | |
| FR2: WIQQEPDGTIKRLIY | (SEQ ID NO: 22) | |
| FR3: GVPKRFSGSRSGSDYFLTISSLESEDFVDYYC | (SEQ ID NO: 23) | |
| FR4: FGAGTKLELK | (SEQ ID NO: 24) | |

Antibody 2A16 Heavy Chain
(FR1 - <u>CDR1</u> - FR2 - <u>CDR2</u> - FR3 - <u>CDR3</u> - FR4)

MDWLWNLLFLMAAAQSIQAQIQLVQSGPELKKPGETVKISCKASGYTFT<u>KHGMN</u>**WMKQAPGKGLK
WMG<u>WINTNTGEPTYSEEFKG</u>RFAFSLETSASTAYLQINNLKNEDTATYFCAR<u>TGRYGVDY</u>WGKGT
SVTVSS**    (SEQ ID NO: 25)

QIQLVQSGPELKKPGETVKISCKASGYTFT<u>KHGMN</u>WMKQAPGKGLKWMG<u>WINTNTGEPTYSEEFK
G</u>RFAFSLETSASTAYLQINNLKNEDTATYFCAR<u>TGRYGVDY</u>WGKGTSVTVSS
                                                        (SEQ ID NO: 39)

CDR1(CDR-H1): KHGMN                    (SEQ ID NO: 26)
CDR2(CDR-H2): WINTNTGEPTYSEEFKG        (SEQ ID NO: 27)
CDR3(CDR-H3): TGRYGVDY                 (SEQ ID NO: 28)

FR1 (FR-H1): QIQLVQSGPELKKPGETVKISCKASGYTFT    (SEQ ID NO: 29)
FR2 (FR-H2): WMKQAPGKGLKWMG                    (SEQ ID NO: 30)
FR3 (FR-H3): RFAFSLETSASTAYLQINNLKNEDTATYFCAR  (SEQ ID NO: 31)
FR4 (FR-H4): WGKGTSVTVSS                       (SEQ ID NO: 32)

FIG. 11A  Enteroendocrine NMU⁺ cells
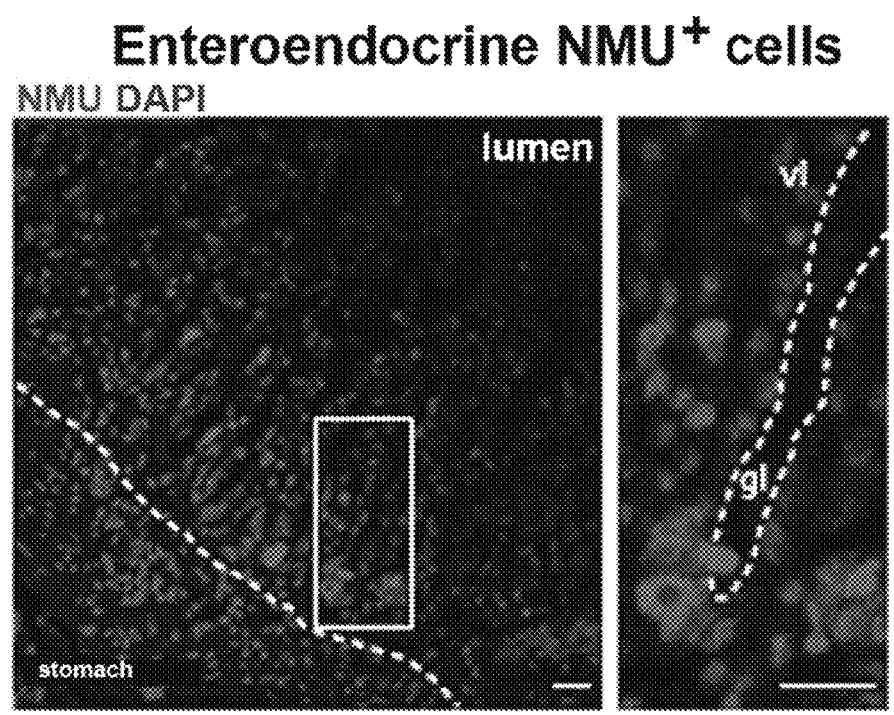
FIG. 11B
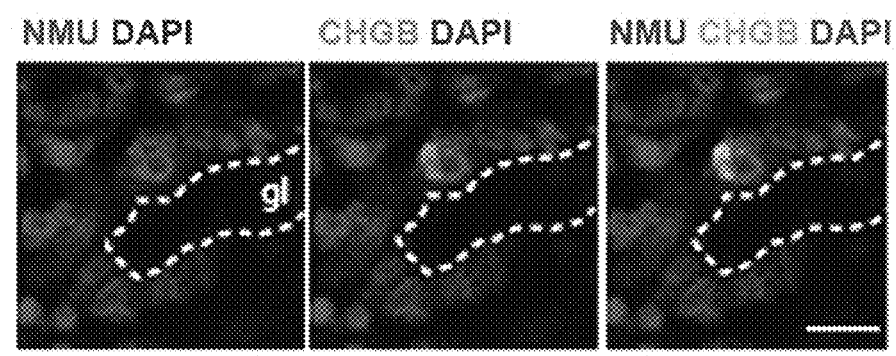

Effects of Nmu infusion *in vivo*
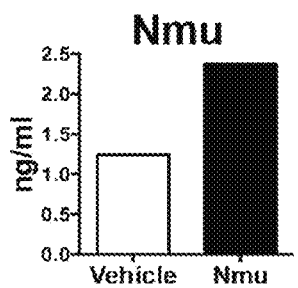
FIG. 13A
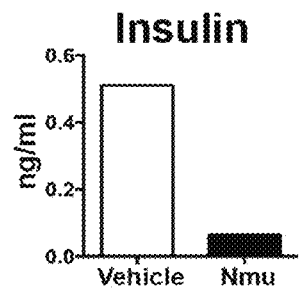
FIG. 13B
FIG. 13C
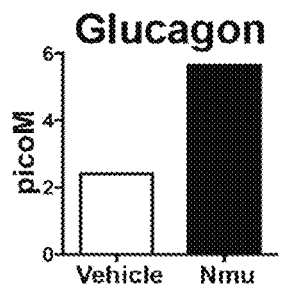
FIG. 13D
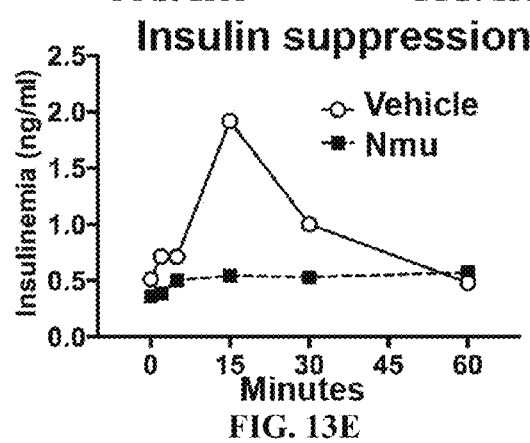
FIG. 13E
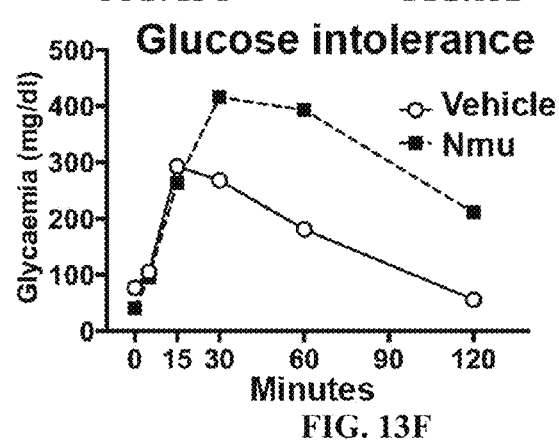
FIG. 13F
Increased ectopic pancreatic NMU in pancreatitis and pancreatic cancer
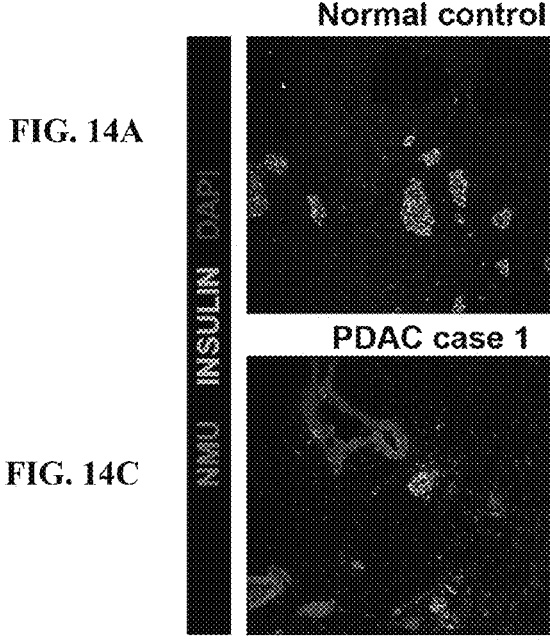
FIG. 14A
FIG. 14B
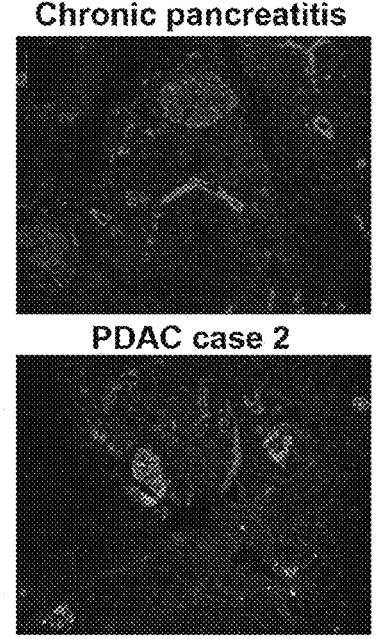
FIG. 14C
FIG. 14D Misexpression of NMU by α-cells in human PDAC Meta-analysis: increased *NMU* mRNA expression in PDAC ☐ Saline  ■ 0.3 mg/kg/h NMU-23

SEQUENCE LISTING

```
<160> NUMBER OF SEQ ID NOS: 42

<210> SEQ ID NO 1
<211> LENGTH: 133
<212> TYPE: PRT
<213> ORGANISM: Artificial sequence
<220> FEATURE:
<223> OTHER INFORMATION: Synthetic sequence

<400> SEQUENCE: 1

Met Glu Ser Gln Thr Gln Val Leu Met Phe Leu Leu Leu Trp Val Ser
1               5                   10                  15

Gly Ala Cys Ala Asn Ile Val Met Thr Gln Ser Pro Ser Ser Leu Ala
            20                  25                  30
```

Met Ser Ile Gly Gln Lys Val Thr Met Ser Cys Arg Ser Ser Gln Ser
            35                  40                  45

Leu Leu Asn Ser Ser Asn Gln Lys Asn Tyr Leu Ala Trp Tyr Gln Gln
    50                  55                  60

Lys Pro Gly Gln Ser Pro Lys Leu Leu Val Tyr Phe Ala Ser Thr Arg
65                  70                  75                  80

Glu Ser Gly Val Pro Ala Arg Phe Ile Gly Ser Gly Ser Gly Thr Asp
                85                  90                  95

Phe Thr Leu Thr Ile Ser Ser Val Gln Ala Glu Asp Leu Ala Asp Tyr
            100                 105                 110

Phe Cys Gln Gln His Tyr Ser Thr Pro Phe Thr Phe Gly Ser Gly Thr
        115                 120                 125

Lys Leu Glu Ile Lys
    130

<210> SEQ ID NO 2
<211> LENGTH: 17
<212> TYPE: PRT
<213> ORGANISM: Artificial sequence
<220> FEATURE:
<223> OTHER INFORMATION: Synthetic sequence

<400> SEQUENCE: 2

Arg Ser Ser Gln Ser Leu Leu Asn Ser Ser Asn Gln Lys Asn Tyr Leu
1               5                   10                  15

Ala

<210> SEQ ID NO 3
<211> LENGTH: 7
<212> TYPE: PRT
<213> ORGANISM: Artificial sequence
<220> FEATURE:
<223> OTHER INFORMATION: Synthetic sequence

<400> SEQUENCE: 3

Phe Ala Ser Thr Arg Glu Ser
1               5

<210> SEQ ID NO 4
<211> LENGTH: 9
<212> TYPE: PRT
<213> ORGANISM: Artificial sequence
<220> FEATURE:
<223> OTHER INFORMATION: Synthetic sequence

<400> SEQUENCE: 4

Gln Gln His Tyr Ser Thr Pro Phe Thr
1               5

<210> SEQ ID NO 5
<211> LENGTH: 23
<212> TYPE: PRT
<213> ORGANISM: Artificial sequence
<220> FEATURE:
<223> OTHER INFORMATION: Synthetic sequence

<400> SEQUENCE: 5

Asn Ile Val Met Thr Gln Ser Pro Ser Ser Leu Ala Met Ser Ile Gly
1               5                   10                  15

Gln Lys Val Thr Met Ser Cys
            20

```
<210> SEQ ID NO 6
<211> LENGTH: 15
<212> TYPE: PRT
<213> ORGANISM: Artificial sequence
<220> FEATURE:
<223> OTHER INFORMATION: Synthetic sequence

<400> SEQUENCE: 6

Trp Tyr Gln Gln Lys Pro Gly Gln Ser Pro Lys Leu Leu Val Tyr
1               5                   10                  15

<210> SEQ ID NO 7
<211> LENGTH: 32
<212> TYPE: PRT
<213> ORGANISM: Artificial sequence
<220> FEATURE:
<223> OTHER INFORMATION: Synthetic sequence

<400> SEQUENCE: 7

Gly Val Pro Ala Arg Phe Ile Gly Ser Gly Ser Gly Thr Asp Phe Thr
1               5                   10                  15

Leu Thr Ile Ser Ser Val Gln Ala Glu Asp Leu Ala Asp Tyr Phe Cys
            20                  25                  30

<210> SEQ ID NO 8
<211> LENGTH: 10
<212> TYPE: PRT
<213> ORGANISM: Artificial sequence
<220> FEATURE:
<223> OTHER INFORMATION: Synthetic sequence

<400> SEQUENCE: 8

Phe Gly Ser Gly Thr Lys Leu Glu Ile Lys
1               5                   10

<210> SEQ ID NO 9
<211> LENGTH: 133
<212> TYPE: PRT
<213> ORGANISM: Artificial sequence
<220> FEATURE:
<223> OTHER INFORMATION: Synthetic sequence

<400> SEQUENCE: 9

Met Lys Cys Ser Trp Val Ile Phe Phe Leu Met Ala Val Val Ile Gly
1               5                   10                  15

Ile Asn Ser Glu Val Gln Leu Gln Gln Ser Gly Ala Glu Leu Val Arg
            20                  25                  30

Ser Gly Ala Ser Val Lys Leu Ser Cys Ala Ala Ser Gly Phe Asn Ile
        35                  40                  45

Lys Asp Tyr Tyr Ile His Trp Val Lys Gln Arg Pro Glu Gln Gly Leu
    50                  55                  60

Glu Trp Ile Gly Trp Ile Asp Pro Glu Asn Gly Asp Asn Glu Cys Ala
65                  70                  75                  80

Pro Lys Phe Gln Gly Lys Ala Thr Met Thr Ala Asp Thr Ser Ser Asn
                85                  90                  95

Thr Ala Tyr Leu Gln Leu Thr Ser Leu Thr Ser Glu Asp Thr Ala Val
            100                 105                 110

Tyr Tyr Cys Asn Ala Gly Lys Gly Asp Tyr Trp Gly Gln Gly Thr Thr
        115                 120                 125

Leu Thr Val Ser Ser
    130
```

<210> SEQ ID NO 10
<211> LENGTH: 5
<212> TYPE: PRT
<213> ORGANISM: Artificial sequence
<220> FEATURE:
<223> OTHER INFORMATION: Synthetic sequence

<400> SEQUENCE: 10

Asp Tyr Tyr Ile His
1               5

<210> SEQ ID NO 11
<211> LENGTH: 17
<212> TYPE: PRT
<213> ORGANISM: Artificial sequence
<220> FEATURE:
<223> OTHER INFORMATION: Synthetic sequence

<400> SEQUENCE: 11

Trp Ile Asp Pro Glu Asn Gly Asp Asn Glu Cys Ala Pro Lys Phe Gln
1               5                  10                  15

Gly

<210> SEQ ID NO 12
<211> LENGTH: 5
<212> TYPE: PRT
<213> ORGANISM: Artificial sequence
<220> FEATURE:
<223> OTHER INFORMATION: Synthetic sequence

<400> SEQUENCE: 12

Gly Lys Gly Asp Tyr
1               5

<210> SEQ ID NO 13
<211> LENGTH: 30
<212> TYPE: PRT
<213> ORGANISM: Artificial sequence
<220> FEATURE:
<223> OTHER INFORMATION: Synthetic sequence

<400> SEQUENCE: 13

Glu Val Gln Leu Gln Gln Ser Gly Ala Glu Leu Val Arg Ser Gly Ala
1               5                  10                  15

Ser Val Lys Leu Ser Cys Ala Ala Ser Gly Phe Asn Ile Lys
                20                  25                  30

<210> SEQ ID NO 14
<211> LENGTH: 14
<212> TYPE: PRT
<213> ORGANISM: Artificial sequence
<220> FEATURE:
<223> OTHER INFORMATION: Synthetic sequence

<400> SEQUENCE: 14

Trp Val Lys Gln Arg Pro Glu Gln Gly Leu Glu Trp Ile Gly
1               5                  10

<210> SEQ ID NO 15
<211> LENGTH: 32
<212> TYPE: PRT
<213> ORGANISM: Artificial sequence
<220> FEATURE:
<223> OTHER INFORMATION: Synthetic sequence

<400> SEQUENCE: 15

```
Lys Ala Thr Met Thr Ala Asp Thr Ser Ser Asn Thr Ala Tyr Leu Gln
1               5                   10                  15

Leu Thr Ser Leu Thr Ser Glu Asp Thr Ala Val Tyr Tyr Cys Asn Ala
            20                  25                  30
```

<210> SEQ ID NO 16
<211> LENGTH: 11
<212> TYPE: PRT
<213> ORGANISM: Artificial sequence
<220> FEATURE:
<223> OTHER INFORMATION: Synthetic sequence

<400> SEQUENCE: 16

```
Trp Gly Gln Gly Thr Thr Leu Thr Val Ser Ser
1               5                   10
```

<210> SEQ ID NO 17
<211> LENGTH: 129
<212> TYPE: PRT
<213> ORGANISM: Artificial sequence
<220> FEATURE:
<223> OTHER INFORMATION: Synthetic sequence

<400> SEQUENCE: 17

```
Met Asp Met Arg Ala Pro Ala Gln Ile Phe Gly Phe Leu Leu Leu Leu
1               5                   10                  15

Phe Pro Gly Thr Arg Cys Asp Ile Gln Met Thr Gln Ser Pro Ser Ser
            20                  25                  30

Leu Ser Ala Ser Leu Gly Glu Arg Val Ser Leu Thr Cys Arg Ala Ser
        35                  40                  45

Gln Asp Ile Gly Ser Asn Leu Asn Trp Ile Gln Gln Glu Pro Asp Gly
    50                  55                  60

Thr Ile Lys Arg Leu Ile Tyr Ala Thr Ser Thr Leu Asp Ser Gly Val
65                  70                  75                  80

Pro Lys Arg Phe Ser Gly Ser Arg Ser Gly Ser Asp Tyr Phe Leu Thr
                85                  90                  95

Ile Ser Ser Leu Glu Ser Glu Asp Phe Val Asp Tyr Tyr Cys Leu Gln
            100                 105                 110

Phe Asp Ser Ser Pro Leu Thr Phe Gly Ala Gly Thr Lys Leu Glu Leu
        115                 120                 125

Lys
```

<210> SEQ ID NO 18
<211> LENGTH: 11
<212> TYPE: PRT
<213> ORGANISM: Artificial sequence
<220> FEATURE:
<223> OTHER INFORMATION: Synthetic sequence

<400> SEQUENCE: 18

```
Arg Ala Ser Gln Asp Ile Gly Ser Asn Leu Asn
1               5                   10
```

<210> SEQ ID NO 19
<211> LENGTH: 7
<212> TYPE: PRT
<213> ORGANISM: Artificial sequence
<220> FEATURE:
<223> OTHER INFORMATION: Synthetic sequence

<400> SEQUENCE: 19

```
Ala Thr Ser Thr Leu Asp Ser
1               5

<210> SEQ ID NO 20
<211> LENGTH: 9
<212> TYPE: PRT
<213> ORGANISM: Artificial sequence
<220> FEATURE:
<223> OTHER INFORMATION: Synthetic sequence

<400> SEQUENCE: 20

Leu Gln Phe Asp Ser Ser Pro Leu Thr
1               5

<210> SEQ ID NO 21
<211> LENGTH: 23
<212> TYPE: PRT
<213> ORGANISM: Artificial sequence
<220> FEATURE:
<223> OTHER INFORMATION: Synthetic sequence

<400> SEQUENCE: 21

Asp Ile Gln Met Thr Gln Ser Pro Ser Ser Leu Ser Ala Ser Leu Gly
1               5                   10                  15

Glu Arg Val Ser Leu Thr Cys
            20

<210> SEQ ID NO 22
<211> LENGTH: 15
<212> TYPE: PRT
<213> ORGANISM: Artificial sequence
<220> FEATURE:
<223> OTHER INFORMATION: Synthetic sequence

<400> SEQUENCE: 22

Trp Ile Gln Gln Glu Pro Asp Gly Thr Ile Lys Arg Leu Ile Tyr
1               5                   10                  15

<210> SEQ ID NO 23
<211> LENGTH: 32
<212> TYPE: PRT
<213> ORGANISM: Artificial sequence
<220> FEATURE:
<223> OTHER INFORMATION: Synthetic sequence

<400> SEQUENCE: 23

Gly Val Pro Lys Arg Phe Ser Gly Ser Arg Ser Gly Ser Asp Tyr Phe
1               5                   10                  15

Leu Thr Ile Ser Ser Leu Glu Ser Glu Asp Phe Val Asp Tyr Tyr Cys
            20                  25                  30

<210> SEQ ID NO 24
<211> LENGTH: 10
<212> TYPE: PRT
<213> ORGANISM: Artificial sequence
<220> FEATURE:
<223> OTHER INFORMATION: Synthetic sequence

<400> SEQUENCE: 24

Phe Gly Ala Gly Thr Lys Leu Glu Leu Lys
1               5                   10

<210> SEQ ID NO 25
<211> LENGTH: 136
<212> TYPE: PRT
<213> ORGANISM: Artificial sequence
```

```
<220> FEATURE:
<223> OTHER INFORMATION: Synthetic sequence

<400> SEQUENCE: 25

Met Asp Trp Leu Trp Asn Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Lys His Gly Met Asn Trp Met Lys Gln Ala Pro Gly Lys Gly Leu
    50                  55                  60

Lys Trp Met Gly Trp Ile Asn Thr Asn Thr Gly Glu Pro Thr Tyr Ser
65                  70                  75                  80

Glu Glu Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Thr Gly Arg Tyr Gly Val Asp Tyr Trp Gly Lys
        115                 120                 125

Gly Thr Ser Val Thr Val Ser Ser
    130                 135

<210> SEQ ID NO 26
<211> LENGTH: 5
<212> TYPE: PRT
<213> ORGANISM: Artificial sequence
<220> FEATURE:
<223> OTHER INFORMATION: Synthetic sequence

<400> SEQUENCE: 26

Lys His Gly Met Asn
1               5

<210> SEQ ID NO 27
<211> LENGTH: 17
<212> TYPE: PRT
<213> ORGANISM: Artificial sequence
<220> FEATURE:
<223> OTHER INFORMATION: Synthetic sequence

<400> SEQUENCE: 27

Trp Ile Asn Thr Asn Thr Gly Glu Pro Thr Tyr Ser Glu Glu Phe Lys
1               5                   10                  15

Gly

<210> SEQ ID NO 28
<211> LENGTH: 8
<212> TYPE: PRT
<213> ORGANISM: Artificial sequence
<220> FEATURE:
<223> OTHER INFORMATION: Synthetic sequence

<400> SEQUENCE: 28

Thr Gly Arg Tyr Gly Val Asp Tyr
1               5

<210> SEQ ID NO 29
<211> LENGTH: 30
<212> TYPE: PRT
<213> ORGANISM: Artificial sequence
<220> FEATURE:
```

<223> OTHER INFORMATION: Synthetic sequence

<400> SEQUENCE: 29

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr
            20                  25                  30

<210> SEQ ID NO 30
<211> LENGTH: 14
<212> TYPE: PRT
<213> ORGANISM: Artificial sequence
<220> FEATURE:
<223> OTHER INFORMATION: Synthetic sequence

<400> SEQUENCE: 30

Trp Met Lys Gln Ala Pro Gly Lys Gly Leu Lys Trp Met Gly
1               5                   10

<210> SEQ ID NO 31
<211> LENGTH: 32
<212> TYPE: PRT
<213> ORGANISM: Artificial sequence
<220> FEATURE:
<223> OTHER INFORMATION: Synthetic sequence

<400> SEQUENCE: 31

Arg Phe Ala Phe Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Arg
            20                  25                  30

<210> SEQ ID NO 32
<211> LENGTH: 11
<212> TYPE: PRT
<213> ORGANISM: Artificial sequence
<220> FEATURE:
<223> OTHER INFORMATION: Synthetic sequence

<400> SEQUENCE: 32

Trp Gly Lys Gly Thr Ser Val Thr Val Ser Ser
1               5                   10

<210> SEQ ID NO 33
<211> LENGTH: 25
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (25)..(25)
<223> OTHER INFORMATION: The C-terminal amino acid of this mature
      peptide has an amidation

<400> SEQUENCE: 33

Phe Arg Val Asp Glu Glu Phe Gln Ser Pro Phe Ala Ser Gln Ser Arg
1               5                   10                  15

Gly Tyr Phe Leu Phe Arg Pro Arg Asn
            20                  25

<210> SEQ ID NO 34
<211> LENGTH: 12
<212> TYPE: PRT
<213> ORGANISM: Artificial sequence
<220> FEATURE:

```
<223> OTHER INFORMATION: Synthetic sequence

<400> SEQUENCE: 34

Gln Ser Arg Gly Tyr Phe Leu Phe Arg Pro Arg Asn
1               5                   10

<210> SEQ ID NO 35
<211> LENGTH: 13
<212> TYPE: PRT
<213> ORGANISM: Artificial sequence
<220> FEATURE:
<223> OTHER INFORMATION: Synthetic sequence

<400> SEQUENCE: 35

Phe Arg Val Asp Glu Glu Phe Gln Ser Pro Phe Ala Ser
1               5                   10

<210> SEQ ID NO 36
<211> LENGTH: 113
<212> TYPE: PRT
<213> ORGANISM: Artificial sequence
<220> FEATURE:
<223> OTHER INFORMATION: Synthetic sequence

<400> SEQUENCE: 36

Asn Ile Val Met Thr Gln Ser Pro Ser Ser Leu Ala Met Ser Ile Gly
1               5                   10                  15

Gln Lys Val Thr Met Ser Cys Arg Ser Ser Gln Ser Leu Leu Asn Ser
                20                  25                  30

Ser Asn Gln Lys Asn Tyr Leu Ala Trp Tyr Gln Gln Lys Pro Gly Gln
            35                  40                  45

Ser Pro Lys Leu Leu Val Tyr Phe Ala Ser Thr Arg Glu Ser Gly Val
        50                  55                  60

Pro Ala Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Phe Thr Phe Gly Ser Gly Thr Lys Leu Glu Ile
            100                 105                 110

Lys

<210> SEQ ID NO 37
<211> LENGTH: 114
<212> TYPE: PRT
<213> ORGANISM: Artificial sequence
<220> FEATURE:
<223> OTHER INFORMATION: Synthetic sequence

<400> SEQUENCE: 37

Glu Val Gln Leu Gln Gln Ser Gly Ala Glu Leu Val Arg Ser Gly Ala
1               5                   10                  15

Ser Val Lys Leu Ser Cys Ala Ala Ser Gly Phe Asn Ile Lys Asp Tyr
                20                  25                  30

Tyr Ile His Trp Val Lys Gln Arg Pro Glu Gln Gly Leu Glu Trp Ile
            35                  40                  45

Gly Trp Ile Asp Pro Glu Asn Gly Asp Asn Glu Cys Ala Pro Lys Phe
        50                  55                  60

Gln Gly Lys Ala Thr Met Thr Ala Asp Thr Ser Ser Asn Thr Ala Tyr
65                  70                  75                  80

Leu Gln Leu Thr Ser Leu Thr Ser Glu Asp Thr Ala Val Tyr Tyr Cys
```

```
                     85                  90                  95

Asn Ala Gly Lys Gly Asp Tyr Trp Gly Gln Gly Thr Thr Leu Thr Val
                100                 105                 110

Ser Ser

<210> SEQ ID NO 38
<211> LENGTH: 107
<212> TYPE: PRT
<213> ORGANISM: Artificial sequence
<220> FEATURE:
<223> OTHER INFORMATION: Synthetic sequence

<400> SEQUENCE: 38

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Asn
                20                  25                  30

Leu Asn Trp Ile Gln Gln Glu Pro Asp Gly Thr Ile Lys Arg Leu Ile
            35                  40                  45

Tyr Ala Thr Ser Thr Leu Asp Ser Gly Val Pro Lys Arg Phe Ser Gly
    50                  55                  60

Ser Arg Ser Gly Ser Asp Tyr Phe Leu Thr Ile Ser Ser Leu Glu Ser
65                  70                  75                  80

Glu Asp Phe Val Asp Tyr Tyr Cys Leu Gln Phe Asp Ser Ser Pro Leu
                85                  90                  95

Thr Phe Gly Ala Gly Thr Lys Leu Glu Leu Lys
                100                 105

<210> SEQ ID NO 39
<211> LENGTH: 117
<212> TYPE: PRT
<213> ORGANISM: Artificial sequence
<220> FEATURE:
<223> OTHER INFORMATION: Synthetic sequence

<400> SEQUENCE: 39

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Lys His
                20                  25                  30

Gly Met Asn Trp Met Lys Gln Ala Pro Gly Lys Gly Leu Lys Trp Met
            35                  40                  45

Gly Trp Ile Asn Thr Asn Thr Gly Glu Pro Thr Tyr Ser Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Thr Gly Arg Tyr Gly Val Asp Tyr Trp Gly Lys Gly Thr Ser
                100                 105                 110

Val Thr Val Ser Ser
        115

<210> SEQ ID NO 40
<211> LENGTH: 174
<212> TYPE: PRT
<213> ORGANISM: Homo sapiens

<400> SEQUENCE: 40
```

Met Leu Arg Thr Glu Ser Cys Arg Pro Arg Ser Pro Ala Gly Gln Val
1               5                   10                  15

Ala Ala Ala Ser Pro Leu Leu Leu Leu Leu Leu Leu Ala Trp Cys
            20                  25                  30

Ala Gly Ala Cys Arg Gly Ala Pro Ile Leu Pro Gln Gly Leu Gln Pro
            35                  40                  45

Glu Gln Gln Leu Gln Leu Trp Asn Glu Ile Asp Asp Thr Cys Ser Ser
        50                  55                  60

Phe Leu Ser Ile Asp Ser Gln Pro Gln Ala Ser Asn Ala Leu Glu Glu
65                  70                  75                  80

Leu Cys Phe Met Ile Met Gly Met Leu Pro Lys Pro Gln Glu Gln Asp
                85                  90                  95

Glu Lys Asp Asn Thr Lys Arg Phe Leu Phe His Tyr Ser Lys Thr Gln
            100                 105                 110

Lys Leu Gly Lys Ser Asn Val Val Ser Ser Val Val His Pro Leu Leu
        115                 120                 125

Gln Leu Val Pro His Leu His Glu Arg Arg Met Lys Arg Phe Arg Val
130                 135                 140

Asp Glu Glu Phe Gln Ser Pro Phe Ala Ser Gln Ser Arg Gly Tyr Phe
145                 150                 155                 160

Leu Phe Arg Pro Arg Asn Gly Arg Arg Ser Ala Gly Phe Ile
                165                 170

<210> SEQ ID NO 41
<211> LENGTH: 158
<212> TYPE: PRT
<213> ORGANISM: Homo sapiens

<400> SEQUENCE: 41

Met Leu Arg Thr Glu Ser Cys Arg Pro Arg Ser Pro Ala Gly Gln Val
1               5                   10                  15

Ala Ala Ala Ser Pro Leu Leu Leu Leu Leu Leu Leu Ala Trp Cys
            20                  25                  30

Ala Gly Ala Cys Arg Gly Ala Pro Ile Leu Pro Gln Gly Leu Gln Pro
            35                  40                  45

Glu Gln Gln Leu Gln Leu Trp Asn Glu Ala Ser Asn Ala Leu Glu Glu
        50                  55                  60

Leu Cys Phe Met Ile Met Gly Met Leu Pro Lys Pro Gln Glu Gln Asp
65                  70                  75                  80

Glu Lys Asp Asn Thr Lys Arg Phe Leu Phe His Tyr Ser Lys Thr Gln
                85                  90                  95

Lys Leu Gly Lys Ser Asn Val Val Ser Ser Val Val His Pro Leu Leu
            100                 105                 110

Gln Leu Val Pro His Leu His Glu Arg Arg Met Lys Arg Phe Arg Val
        115                 120                 125

Asp Glu Glu Phe Gln Ser Pro Phe Ala Ser Gln Ser Arg Gly Tyr Phe
130                 135                 140

Leu Phe Arg Pro Arg Asn Gly Arg Arg Ser Ala Gly Phe Ile
145                 150                 155

<210> SEQ ID NO 42
<211> LENGTH: 174
<212> TYPE: PRT
<213> ORGANISM: Mus musculus

<400> SEQUENCE: 42

```
Met Ser Arg Ala Ala Gly His Arg Pro Gly Leu Ser Ala Gly Gln Leu
1               5                   10                  15

Ala Ala Ala Thr Ala Ser Pro Leu Leu Ser Leu Leu Leu Leu Leu Ala
                20                  25                  30

Cys Cys Ala Asp Ala Cys Lys Gly Val Pro Ile Ser Pro Gln Arg Leu
            35                  40                  45

Gln Pro Glu Gln Glu Leu Gln Leu Trp Asn Glu Ile His Glu Ala Cys
        50                  55                  60

Ala Ser Phe Leu Ser Ile Asp Ser Arg Pro Gln Ala Ser Val Ala Leu
65                      70                  75                  80

Arg Glu Leu Cys Arg Ile Val Met Glu Ile Ser Gln Lys Pro Gln Glu
                85                  90                  95

Gln Ser Glu Lys Asp Asn Thr Lys Arg Phe Leu Phe His Tyr Ser Lys
                100                 105                 110

Thr Gln Lys Leu Gly Asn Ser Asn Val Val Ser Ser Val Val His Pro
            115                 120                 125

Leu Leu Gln Leu Val Pro Gln Leu His Glu Arg Arg Met Lys Arg Phe
        130                 135                 140

Lys Ala Glu Tyr Gln Ser Pro Ser Val Gly Gln Ser Lys Gly Tyr Phe
145                 150                 155                 160

Leu Phe Arg Pro Arg Asn Gly Lys Arg Ser Thr Ser Phe Ile
                165                 170
```

COMPOSITIONS AND METHODS FOR MEASURING NMU AND FOR TREATMENT USING ANTI-NMU AGENTS

CROSS-REFERENCE

This application claims the benefit and is a division of U.S. patent application Ser. No. 15/418,550, filed Jan. 27, 2017, which claims benefit of U.S. Provisional Patent Application No. 62/288,985, filed Jan. 29, 2016; each of which is incorporated herein by reference in its entirety.

INTRODUCTION

The coupling of hormonal responses to nutrient availability is fundamental for metabolic control. In mammals, regulated secretion of insulin from pancreatic beta cells is a principal hormonal response orchestrating metabolic homeostasis. Circulating insulin levels constitute a dynamic metabolic switch, signaling the fed state and nutrient storage (anabolic pathways) when elevated, or starvation and nutrient mobilization (catabolic pathways) when decreased.

Thus, insulin secretion must be precisely tuned to the nutritional state of the animal. Increased circulating glucose stimulates beta cell depolarization and insulin secretion. In concert with glucose, gut-derived incretin hormones amplify glucose-stimulated insulin secretion (GSIS) in response to ingested carbohydrates, thereby tuning insulin output to the feeding state of the host.

There is a well-recognized 'risk heterogeneity' for morbidity and mortality in common human insulin-linked diseases like type 2 diabetes, obesity, pancreas cancer and pancreatitis. The combined burden of these diseases on human health and economy is enormous.

There is a need in the art for new treatments (e.g., treatments that regulate insulin secretion) and prediction methods for diseases such as diabetes, obesity, pancreatic cancer, and pancreatitis.

SUMMARY

The inventors have shown that NMU is a hormone that regulates (suppresses) human insulin output by acting through its receptor, neuromedin U receptor (NMUR1), expressed on pancreatic beta-cells. The inventors have generated and characterized mice lacking the NMUR1 receptor, and have also produced two high specificity and high affinity monoclonal antibodies (C578 and 2A16) that bind to human neuromedin U (NMU). These antibodies are injectable, block the interaction between circulating NMU and NMUR1 expressed on cells, and in vivo studies show that injection of the antibodies is sufficient to suppress NMU levels, leading to enhanced insulin output and glucose handling. The inventors have also shown that the antibodies can also be used as part of a two-way enzyme linked immunosorption assay (ELISA) that is sensitive enough to detect NMU in serum from mice as well as humans.

Measuring NMU (e.g., using a subject two-way ELISA) can effectively stratify and identify broad subsets of patients with excessive NMU signaling that may benefit from NMU antibody-based therapies. For example, using the two-way ELISA, NMU levels were shown to be elevated in obesity states.

Methods and compositions are provided for treating an individual in need thereof (e.g., an individual who is obese and/or has diabetes, e.g., type 2 diabetes) by administering an anti-NMU/NMUR agent (e.g., an anti-NMU antibody). For example, methods and compositions are provided for increasing circulating insulin in an individual. Methods and compositions are also provided for detecting neuromedin U (NMU) (e.g., in a biological sample such as serum), e.g., using a two-way ELISA that includes one or two anti-NMU antibodies (or binding fragments thereof), each having the light chain and/or heavy chain CDRs of a new antibody disclosed herein. Methods and compositions are also provided for predicting whether an individual will develop diabetes, e.g., type 2 diabetes, and/or PDAC, and for identifying an individual who would benefit from administration of an anti-NMU/NMUR agent (e.g., in some cases using a subject two-way ELISA).

Provided are methods of treating an individual in need thereof (e.g., an individual with diabetes, e.g., type 2 diabetes, or who is suspected of having an increased risk of developing diabetes, e.g., type 2 diabetes, an individual who is obese and/or has a family history that includes diabetics; an individual that has cystic fibrosis, familial pancreatitis, idiopathic pancreatitis, type 3c diabetes mellitus, late stage pancreatic cancer, and/or cancer cachexia; an individual who has an increased level of circulating NMU relative to a reference level; and the like), where the method includes administering to an individual, at a dose effective to increase the amount of circulating insulin in the individual, an anti-NMU/NMUR agent that reduces binding between NMU and NMUR1. Also provided are methods of increasing circulating insulin in an individual (e.g., an individual with diabetes, e.g., type 2 diabetes, or who is suspected of having an increased risk of developing diabetes; an individual who is obese and/or has a family history that includes diabetics; an individual that has cystic fibrosis, familial pancreatitis, idiopathic pancreatitis, type 3c diabetes mellitus, late stage pancreatic cancer, and/or cancer cachexia; an individual who has an increased level of circulating NMU relative to a reference level; and the like), where the method includes administering to an individual, at a dose effective to increase the amount of circulating insulin in the individual, an anti-NMU/NMUR agent that reduces binding between NMU and NMUR1.

With regard to either of the above methods, in some cases, the anti-NMU/NMUR agent binds to NMU. In some cases, the anti-NMU/NMUR agent is an anti-NMU antibody or antigen binding region thereof. In some cases, the anti-NMU antibody or antigen binding region thereof is humanized. In some cases, the anti-NMU antibody or antigen binding region thereof comprises a light chain comprising a CDR-L1, CDR-L2, and CDR-L3 comprising the amino acid sequences set forth in SEQ ID NOs: 18-20, respectively, or SEQ ID NOs: 2-4, respectively. In some cases, the anti-NMU antibody or antigen binding region thereof comprises a heavy chain comprising a CDR-H1, CDR-H2, and CDR-H3 comprising the amino acid sequences set forth in SEQ ID NOs: 26-28, respectively, or SEQ ID NOs: 10-12, respectively. In some cases, the anti-NMU antibody or antigen binding region thereof comprises a light chain comprising the amino acid sequence set forth in any one of SEQ ID NOs: 17, 38, 1, and 36. In some cases, the anti-NMU antibody or antigen binding region thereof comprises a heavy chain comprising the amino acid sequence set forth in any one of SEQ ID NOs: 25, 39, 9, and 37. In some cases, the anti-NMU antibody or antigen binding region thereof comprises a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28. In some cases, the anti-NMU antibody or antigen binding region thereof comprises a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12.

Also provided are proteins that bind specifically to NMU and include an antigen binding region that includes one or more of: (a) a light chain comprising a CDR-L1, CDR-L2, and CDR-L3 comprising the amino acid sequences set forth in SEQ ID NOs: 18-20, respectively, or SEQ ID NOs: 2-4, respectively; and (b) a heavy chain comprising a CDR-H1, CDR-H2, and CDR-H3 comprising the amino acid sequences set forth in SEQ ID NOs: 26-28, respectively, or SEQ ID NOs: 10-12, respectively. In some cases, the antigen binding region comprises one or more of: (a) a light chain comprising the amino acid sequence set forth in any one of SEQ ID NOs: 17, 38, 1, and 36; and (b) a heavy chain comprising the amino acid sequence set forth in any one of SEQ ID NOs: 25, 39, 9, and 37. In some cases, the antigen binding region comprises a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28, respectively. In some cases, the antigen binding region comprises a light chain that comprises the amino acid sequence set forth in any one of SEQ ID NOs: 17 and 38, and a heavy chain that comprises the amino acid sequence set forth in any one of SEQ ID NOs: 25 and 39. In some cases, the antigen binding region comprises a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12, respectively. In some cases, the antigen binding region comprises a light chain that comprises the amino acid sequence set forth in any one of SEQ ID NOs: 1 and 36, and a heavy chain that comprises the amino acid sequence set forth in any one of SEQ ID NOs: 9 and 37. In some cases, the protein is an antibody (e.g., a mouse or human antibody). In some cases, the antibody is a humanized antibody. Also provided are nucleic acids (e.g., expression vectors) encoding the above proteins. Also provided are cells that include one or more nucleic acids (e.g., expression vectors) encoding the above proteins.

Provided are kits (e.g., for detecting neuromedin U (NMU)) the include a first anti-NMU antibody and a second anti-NMU antibody, where the first and second anti-NMU antibodies bind to non-overlapping amino acids of NMU, and where one of the first and second anti-NMU antibody antibodies includes: (a) a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28, respectively; or (b) a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12, respectively. In some cases: (i) one of the first and second anti-NMU antibodies comprises a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28, respectively; and (ii) the other of the first and second anti-NMU antibodies comprises a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12, respectively. In some cases, the first anti-NMU antibody is immobilized on a solid surface. In some cases, the solid surface is a bead or a surface of a well of a multi-well plate. In some cases, the second anti-NMU antibody is detectably labeled. In some cases, the second anti-NMU antibody is conjugated to a fluorophore, a fluorescent protein, or an enzyme that is indirectly detectable.

Provided are methods for detecting neuromedin U (NMU), where the methods include measuring an amount of NMU in a sample using a subject kit (e.g., any of the kits described above), where the method includes contacting NMU in the sample with the first and second anti-NMU antibodies, and measuring an amount of the second anti-NMU antibody. In some cases, the method includes: (a) contacting the sample with the first anti-NMU antibody, wherein the first anti-NMU antibody is immobilized on a solid surface and NMU of the sample binds to the first anti-NMU antibody; (b) contacting the NMU that is bound to the first anti-NMU antibody with the second anti-NMU antibody; and (c) measuring an amount of the second anti-NMU antibody. In some cases, the method includes performing a first wash step between steps (a) and (b), and performing a second wash step between steps (b) and (c).

Provided are methods of predicting whether an individual will develop diabetes, e.g., type 2 diabetes, where the methods include: (a) measuring an amount of NMU present in a blood sample from an individual, (b) determining that the amount of NMU present in the blood sample is greater than or equal to a reference value; and (c) predicting that the individual will develop diabetes, e.g., type 2 diabetes. In some cases, the individual is suspected of having an increased risk of developing diabetes, e.g., type 2 diabetes. In some cases, the individual has a family history of diabetes, e.g., type 2 diabetes. In some cases, the individual is overweight. In some cases, the individual is obese.

Provided are methods of predicting whether an individual will develop PDAC or pancreatitis, where the methods include: (a) measuring an expression level of NMU in a biological sample from an individual, (b) determining that the measured expression level of NMU is greater than or equal to a reference value; and (c) predicting that the individual will develop PDAC or pancreatitis. In some cases, the individual is suspected of having an increased risk of developing PDAC or pancreatitis. In some cases, the individual has a family history of PDAC or pancreatitis.

Provided are methods of identifying an individual who would benefit from administration of an anti-NMU/NMUR agent, where the methods include: (a) measuring an amount of NMU present in a blood sample from an individual, (b) determining that the amount of NMU present in the blood sample is greater than or equal to a reference value; and (c) predicting that the individual would benefit from administration of an anti-NMU/NMUR agent. In some cases, the individual is suspected of having an increased risk of developing diabetes, e.g., type 2 diabetes, PDAC, or pancreatitis. In some cases, the individual has a family history of diabetes, e.g., type 2 diabetes, PDAC, or pancreatitis. In some cases, the individual is overweight. In some cases, the individual is obese.

In some cases (e.g., in any of the above methods), the sample is a blood sample. In some cases, the blood sample is a sample collected after an overnight fast. In some cases, the blood sample is a sample collected after a provocative challenge (e.g., a glucose challenge). In some cases, the measuring is not performed on exosomes isolated from the blood sample. In some cases, the measuring includes use of a two-way ELISA. In some cases, the measuring comprises contacting the NMU with a protein that: (i) binds specifically to NMU and (ii) includes an antigen binding region that comprises one or more of: (a) a light chain comprising a CDR-L1, CDR-L2, and CDR-L3 comprising the amino acid sequences set forth in SEQ ID NOs: 18-20, respectively, or SEQ ID NOs: 2-4, respectively; and (b) a heavy chain comprising a CDR-H1, CDR-H2, and CDR-H3 comprising the amino acid sequences set forth in SEQ ID NOs: 26-28, respectively, or SEQ ID NOs: 10-12, respectively. In some cases, the antigen binding region comprises one or more of: (a) a light chain comprising the amino acid sequence set forth in any one of SEQ ID NOs: 17, 38, 1, and 36; and (b) a heavy chain comprising the amino acid sequence set forth in any one of SEQ ID NOs: 25, 39, 9, and 37. In some cases, the antigen binding region comprises a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28, respectively. In some cases, the antigen binding region comprises a light chain that comprises the amino acid sequence set forth in any one of SEQ ID NOs: 17 and 38, and a heavy chain that comprises the amino acid sequence set forth in any one of SEQ ID NOs: 25 and 39. In some cases, the antigen binding region comprises a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12, respectively. In some cases, the antigen binding region comprises a light chain that comprises the amino acid sequence set forth in any one of SEQ ID NOs: 1 and 36, and a heavy chain that comprises the amino acid sequence set forth in any one of SEQ ID NOs: 9 and 37. In some cases, the protein is an antibody. In some cases, the antibody is a mouse or human antibody. In some cases, the antibody is a humanized antibody. In some cases, the method includes a step of collecting the blood sample (e.g., prior to the measuring step, prior to contacting the sample with an anti-NMU/NMUR agent, and the like).

In some cases, a subject method (e.g., a diagnostic method, a method of predicting, a method of identifying) includes (e.g., after a step of predicting), administering to the individual an anti-NMU/NMUR agent that reduces interaction between NMU and NMUR1 (e.g., an anti-NMU antibody), at a dose effective to increase the amount of circulating insulin in the individual.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A-1E. Depict data related to physiological dynamics of human and mouse NMU in vivo revealed by NMU ELISA assays.

FIG. 2A-2F. Depict data related to NMU suppressing post-prandial output in humans and mice.

FIG. 5A-5C. Depicts data related to NMU signaling loss in vivo improving metabolism in obesity.

FIG. 10. Depicts CDR sequences obtained from both light and heavy chains of newly generated anti-NMU antibodies (2A16 and C578).

FIG. 11A-11B. Depicts NMU immunoreactivity. vl=mucosal villus, gl=gland

FIG. 12A depicts data related to NmuR1 production being restricted to insulin$^+$ β cells. FIG. 12B-12C depict data related to showing that human NMU potently suppressed glucose-stimulated insulin secretion from human islets, FIG. 13A-13F. FIG. 13A depicts data showing that Nmu infusion led to a two-fold increase of mean serum Nmu levels. FIG. 13B-13D depicts data related to serum insulin and GLP-1 levels, which were reduces, and to glucagon levels, which were increased. FIG. 13E-13F depict data showing that reduced insulin secretion and impaired glucose tolerance were detected after oral glucose tolerance testing in mice infused with Nmu.

FIG. 14A-14D. Depict data related to NMU mis-expression in in chronic pancreatitis or pancreatic ductal adenocarcinoma.

FIG. 27A-28B relate to starvation diabetes in wildtype B6 mice. FIG. 27C-27D relate to NMU injection reconstituting starvation diabetes.

DETAILED DESCRIPTION

Figure 1D:
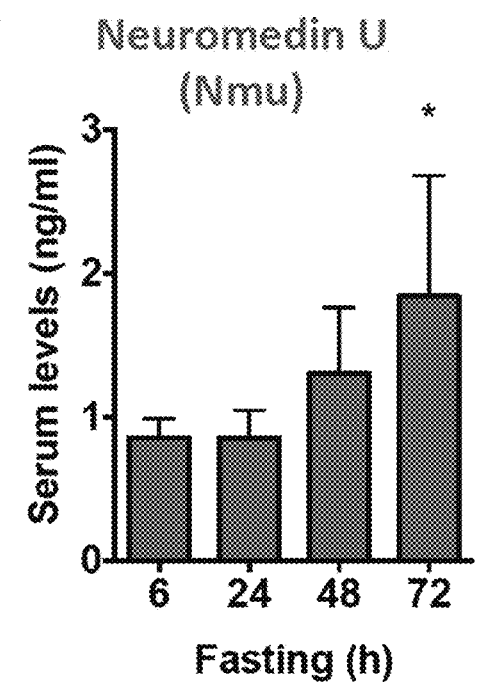

The inventors have shown that NMU is a hormone that regulates human insulin output by acting through its receptor, neuromedin U receptor (NMUR1), expressed on pancreatic beta-cells. The inventors have generated and characterized mice lacking the NMUR1 receptor, and have also produced two high specificity and high affinity monoclonal antibodies (C578 and 2A16) that bind to human neuromedin U (NMU). These antibodies are injectable, block the interaction between circulating NMU and NMUR1 expressed on cells, and in vivo studies show that injection of the antibodies is sufficient to suppress NMU levels, leading to enhanced insulin output and glucose handling. The inventors have also shown that the antibodies can also be used as part of a two-way enzyme linked immunosorption assay (ELISA) that is sensitive enough to detect NMU in serum from mice as well as humans.

Methods and compositions are provided for treating an individual in need thereof (e.g., an individual who is obese and/or has diabetes, e.g., type 2 diabetes) by administering an anti-NMU/NMUR agent (e.g., an anti-NMU antibody). For example, methods and compositions are provided for increasing circulating insulin in an individual. Methods and compositions are also provided for detecting neuromedin U (NMU) (e.g., in a biological sample such as serum). Methods and compositions are also provided for predicting whether an individual will develop diabetes, e.g., type 2 diabetes, and/or Pancreatic Ductal Adenocarcinoma (PDAC), and for identifying an individual who would benefit from administration of an anti-NMU/NMUR agent.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

In the description that follows, a number of terms conventionally used in the field are utilized. In order to provide a clear and consistent understanding of the specification and claims, and the scope to be given to such terms, the following definitions are provided.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "recipient", "individual", "subject", "host", and "patient", are used interchangeably herein and refer to any mammalian subject for whom diagnosis, treatment, or therapy is desired (e.g., mice, non-human primates, humans, etc.). "Mammal" for purposes of treatment refers to any animal classified as a mammal, including humans, domestic and farm animals, and zoo, sports, or pet animals, such as dogs, horses, cats, cows, sheep, goats, pigs, etc. In some cases, an individual of a subject method is a mammal. In some embodiments, the mammal is a rodent (e.g., a rat, a mouse), in some cases the mammal is a non-human primate, and in some cases the mammal is a human.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc.

The term "biological sample" encompasses a clinical sample such as blood, plasma, serum, aspirate, and also includes tissue obtained by surgical resection, tissue obtained by biopsy, cells in culture, cell supernatants, cell lysates, tissue samples, organs, bone marrow, and the like. A "biological sample" includes biological fluids derived therefrom (e.g., cancerous cell, infected cell, etc.), e.g., a sample comprising polynucleotides and/or polypeptides that is obtained from such cells (e.g., a cell lysate or other cell extract comprising polynucleotides and/or polypeptides). A biological sample comprising an inflicted cell (e.g., cancer cell, an infected cell, etc.) from a patient can also include non-inflicted cells. In some cases, a biological sample (e.g., one in which an amount/concentration of NMU is measured) is serum. In some such cases, NMU is measured in the serum and not from sub-fractions of the serum. For example, in some cases, NMU is measured in a serum sample that includes exosomes (e.g., a serum sample without or prior to any sub-fractioning to isolate exosomes). In some cases, NMU is measured in a serum sample that does not include exosomes (e.g., in some cases exosomes are removed from (separated from) the serum prior to measuring NMU in the serum).

The term "diagnosis" is used herein to refer to the identification of a molecular or pathological state, disease or condition, such as the identification of a molecular subtype of cancer, the determination that an individual is at risk for developing diabetes, e.g., type 2 diabetes, and the like.

The term "prognosis" is used herein to refer to the prediction of the likelihood of disease progression (e.g., progression to diabetes, progression to cancer, etc.), including recurrence, metastatic spread of cancer, and drug resistance.

The term "prediction" is used herein to refer to the act of foretelling or estimating, based on observation, experience, or scientific reasoning. In one example, a physician may predict whether a patient will become diabetic (e.g., whether an individual who is obese will become diabetic). As another example, one may predict the likelihood that an individual will progress to pancreatic cancer (e.g., predicting whether an individual with pancreatitis will progress to pancreatic cancer, whether the individual will develop PDAC, etc.)

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides/epitopes). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member). Examples of specific binding members include, but are not limited to: agents that specifically bind NMU and/or NMUR1 (e.g., antibodies).

The term "antibody" is used in the broadest sense and specifically covers monoclonal antibodies (including full length monoclonal antibodies), polyclonal antibodies, multispecific antibodies (e.g., bispecific antibodies), and antibody fragments (e.g., Fab fragments) so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., J. Mol. Biol. 186:651 (1985); Novotny and Haber, Proc. Natl. Acad. Sci. U.S.A. 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity. The CDRs of the light chain are referred to as CDR-L1, CDR-L2, and CDR-L3, while the CDRs of the heavy chain are referred to as CDR-H1, CDR-H2, and CDR-H3.

Digestion of antibodies (e.g., with enzymes such as papain, Ficin, and the like) produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in The Pharmacology of Monoclonal Antibodies, vol. 113, Rosenburg and Moore eds., Springer-Verlag, New York, pp. 269-315 (1994).

As would be readily understood by one of ordinary skill in the art, it is noted that designation of the terms "light chain" and "heavy chain" CDRs can be arbitrary, provided that the two halves of the binding site have matched sets of CDRs. As an example, in a scFv, CDR 1, 2, 3 can be on the heavy side or the light side, provided that it is matched with CDR 4, 5, 6 on the opposite chain. Thus, in cases where CDRs are stated to be heavy chain or light chain CDRs. Thus, when a subject anti-NMU antibody or antigen binding region thereof includes a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28, respectively, it is also meant to encompass an anti-NMU antibody or antigen binding region thereof in which the heavy chain CDRs include the amino acid sequences set forth in SEQ ID NOs: 18-20 and the light chain CDRs include the amino acid sequences set forth in SEQ ID NOs: 26-28. Likewise, when a subject anti-NMU antibody or antigen binding region thereof comprises a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12, respectively, it is also meant to encompass an anti-NMU antibody or antigen binding region thereof in which the heavy chain CDRs include the amino acid sequences set forth in SEQ ID NOs: 2-4 and the light chain CDRs include the amino acid sequences set forth in SEQ ID NOs: 10-12.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

There are five major classes of immunoglobulins: IgA, IgD, IgE, IgG, and IgM, and several of these can be further divided into subclasses (isotypes), e.g., IgG$_1$, IgG$_2$, IgG$_3$, IgG$_4$, IgA$_1$, IgA$_2$. The heavy-chain constant domains that correspond to the different classes of immunoglobulins are called a, d, e, g, and m, respectively. The subunit structures and three-dimensional configurations of different classes of immunoglobulins are well known. Engineered variants of immunoglobulin subclasses, including those that increase or decrease immune effector functions, half-life, or serum-stability, are also encompassed by this terminology.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

Unless specifically indicated to the contrary, the term "conjugate" as described and claimed herein is defined as a heterogeneous molecule formed by the covalent attachment of one or more antibody fragment(s) to one or more polymer molecule(s), where the heterogeneous molecule is water soluble, i.e. soluble in physiological fluids such as blood, and wherein the heterogeneous molecule is free of any structured aggregate. A conjugate of interest is PEG. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

As used in this disclosure, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

The word "label" when used herein refers to a detectable compound or composition which is conjugated directly or indirectly, e.g., to a subject anti-NMU/NMUR agent. The label may itself be detectable by itself (directly detectable label) (e.g., radioisotope labels or fluorescent labels), or the label can be indirectly detectable, e.g., in the case of an enzymatic label, the enzyme may catalyze a chemical alteration of a substrate compound or composition and the product of the reaction is detectable.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

Compositions

Provided are compositions and methods for treatment (e.g., for increasing circulating insulin in an individual, for treating an individual who is obese or who has or is at risk of developing diabetes, for treating an individual who has chronic pancreatitis, familial pancreatitis, idiopathic pancreatitis, type 3c diabetes mellitus, cystic fibrosis, late stage pancreatic cancer, and/or cancer cachexia), and for prediction (e.g., predicting whether an individual will develop diabetes, predicting whether an individual will develop PDAC, and/or predicting whether an individual would benefit from administration of an anti-NMU/NMUR agent). A subject method of treatment includes administration of an anti-NMU/NMUR agent (e.g., an anti-NMU antibody or antigen-binding fragment thereof) and a subject method of prediction includes measuring an expression level of neuromedin U (NMU) (e.g., measuring an amount of NMU protein present in a biological sample).

Provided are new anti-NMU antibodies, which are anti-NMU/NMUR agents (e.g., see the Examples below). Human NMU is a 25 amino acid hormone encoded by the gene NMU and produced from a processed pre-prohormone (Mitchell et al., Br J Pharmacol. 2009 September; 158(1): 87-103). NMU is produced in the gastrointestinal tract of humans and other mammals like mice. NMU has no known covalent modifications other than C-terminal amidation (a common feature of circulating peptide hormones), and the newly generated antibodies (C578 and 2A16) were generated against a bioactive form of circulating NMU (FRVDEEFQSPFASQSRGYFLFRPRN-NH$_2$) (SEQ ID NO: 33).

The following amino acid sequences are those of pre-processed human and mouse neuromedin U (NMU) as downloaded from NCB:

Human NMU (Isoform 1) (NP 006672.1)

(SEQ ID NO: 40)
MLRTESCRPRSPAGQVAAASPLLLLLLLLAWCAGACRGAPILPQGLQPEQ

QLQLWNEIDDTCSSFLSIDSQPQASNALEELCFMIMGMLPKPQEQDEKDN

TKRFLFHYSKTQKLGKSNVVSSVVHPLLQLVPHLHERRMKRFRVDEEFQS

PFASQSRGYFLFRPRNGRRSAGFI amino acids of the processed form are bold and underlined Human NMU (Isoform 2) (NP 001278974.1)

(SEQ ID NO: 41)
MLRTESCRPRSPAGQVAAASPLLLLLLLLAWCAGACRGAPILPQGLQPEQ

QLQLWNEASNALEELCFMIMGMLPKPQEQDEKDNTKRFLFHYSKTQKLGK

SNVVSSVVHPLLQLVPHLHERRMKRFRVDEEFQSPFASQSRGYFLFRPRN

GRRSAGFI amino acids of the processed form are bold and underlined

Mouse NMU (NP 062388.1)

(SEQ ID NO: 42)
MSRAAGHRPGLSAGQLAAATASPLLSLLLLLACCADACKGVPISPQRLQP

EQELQLWNEIHEACASFLSIDSRPQASVALRELCRIVMEISQKPQEQSEK

DNTKRFLFHYSKTQKLGNSNVVSSVVHPLLQLVPQLHERRMKRFKAEYQS

PSVGQSKGYFLFRPRNGKRSTSFI amino acids recognized by the antibody C578 are bold and underlined Anti-NMU/NMUR Agent.

NMU (e.g., circulating NMU in the serum) binds to its receptor (NMUR1) on the surface of cells that express NMUR1. An "anti-NMU/NMUR agent" binds to (specifically binds) NMU and/or NMUR1 and inhibits/blocks the interaction between (e.g., reduces the binding between) NMU and NMUR1. This binding leads to decreased NMU signaling.

In some case, an anti-NMU/NMUR agent is an anti-NMU antibody or binding fragment thereof. The inventors have produced two new monoclonal anti-NMU antibodies (referred to herein as "C578" and "2A16"), both of which specifically bind to human NMU (antibody C578 also specifically binds to mouse NMU, i.e., it cross-reacts). Sequence details, including the CDR sequences, and additional information related to the antibodies is presented in FIG. 10.

As such, in some cases, a subject anti-NMU antibody (or antigen binding fragment thereof) includes a light chain comprising a CDR-L1, CDR-L2, and CDR-L3 comprising the amino acid sequences set forth in SEQ ID NOs: 2-4, respectively. In some cases, a subject anti-NMU antibody (or antigen binding fragment thereof) includes a heavy chain comprising a CDR-H1, CDR-H2, and CDR-H3 comprising the amino acid sequences set forth in SEQ ID NOs: 10-12, respectively. In some cases, a subject anti-NMU antibody (or antigen binding fragment thereof) includes a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12, respectively. In some cases, a subject anti-NMU antibody (or antigen binding fragment thereof) includes the antigen binding region (e.g., the CDRs, and in some cases the framework region as well) of the C578 antibody. In some cases, a subject anti-NMU antibody is the C578 antibody. In some cases, a subject anti-NMU antibody is a humanized version of the C578 antibody (e.g., the antibody includes the CDRs of the C578 antibody but is humanized).

In some cases, a subject anti-NMU antibody (or antigen binding fragment thereof) includes a light chain comprising a CDR-L1, CDR-L2, and CDR-L3 comprising the amino acid sequences set forth in SEQ ID NOs: 18-20, respectively. In some cases, a subject anti-NMU antibody (or antigen binding fragment thereof) includes a heavy chain comprising a CDR-H1, CDR-H2, and CDR-H3 comprising the amino acid sequences set forth in SEQ ID NOs: 26-28, respectively. In some cases, a subject anti-NMU antibody (or antigen binding fragment thereof) includes a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28, respectively. In some cases, a subject anti-NMU antibody (or antigen binding fragment thereof) includes the antigen binding region (e.g., the CDRs, and in some cases the framework region as well) of the 2A16 antibody. In some cases, a subject anti-NMU antibody is the 2A16 antibody. In some cases, a subject anti-NMU antibody is a humanized version of the 2A16 antibody (e.g., the antibody includes the CDRs of the 2A16 antibody but is humanized).

The term "NMU-neutralizing antibody" is used herein to mean an antibody (or antigen binding fragment thereof) that reduces that activity of NMU (e.g., an antibody that binds to NMU and blocks the interaction between NMU and its receptor (NMUR1)).

Suitable anti-NMU antibodies (or anti-NMUR1 antibodies) include fully human, humanized or chimeric versions of such antibodies. For example, humanized antibodies are useful for in vivo applications in humans due to their low antigenicity. Similarly caninized, felinized, etc. antibodies are useful for applications in dogs, cats, and other species respectively. Antibodies of interest include humanized antibodies, or caninized, felinized, equinized, bovinized, porcinized, etc., antibodies, and variants thereof. Also envisioned are single chain antibodies derived from camelids, single chain antibodies derived from shark, engineered fibronectin domain-containing proteins, knottin peptides, and DARPins; and fluorophore-conjugated versions of each of these reagents.

In some cases, an anti-NMU antibody (e.g., one that includes the light and heavy chain CDRs of C578 or 2A16) is a humanized antibody (e.g., can be an IgG4 isotype humanized antibody, e.g., an IgG4 isotype antibody having a mutation in the hinge region such as the S241P mutation that reduces heterogeneity sometimes found in chimeric mouse/human IgG4 antibodies)(e.g., see Angal et al., Mol Immunol. 1993 January; 30(1):105-8). In other words, in some cases, an anti-NMU antibody (e.g., one that includes a light chain with CDR-L1, CDR-L2, and CDR-L3 having the amino acid sequences set forth in SEQ ID NOs: 2-4, respectively, and a heavy chain with CDR-H1, CDR-H2, and CDR-H3 having the amino acid sequences set forth in SEQ ID NOs: 10-12, respectively; or one that includes a light chain with CDR-L1, CDR-L2, and CDR-L3 having the amino acid sequences set forth in SEQ ID NOs: 18-20, respectively, and a heavy chain with CDR-H1, CDR-H2, and CDR-H3 having the amino acid sequences set forth in SEQ ID NOs: 26-28, respectively) is a humanized antibody (e.g., can be an IgG4 isotype humanized antibody, e.g., an IgG4 isotype antibody having a mutation in the hinge region such as the S241P mutation that reduces heterogeneity sometimes found in chimeric mouse/human IgG4 antibodies).

In general, humanized antibodies are made by substituting amino acids in the framework regions of a parent non-human antibody to produce a modified antibody that is less immunogenic in a human than the parent non-human antibody. For example, in some cases, antibody humanization involves placing the complementarity determining regions (CDRs) into the 'framework' of a human antibody, leading to production of a chimeric antibody compatible with human in vivo use.

Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated herein are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332.

In some embodiments, therefore, the disclosure provides humanized versions of the above described monoclonal antibodies (e.g., those antibodies that recognize human NMU). For any of the described anti-NMU antibodies, the antibody can be a humanized antibody, a binding fragment thereof (e.g., a Fab fragment), or any permutation having the antigen binding domain (or, e.g., the CDRs of the antigen binding domain). (e.g., see definition of "antibody" above).

In some case, an anti-NMU/NMUR agent is an RNAi agent (e.g., an anti-NMUR1 RNAi agent or an anti-NMU RNAi agent). For example, genetic studies presented in the examples below demonstrate results in mice harboring genetic ablation of NMUR1. Such ablation can be temporarily or permanently mimicked using RNAi agents, e.g., an RNAi agent that targets (e.g., is specific for) NMUR1, or an RNAi agent that targets (e.g., is specific for) NMU.

The term "RNAi agent" is used herein to mean any agent that can be used to induce a gene specific RNA interference (RNAi) response in a cell. Suitable examples of RNAi agents include, but are not limited to short interfering RNAs (siRNAs) and short hairpin RNAs (shRNAs), and micro RNAs (miRNA). An RNAi agent (e.g., shRNA, siRNA, miRNA) specific for NMU is an agent that targets the mRNA encoding the NMU protein. An RNAi agent (e.g., shRNA, siRNA, miRNA) specific for NMUR1 is an agent that targets the mRNA encoding the NMUR1 protein. RNAi agents can readily be designed to specifically target any desired mRNA (e.g., one encoding NMU or NMUR1) by choosing an appropriate nucleotide sequence.

Various RNAi agent designs (RNAi agents with various features) are known in the art and any convenient RNAi agent (e.g., one that targets NMU or one that targets NMUR1) can be used. For example, various designs of RNAi agents (as well as methods of their delivery) can be found in numerous patents, including, but not limited to U.S. Pat. Nos. 7,022,828; 7,176,304; 7,592,324; 7,667,028; 7,718,625; 7,732,593; 7,772,203; 7,781,414; 7,807,650; 7,879,813; 7,892,793; 7,910,722; 7,947,658; 7,973,019; 7,973,155; 7,981,446; 7,993,925; 8,008,271; 8,008,468; 8,017,759; 8,034,922; 8,399,653; 8,415,319; 8,426,675; 8,466,274; 8,524,679; 8,524,679; 8,569,065; 8,569,256; 8,569,258; 9,233,102; 9,233,170; and 9,233,174; all of which are incorporated herein by reference.

Two-Way ELISA Assay (Sandwich ELISA)

Provided are compositions (e.g., kits) and methods for measuring NMU in a sample (e.g., in a blood sample, in a serum sample, in a plasma sample, and the like). In some cases, a subject method of detection is a two-way enzyme-linked immunosorbent assay (two-way ELISA). In some cases, in a subject two-way ELISA, a first antibody is immobilized on a solid surface (e.g., a bead, the surface of a well in a multi-well plate, etc.). The first antibody binds to an antigen (in this case NMU), and then a second antibody is used that also binds to the antigen, but binds to a different region of the antigen than the region to which the first antibody binds. In other words, the first and second antibodies bind to non-overlapping amino acids of NMU.

In some cases, a subject method is a method of detecting NMU, and includes a step of measuring an amount of NMU present in a biological sample using a subject two-way ELISA (e.g., as described here and in the kits below). Such methods include contacting a biological sample (e.g., contacting NMU in the biological sample) with the first and second anti-NMU antibodies, and measuring an amount of the second anti-NMU antibody. For example, in some cases, the method includes (a) contacting a biological sample (e.g., serum sample) with a first anti-NMU antibody, wherein the first anti-NMU antibody is immobilized on a solid surface and NMU of the biological sample binds to the first anti-NMU antibody; (b) contacting the NMU that is bound to the first anti-NMU antibody, with the second anti-NMU antibody; and (c) measuring an amount of the second anti-NMU antibody. In some cases, the method includes a first wash step between steps (a) and (b), and/or performing a second wash step between steps (b) and (c). In some cases the biological sample is a blood sample. In some cases the biological sample is a serum sample. In some cases the biological sample is an aspirate. In some cases the biological sample is a biopsy (e.g., from a biopsy).

In some cases, the second antibody is detectably labeled (e.g., conjugated to an indirectly or directly detectable label). In some cases, the second antibody is not conjugated to a label but is nonetheless detectable (e.g., using secondary antibodies, e.g., if the second antibody is a mouse or a goat antibody, it can be detected using an anti-mouse or anti-goat secondary antibody, respectively).

For the antibody regions discussed below (e.g., CDRs, framework regions, and the like), please refer to FIG. 10 (e.g., for sequence information and SEQ ID NOs.).

In some cases, the first antibody of a subject two-way ELISA includes a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12, respectively. In some cases, the first antibody includes the antigen binding region (e.g., the CDRs, and in some cases the framework region as well) of the C578 antibody. In some cases, the first antibody is the C578 antibody. In some cases, the first antibody is a humanized version of the C578 antibody (e.g., the antibody includes the CDRs of the C578 antibody but is humanized).

In some cases, the first antibody includes a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28, respectively. In some cases, the first antibody includes the antigen binding region (e.g., the CDRs, and in some cases the framework region as well) of the 2A16 antibody. In some cases, the first antibody is the 2A16 antibody. In some cases, the first antibody is a humanized version of the 2A16 antibody (e.g., the antibody includes the CDRs of the 2A16 antibody but is humanized).

In some cases, the second antibody includes a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12, respectively. In some cases, the second antibody includes the antigen binding region (e.g., the CDRs, and in some cases the framework region as well) of the C578 antibody. In some cases, the second antibody is the C578 antibody. In some cases, the second antibody is a humanized version of the C578 antibody (e.g., the antibody includes the CDRs of the C578 antibody but is humanized).

In some cases, the second antibody includes a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28, respectively. In some cases, the second antibody includes the antigen binding region (e.g., the CDRs, and in some cases the framework region as well) of the 2A16 antibody. In some cases, the second antibody is the 2A16 antibody. In some cases, the second antibody is a humanized version of the 2A16 antibody (e.g., the antibody includes the CDRs of the 2A16 antibody but is humanized).

In some cases, the first antibody includes a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12, respectively; and the second antibody includes a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28, respectively. In some cases, the first antibody includes a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28, respectively; and the second antibody includes a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12, respectively. In some cases, the first antibody includes the antigen binding region (e.g., the CDRs, and in some cases the framework region as well) of the C578 antibody; and the second antibody includes the antigen binding region (e.g., the CDRs, and in some cases the framework region as well) of the 2A16 antibody; or visa versa. In some cases, the first antibody is the C578 antibody; and the second antibody is the 2A16 antibody; or visa versa. In some cases, the first antibody is a humanized version of the C578 antibody (e.g., the antibody includes the CDRs of the C578 antibody but is humanized), and the second antibody is a humanized version of the 2A16 antibody (e.g., the antibody includes the CDRs of the 2A16 antibody but is humanized); or visa versa.

As such, in some cases, one of the first and second antibodies includes a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12, respectively; and the other of the first and second antibodies includes a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28, respectively. In some cases, one of the first and second antibodies includes the antigen binding region (e.g., the CDRs, and in some cases the framework region as well) of the C578 antibody; and the other of the first and second antibodies includes the antigen binding region (e.g., the CDRs, and in some cases the framework region as well) of the 2A16 antibody. In some cases, one of the first and second antibodies is the C578 antibody; and the other of the first and second antibodies is the 2A16 antibody. In some cases, one of the first and second antibodies is a humanized version of the C578 antibody (e.g., the antibody includes the CDRs of the C578 antibody but is humanized), and the other of the first and second antibodies is a humanized version of the 2A16 antibody (e.g., the antibody includes the CDRs of the 2A16 antibody but is humanized).

In some cases, a subject kit is a kit for measuring NMU in a sample (e.g., in a blood sample, in a serum sample, in a plasma sample, and the like). In some cases, a subject kit includes a first anti-NMU antibody and a second anti-NMU antibody, where one of the first and second anti-NMU antibodies includes (i) a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12, respectively; or (ii) a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28, respectively.

In some cases, a subject kit includes a first anti-NMU antibody and a second anti-NMU antibody, where one of the first and second anti-NMU antibodies includes a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12, respectively; and the other of the first and second anti-NMU antibodies includes a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28, respectively.

In some cases, a subject kit includes a first anti-NMU antibody and a second anti-NMU antibody, where one of the first and second anti-NMU antibodies includes (i) the antigen binding region (e.g., the CDRs, and in some cases the framework region as well) of the C578 antibody; or (ii) the antigen binding region (e.g., the CDRs, and in some cases the framework region as well) of the 2A16 antibody. In some cases, a subject kit includes a first anti-NMU antibody and a second anti-NMU antibody, where one of the first and second anti-NMU antibodies includes the antigen binding region (e.g., the CDRs, and in some cases the framework region as well) of the C578 antibody; and the other of the first and second anti-NMU antibodies includes the antigen binding region (e.g., the CDRs, and in some cases the framework region as well) of the 2A16 antibody.

In some cases, a subject kit includes a first anti-NMU antibody and a second anti-NMU antibody, where one of the first and second anti-NMU antibodies is (i) the C578 antibody; or (ii) the 2A16 antibody. In some cases, a subject kit includes a first anti-NMU antibody and a second anti-NMU antibody, where one of the first and second anti-NMU antibodies is the C578 antibody; and the other of the first and second anti-NMU antibodies is the 2A16 antibody.

In some cases, one or both of the first and second anti-NMU antibodies are humanized (e.g., a humanized version of the C578 antibody and/or a humanized version of the 2A16 antibody). In some cases, the first anti-NMU antibody is immobilized on a solid surface (e.g., on the surface of a well of a multi-well plate, on the surface of a bead, etc.). In some cases, the second anti-NMU antibody is labeled (e.g., indirectly labeled and/or directly labeled, e.g., conjugated to an indirectly detectable label such as an enzyme, conjugated to a directly detectable label such as a fluorophore or a fluorescent protein, and the like).

In some cases, a subject two-way ELISA assay can detect (e.g., is used to detect) NMU in a sample, where the NMU is present at a concentration in a range of from 0.02 to 50 ng/mL (e.g., 0.02 to 40 ng/ml, 0.02 to 30 ng/ml, 0.02 to 25 ng/ml, 0.02 to 20 ng/ml, 0.02 to 15 ng/ml, 0.05 to 50 ng/ml, 0.05 to 40 ng/ml, 0.05 to 30 ng/ml, 0.05 to 25 ng/ml, 0.05 to 20 ng/ml, 0.05 to 15 ng/ml, 0.1 to 50 ng/ml, 0.1 to 40 ng/ml, 0.1 to 30 ng/ml, 0.1 to 25 ng/ml, 0.1 to 20 ng/ml, 0.1 to 15 ng/ml, 0.2 to 50 ng/ml, 0.2 to 40 ng/ml, 0.2 to 30 ng/ml, 0.2 to 25 ng/ml, 0.2 to 20 ng/ml, or 0.2 to 15 ng/ml). In some cases, a subject two-way ELISA assay can detect (e.g., is used to detect) NMU in a sample, where the NMU is present at a concentration in a range of from 0.1 to 20 ng/ml.

Methods

Prediction Methods

Provided are prediction methods (e.g. predicting whether an individual will develop diabetes, predicting whether an individual will develop PDAC or pancreatitis, predicting whether an individual is in need of therapy using an anti-NMU/NMUR agent, i.e., identifying an individual who would benefit from administration of an anti-NMU/NMUR agent). Provided are diagnostic methods (e.g. predicting whether an individual has diabetes, predicting/determining whether an individual has PDAC or pancreatitis, predicting whether an individual has type 3c diabetes mellitus (T3cDM), predicting whether an individual is in need of therapy using an anti-NMU/NMUR agent, i.e., identifying an individual who would benefit from administration of an anti-NMU/NMUR agent).

In some embodiments, a subject method is a method of predicting (e.g., predicting that an individual will develop diabetes), and the method includes measuring NMU (e.g., using a two-way ELISA as described above). As such, in some embodiments, a subject method includes detecting (e.g., measuring an amount of) NMU in sample (e.g., a biological sample such as a blood sample, serum sample, tumor sample, etc.). In some cases, NMU is measured via two-way ELISA (e.g., as described above). In some cases, a measuring step (to measure NMU) is performed after a provocation step such as an overnight fast, a glucose challenge (e.g., an oral bolus of glucose), etc Because the prediction and diagnostic methods are based on a measured expression level of NMU (protein and/or RNA) in a sample, the prediction methods include a step of measuring, e.g., measuring an expression level of an NMU expression product in a biological sample from an individual (e.g., measuring a protein expression level, i.e., the amount of NMU in a sample; measuring an mRNA expression level, i.e., the amount of mRNA encoding NMU in a sample). Thus, the present disclosure provides compositions for measuring neuromedin U (NMU) in a sample (e.g., a biological sample such as a blood sample, a serum sample, a biopsy, etc.).

A biomarker is a molecular entity (e.g., an expression product such as mRNA, protein, etc.) whose representation in a sample correlates (either positively or negatively) with a particular state. For example, an expression level of NMU (protein) in the serum correlates with whether an individual is likely to develop diabetes. As demonstrated in the examples of the present disclosure, the inventors have identified NMU as a biomarker positively associated with increased likelihood that a given individual will develop diabetes (e.g., type 2 Diabetes (T2DM)). For example, an increased level of NMU in the serum is predictive that an individual will develop diabetes. In some cases, the individual is suspected of having an increased risk of developing diabetes (e.g., the individual has a family history of diabetes, is overweight, and/or is obese) prior to the measuring step. In some cases, a subject method includes (a) measuring an expression level of NMU (e.g., mRNA, protein) in a biological sample from an individual (e.g., a blood sample, a biopsy, a serum sample), (b) determining that the measured expression level of NMU is greater than or equal to a reference value; and (c) predicting that the individual will develop diabetes. In some cases, the measuring step is performed using an anti-NMU antibody (or fragment thereof) disclosed herein. In some cases, the measuring step is performed using a two-way ELISA disclosed herein.

In some cases, NMU can be used as a biomarker positively associated with increased likelihood that a given individual will develop PDAC. In some cases, the individual is suspected of having an increased risk of developing PDAC (e.g., the individual may have a family history of PDAC, may have pancreatitis, may already have diabetes, etc.). As such in some cases, a subject method includes (a) measuring an expression level of NMU (e.g., mRNA, protein) in a biological sample from an individual (e.g., a blood sample, a biopsy), (b) determining that the measured expression level of NMU is greater than or equal to a reference value; and (c) predicting that the individual will develop PDAC. In some cases, the measuring step is performed using an anti-NMU antibody (or fragment thereof) disclosed herein. In some cases, the measuring step is performed using a two-way ELISA disclosed herein.

In some cases, NMU can be used as a biomarker positively associated with increased likelihood that a given individual will develop PDAC or pancreatitis (e.g., recurrent acute pancreatitis and/or chronic pancreatitis). In some cases, the individual is suspected of having an increased risk of developing PDAC or pancreatitis (e.g., recurrent acute pancreatitis and/or chronic pancreatitis) (e.g., the individual may have a family history of PDAC or pancreatitis). As such in some cases, a subject method includes (a) measuring an expression level of NMU (e.g., mRNA, protein) in a biological sample from an individual (e.g., a blood sample, a biopsy), (b) determining that the measured expression level of NMU is greater than or equal to a reference value; and (c) predicting that the individual will develop PDAC or pancreatitis (e.g., recurrent acute pancreatitis and/or chronic pancreatitis). In some cases, the measuring step is performed using an anti-NMU antibody (or fragment thereof) disclosed herein. In some cases, the measuring step is performed using a two-way ELISA disclosed herein.

In some cases, NMU can be used as a biomarker positively associated with increased likelihood that a given individual will be responsive to (e.g., is in need of) administration of a subject anti-NMU/NMUR agent (e.g., an anti-NMU antibody). In some cases, the individual is suspected of being an individual will be responsive to (e.g., is in need of) administration of a subject anti-NMU/NMUR agent (e.g., an anti-NMU antibody) (e.g., in some cases, the individual is overweight, obese, has diabetes, has type 2 diabetes, has type 3c diabetes, has PDAC, has recurring acute pancreatitis, has chronic pancreatitis, and/or has cancer cachexia. As such in some cases, a subject method includes (a) measuring an amount of NMU present in a blood sample from an individual (e.g., a serum sample), (b) determining that the amount of NMU present in the blood sample is greater than or equal to a reference value (e.g., see below); and (c) predicting that the individual would benefit from administration of an anti-NMU/NMUR agent. In some cases, the measuring step is performed using an anti-NMU antibody (or fragment thereof) disclosed herein. In some cases, the measuring step is performed using a two-way ELISA disclosed herein.

The terms "assaying" and "measuring" are used herein to include the physical steps of manipulating a biological sample (e.g., blood sample, serum sample, cell sample, biopsy, and the like) to generate data related to a sample (e.g., measuring an expression level in a biological sample).

In practicing the subject methods, the expression level of a NMU expression product (e.g., mRNA, protein) can be measured (e.g., the expression level in a cell, in a population of cells, in a biological sample from an individual, and the like). The expression level(s) can be measured by any convenient method. For example, an RNA expression level can be measured by measuring the levels/amounts of one or more nucleic acid transcripts, e.g. mRNAs, of NMU. Protein expression levels of NMU can be detected by measuring the levels/amounts of the NMU protein (e.g., using a two-way ELISA disclosed herein). In some cases, measuring is performed using an anti-NMU antibody (or fragment thereof) disclosed herein. In some cases, the measuring step is performed using a two-way ELISA disclosed herein.

"Measuring" can be used to determine whether the measured expression level is less than, greater than, "less than or equal to", or "greater than or equal to" a particular threshold, (the threshold can be pre-determined or can be determined by assaying a control sample), such as a reference value. Measuring can mean determining a quantitative value (using any convenient metric) that represents the level of expression (i.e., expression level, e.g., the amount of protein and/or RNA, e.g., mRNA) of a particular expression product (e.g., a NMU expression product). The level of expression can be expressed in arbitrary units associated with a particular assay (e.g., fluorescence units, e.g., mean fluorescence intensity (MFI), threshold cycle ($C_t$), quantification cycle ($C_q$), and the like), or can be expressed as an absolute value with defined units (e.g., number of mRNA transcripts, number of protein molecules, concentration of protein, etc.).

An expression level (i.e., level of expression) can be a raw measured value, or can be a normalized and/or weighted value derived from the raw measured value. The terms "expression level" and "measured expression level" are used herein to encompass raw measured values as well as values that have manipulated in some way (e.g., normalized and/or weighted). In some cases, a normalized expression level is a measured expression level of an expression product from a sample where the raw measured value for the expression product has been normalized. For example, the expression level of an expression product (e.g., an RNA encoding NMU, a NMU protein) can be compared to the expression level of one or more other expression products (e.g., the expression level of a housekeeping gene/protein, the averaged expression levels of multiple genes/proteins, etc.) to derive a normalized value that represents a normalized expression level. Methods of normalization will be known to one of ordinary skill in the art and any convenient normalization method can be used. The specific metric (or units) chosen is not crucial as long as the same units are used (or conversion to the same units is performed) when evaluating multiple markers and/or multiple biological samples (e.g., samples from multiple individuals or multiple samples from the same individual).

Measuring Protein

An expression level of an expression product (e.g., an expression product of NMU) may be measured by detecting (e.g., in a cell extract, in a fixed cell, in living cell, in a biological sample, in a blood sample, in a serum sample, etc.) the amount or level of one or more proteins (e.g., NMU) or a fragment thereof. For measuring a protein level, the amount or level of protein the sample (e.g., in a cell extract, in a fixed cell, in living cell, in a biological sample, in a blood sample, in a serum sample, etc.) is determined. In some instances, the concentration of one or more additional proteins may also be measured, and the measured expression level compared to the level of the one or more additional proteins to provide a normalized value for the measured expression level. In some embodiments, the measured expression level is a relative value calculated by comparing the level of one protein relative to another protein. In other embodiments the concentration is an absolute measurement (e.g., weight/volume or weight/weight).

The expression level of a protein (e.g., NMU) may be measured by detecting in a sample the amount or level of one or more proteins/polypeptides or fragments thereof. The terms "polypeptide," "peptide" and "protein" are used interchangeably herein to refer to a polymer of amino acid residues. "Polypeptide" refers to a polymer of amino acids (amino acid sequence) and does not refer to a specific length of the molecule. Thus peptides and oligopeptides are included within the definition of polypeptide. In some cases, cells and/or exosomes are removed from a biological sample (e.g., via centrifugation, via adhering cells to a dish or to plastic, etc.) prior to measuring the expression level (e.g., measuring in a serum sample from which exosomes have been removed).

When protein levels are to be detected, any convenient protocol for measuring protein levels may be employed. Examples of methods for assaying protein levels include but are not limited to enzyme-linked immunosorbent assay (ELISA) (e.g., a two-way ELISA as disclosed herein), mass spectrometry, proteomic arrays, xMAP™ microsphere technology, flow cytometry, western blotting, immunohistochemistry, and the like. In some cases, an anti-NMU antibody described herein is used for measuring a level of NMU protein in a sample (e.g., a serum sample).

Some protein detection methods are antibody-based methods (e.g., a subject two-way ELISA). The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

Measuring RNA

An expression level of an expression product (e.g., an expression product of NMU) may be measured by detecting (e.g., in a cell extract, in a fixed cell, in a living cell, in a biological sample, in a biopsy sample, etc.) the amount or level of one or more RNA transcripts or a fragment thereof encoded by the gene of interest (NMU). For measuring RNA levels, the amount or level of an RNA in the sample is determined, e.g., the expression level of an mRNA. In some instances, the expression level of one or more additional RNAs may also be measured, and the level of biomarker expression compared to the level of the one or more additional RNAs to provide a normalized value for the biomarker expression level.

The expression level of nucleic acids in the sample may be detected using any convenient protocol. A number of exemplary methods for measuring RNA (e.g., mRNA) expression levels (e.g., expression level of a nucleic acid biomarker) in a sample are known by one of ordinary skill in the art, such as those methods employed in the field of differential gene expression analysis, and any convenient method can be used. Exemplary methods include, but are not limited to: hybridization-based methods (e.g., Northern blotting, array hybridization (e.g., microarray); in situ hybridization; in situ hybridization followed by FACS; and the like)(Parker & Barnes, Methods in Molecular Biology 106: 247-283 (1999)); RNAse protection assays (Hod, Biotechniques 13:852-854 (1992)); PCR-based methods (e.g., reverse transcription PCR (RT-PCR), quantitative RT-PCR (qRT-PCR), real-time RT-PCR, etc.)(Weis et al., Trends in Genetics 8:263-264 (1992)); nucleic acid sequencing methods (e.g., Sanger sequencing, Next Generation sequencing (i.e., massive parallel high throughput sequencing, e.g., Illumina's reversible terminator method, Roche's pyrosequencing method (454), Life Technologies' sequencing by ligation (the SOLiD platform), Life Technologies' Ion Torrent platform, single molecule sequencing, etc.); nanopore based sequencing methods; and the like.

In some embodiments, the biological sample can be assayed directly. In some embodiments, nucleic acid of the biological sample is amplified (e.g., by PCR) prior to assaying. As such, techniques such as PCR (Polymerase Chain Reaction), RT-PCR (reverse transcriptase PCR), qRT-PCR (quantitative RT-PCR, real time RT-PCR), etc. can be used prior to the hybridization methods and/or the sequencing methods discussed above.

As noted above, gene expression in a sample can be detected using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis.

Hybridization to arrays may be performed, where the arrays can be produced according to any suitable methods known in the art. For example, methods of producing large arrays of oligonucleotides are described in U.S. Pat. Nos. 5,134,854, and 5,445,934 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505.

Methods for collection of data from hybridization of samples with an array are also well known in the art. For example, the polynucleotides of the cell samples can be generated using a detectable fluorescent label, and hybridization of the polynucleotides in the samples detected by scanning the microarrays for the presence of the detectable label. Methods and devices for detecting fluorescently marked targets on devices are known in the art. Generally, such detection devices include a microscope and light source for directing light at a substrate. A photon counter detects fluorescence from the substrate, while an x-y translation stage varies the location of the substrate. A confocal detection device that can be used in the subject methods is described in U.S. Pat. No. 5,631,734. A scanning laser microscope is described in Shalon et al., *Genome Res.* (1996) 6:639. A scan, using the appropriate excitation line, is performed for each fluorophore used. The digital images generated from the scan are then combined for subsequent analysis. For any particular array element, the ratio of the fluorescent signal from one sample is compared to the fluorescent signal from another sample, and the relative signal intensity determined.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes.

One representative and convenient type of protocol for measuring mRNA levels is array-based gene expression profiling. Such protocols are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively.

Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions, and unbound nucleic acid is then removed. The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

The resultant pattern of hybridized nucleic acid provides information regarding expression for each of the genes that have been probed, where the expression information is in terms of whether or not the gene is expressed and, typically, at what level, where the expression data, i.e., expression profile (e.g., in the form of a transcriptosome), may be both qualitative and quantitative. Pattern analysis can be performed manually, or can be performed using a computer program. Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992.

Alternatively, non-array based methods for quantitating the level of one or more nucleic acids in a sample may be employed. These include those based on amplification protocols, e.g., Polymerase Chain Reaction (PCR)-based assays, including quantitative PCR, reverse-transcription PCR (RT-PCR), real-time PCR, quantitative RT-PCR (qRT-PCR), and the like, e.g. TaqMan® RT-PCR, SYBR green; MassARRAY® System, BeadArray® technology, and Luminex technology; and those that rely upon hybridization of probes to filters, e.g. Northern blotting and in situ hybridization. Other non-amplified methods of analysis include digital bar-coding, e.g. NanoString nCounter Analysis System which is a digital color-coded barcode technology based on direct multiplexed measurement of gene expression. The technology uses molecular "barcodes" and single molecule imaging to detect and count hundreds of unique transcripts in a single reaction. Each color-coded barcode is attached to a single target-specific probe corresponding to a gene of interest. Mixed together with controls, they form a multiplexed CodeSet.

Examples of some of the nucleic acid sequencing methods listed above are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39); Soni et al Clin Chem 53: 1996-2001 2007; and Morozova (Genomics. 2008 92:255-64), which are incorporated by reference for the general descriptions of the methods and the particular steps of the methods, including starting products, reagents, and final products for each of the steps.

For measuring mRNA levels, the starting material can be RNA or poly A+ RNA (e.g., isolated from a biological sample, from a suspension of cells, etc.). General methods for mRNA extraction are known in the art and are disclosed in standard textbooks of molecular biology, including Ausubel et al., Current Protocols of Molecular Biology, John Wiley and Sons (1997). RNA isolation (e.g., mRNA isolation) can be performed using any convenient protocol. For example, RNA isolation can be performed using a purification kit, buffer set and protease from commercial manufacturers, according to the manufacturer's instructions. For example, RNA from cell suspensions can be isolated using Qiagen RNeasy mini-columns, and RNA from cell suspensions or homogenized tissue samples can be isolated using the TRIzol reagent-based kits (Invitrogen), MasterPure™ Complete DNA and RNA Purification Kit (EPICENTRE™, Madison, Wis.), Paraffin Block RNA Isolation Kit (Ambion, Inc.) or RNA Stat-60 kit (Tel-Test).

Reference Value

A measured NMU expression level (e.g., NMU protein, NMU encoding mRNA) can be determined in a number of different ways. For example, in some cases, a NMU expression level is measured in a sample (e.g., the concentration of NMU in sample such as serum sample is measured) and is compared to a reference value.

In some cases, the expression level (e.g., the number of transcripts, the concentration of NMU protein in a sample, and the like) of an NMU expression product (e.g., RNA, protein) in a biological sample from an individual who is predicted to develop diabetes, PDAC, and/or pancreatitis is greater than a reference value (e.g., an expression level of an NMU expression product in one or more biological samples from one or more control individuals who do not have diabetes, PDAC, and/or pancreatitis; a value, e.g., an average, derived from the expression level of an NMU expression product in a biological sample from multiple control individuals who do not have diabetes, PDAC, and/or pancreatitis; etc.).

For example, the expression level (e.g., the concentration of protein, the number of transcripts, the concentration of NMU protein in a sample, and the like) of an NMU expression product (e.g., RNA, protein) in a biological sample from an individual who is predicted to develop diabetes, PDAC, and/or pancreatitis can be 1.1-fold or more (e.g., 1.2-fold or more, 1.3-fold or more, 1.4-fold or more, 1.5-fold or more, 2-fold or more, 2.5-fold or more, 3-fold or more, 4-fold or more, 5-fold or more, 7.5-fold or more, or 10-fold or more) greater than a reference value (e.g., an expression level of an NMU expression product in one or more biological samples from one or more control individuals who do not have diabetes, PDAC, and/or pancreatitis; a value, e.g., an average, derived from the expression level of an NMU expression product in a biological sample from multiple control individuals who do not have diabetes, PDAC, and/or pancreatitis; etc.).

In some cases, the expression level (e.g., the number of transcripts, the concentration of NMU protein in a sample, and the like) of an NMU expression product (e.g., RNA, protein) in a biological sample from an individual who would benefit from administration of a subject anti-NMU/NMUR agent (e.g., an anti-NMU antibody) is greater than a reference value (e.g., an expression level of an NMU expression product in one or more biological samples from one or more control individuals who are not in need of (or who would not benefit from) administration of a subject anti-NMU/NMUR agent (e.g., an anti-NMU antibody), e.g., an average, derived from the expression level of an NMU expression product in a biological sample from multiple control individuals who are not in need of (or who would not benefit from) administration of a subject anti-NMU/NMUR agent (e.g., an anti-NMU antibody)).

For example, the expression level (e.g., the concentration of protein, the number of transcripts, the concentration of NMU protein in a sample, and the like) of an NMU expression product (e.g., RNA, protein) in a biological sample from an individual who would benefit from administration of a subject anti-NMU/NMUR agent (e.g., an anti-NMU antibody) can be 1.1-fold or more (e.g., 1.2-fold or more, 1.3-fold or more, 1.4-fold or more, 1.5-fold or more, 2-fold or more, 2.5-fold or more, 3-fold or more, 4-fold or more, 5-fold or more, 7.5-fold or more, or 10-fold or more) greater than a reference value (e.g., an expression level of an NMU expression product in one or more biological samples from one or more control individuals who are not in need of (or who would not benefit from) administration of a subject anti-NMU/NMUR agent (e.g., an anti-NMU antibody), e.g., an average, derived from the expression level of an NMU expression product in a biological sample from multiple control individuals who are not in need of (or who would not benefit from) administration of a subject anti-NMU/NMUR agent (e.g., an anti-NMU antibody)).

In some cases, the predicting and/or diagnosing is based on a measured expression level of NMU (e.g., protein, mRNA) in combination with one or more clinical measurements (e.g., a meal tolerance test (MTT), patient weight, an insulin measurement, a test of insulin sensitivity, a measure of glucose level, etc.).

Generating a Report

In some cases, a subject method (e.g., any of the screening methods described above) includes a step of generating a report (e.g., a report that the test agent is a candidate agent for treating obesity and/or diabetes).

A "report," as described herein, is an electronic or tangible document which includes report elements that provide information of interest relating to the results and/or assessments of such results of a subject method (e.g., a prediction and/or diagnostic method). In some embodiments, a subject report includes a measured expression level as discussed in greater detail above (e.g., a raw value, a normalized value, a normalized and weighted value, etc.) (e.g., an expression level of a NMU expression product such as a NMU protein expression level and/or a NMU-encoding mRNA expression level). In some embodiments, a subject report includes a NMU expression level. In some cases, a subject report includes an assessment (e.g. a determination of whether an NMU expression product such as an NMU protein or NMU encoding mRNA is elevated in a sample, e.g., relative to a reference value).

A subject report can be completely or partially electronically generated. A subject report can include one or more of: 1) the assay used to measure the NMU expression level (e.g., a subject two-way ELISA); 2) raw data; 3) details of how an expression level was calculated from raw data; 4) a value associated with whether (and if so how much) a NMU expression level is elevated relative to a reference; 5) information about the biological sample tested; 6) information about the individual from whom the biological sample was collected; and the like. Thus, the subject methods may include a step of generating or outputting a report, which report can be provided in the form of an electronic medium (e.g., an electronic display on a computer monitor), or in the form of a tangible medium (e.g., a report printed on paper or other tangible medium). Any form of report may be provided.

It will also be readily appreciated that the reports can include additional elements or modified elements. For example, where electronic, the report can contain hyperlinks which point to internal or external databases which provide more detailed information about selected elements of the report. When in electronic format, the report is recorded on a suitable physical medium, such as a computer readable medium, e.g., in a computer memory, zip drive, CD, DVD, etc.

Treatment Methods

In some embodiments, a subject method is a treatment method (e.g., using an anti-NMU/NMUR agent, e.g., as described above). For example in some cases, a subject method is a method of treating an individual in need thereof (e.g., an individual with elevated NMU levels, e.g., serum NMU levels). In some cases, a subject method is a method of increasing circulating insulin in an individual. In some cases, the individual has diabetes, or is suspected of having an increased risk of developing diabetes (e.g., the individual is obese and/or has a family history that includes diabetics). In some cases, the individual has a disease selected from: cystic fibrosis, familial pancreatitis, idiopathic pancreatitis, chronic pancreatitis, PDAC, type 3c diabetes mellitus, type 2 diabetes, late stage pancreatic cancer, and cancer cachexia.

Treatment methods provided herein include a step of administering an anti-NMU/NMUR agent (e.g., an anti-NMU antibody, an RNAi agent that targets NMUR1) to an individual. Details related to suitable anti-NMU/NMUR agents can be found above.

For example, any of the above discussed anti-NMU antibodies can be used as an anti-NMU/NMUR agent. Thus, in some cases, a subject anti-NMU antibody (or antigen binding fragment thereof) includes a light chain comprising a CDR-L1, CDR-L2, and CDR-L3 comprising the amino acid sequences set forth in SEQ ID NOs: 18-20, respectively. In some cases, a subject anti-NMU antibody (or antigen binding fragment thereof) includes a heavy chain comprising a CDR-H1, CDR-H2, and CDR-H3 comprising the amino acid sequences set forth in SEQ ID NOs: 26-28, respectively. In some cases, a subject anti-NMU antibody (or antigen binding fragment thereof) includes a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28, respectively. In some cases, a subject anti-NMU antibody (or antigen binding fragment thereof) includes the antigen binding region (e.g., the CDRs, and in some cases the framework region as well) of the 2A16 antibody. In some cases, a subject anti-NMU antibody is the 2A16 antibody. In some cases, a subject anti-NMU antibody is a humanized version of the 2A16 antibody (e.g., the antibody includes the CDRs of the 2A16 antibody but is humanized).

As such, in some cases, a subject humanized anti-NMU antibody (or antigen binding fragment thereof) includes a light chain comprising a CDR-L1, CDR-L2, and CDR-L3 comprising the amino acid sequences set forth in SEQ ID NOs: 18-20, respectively. In some cases, a subject humanized anti-NMU antibody (or antigen binding fragment thereof) includes a heavy chain comprising a CDR-H1, CDR-H2, and CDR-H3 comprising the amino acid sequences set forth in SEQ ID NOs: 26-28, respectively. In some cases, a subject humanized anti-NMU antibody (or antigen binding fragment thereof) includes a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28, respectively. In some cases, a subject humanized anti-NMU antibody (or antigen binding fragment thereof) includes the antigen binding region (e.g., the CDRs, and in some cases the framework region as well) of the 2A16 antibody. In some cases, a subject humanized anti-NMU antibody is the 2A16 antibody. In some cases, a subject humanized anti-NMU antibody is a humanized version of the 2A16 antibody (e.g., the antibody includes the CDRs of the 2A16 antibody but is humanized).

In some cases, a subject anti-NMU antibody (or antigen binding fragment thereof) includes a light chain comprising a CDR-L1, CDR-L2, and CDR-L3 comprising the amino acid sequences set forth in SEQ ID NOs: 2-4, respectively. In some cases, a subject anti-NMU antibody (or antigen binding fragment thereof) includes a heavy chain comprising a CDR-H1, CDR-H2, and CDR-H3 comprising the amino acid sequences set forth in SEQ ID NOs: 10-12, respectively. In some cases, a subject anti-NMU antibody (or antigen binding fragment thereof) includes a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12, respectively. In some cases, a subject anti-NMU antibody (or antigen binding fragment thereof) includes the antigen binding region (e.g., the CDRs, and in some cases the framework region as well) of the C578 antibody. In some cases, a subject anti-NMU antibody is the C578 antibody. In some cases, a subject anti-NMU antibody is a humanized version of the C578 antibody (e.g., the antibody includes the CDRs of the C578 antibody but is humanized).

As such, in some cases, a subject humanized anti-NMU antibody (or antigen binding fragment thereof) includes a light chain comprising a CDR-L1, CDR-L2, and CDR-L3 comprising the amino acid sequences set forth in SEQ ID NOs: 2-4, respectively. In some cases, a subject humanized anti-NMU antibody (or antigen binding fragment thereof) includes a heavy chain comprising a CDR-H1, CDR-H2, and CDR-H3 comprising the amino acid sequences set forth in SEQ ID NOs: 10-12, respectively. In some cases, a subject humanized anti-NMU antibody (or antigen binding fragment thereof) includes a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12, respectively. In some cases, a subject humanized anti-NMU antibody (or antigen binding fragment thereof) includes the antigen binding region (e.g., the CDRs, and in some cases the framework region as well) of the C578 antibody. In some cases, a subject humanized anti-NMU antibody is the C578 antibody. In some cases, a subject humanized anti-NMU antibody is a humanized version of the C578 antibody (e.g., the antibody includes the CDRs of the C578 antibody but is humanized).

Formulations

An anti-NMU/NMUR agent (e.g., an anti-NMU antibody) can be prepared as a dosage unit, with a pharmaceutically acceptable excipient, with pharmaceutically acceptable salts and esters, etc. Compositions can be provided as pharmaceutical compositions.

Pharmaceutical Compositions.

Suitable anti-NMU/NMUR agents (e.g., one or more anti-NMU antibodies) can be provided in pharmaceutical compositions suitable for therapeutic use, e.g. for human treatment. In some embodiments, pharmaceutical compositions of the present disclosure include one or more therapeutic entities of the present disclosure (e.g., one or more anti-NMU antibodies) and can include a pharmaceutically acceptable carrier, a pharmaceutically acceptable salt, a pharmaceutically acceptable excipient, and/or esters or solvates thereof. In some embodiments, the use of an anti-NMU/NMUR agent (e.g., anti-NMU antibody) includes use in combination with another therapeutic agent (e.g., another agent for preventing or treating diabetes, preventing, controlling, or treating obesity, preventing or treating a cancer such as PDAC, and the like). Therapeutic formulations comprising an anti-NMU/NMUR agent (e.g., an anti-NMU antibody) can be prepared by mixing the agent(s) having the desired degree of purity with a physiologically acceptable carrier, a pharmaceutically acceptable salt, an excipient, and/or a stabilizer (Remington's Pharmaceutical Sciences 16th edition, Osol, A. Ed. (1980)) (e.g., in the form of lyophilized formulations or aqueous solutions). A composition having an anti-NMU/NMUR agent (e.g., an anti-NMU antibody) can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with obesity, diabetes, pancreatic cancer, PDAC, etc.) as well as those in which prevention is desired (e.g., those with increased susceptibility to diabetes and/or cancer such as PDAC, etc.).

A therapeutic treatment is one in which the subject is inflicted (e.g., has the disease) prior to administration and a prophylactic treatment is one in which the subject is not yet inflicted (does not yet have the disease) prior to administration. In some embodiments, the subject has an increased likelihood of becoming inflicted or is suspected of being inflicted prior to treatment. In some embodiments, the subject is suspected of having an increased likelihood of becoming inflicted. For example, in some cases, the individual is obese, has a family history of obesity and/or diabetes, has a family history of pancreatic cancer such as PDAC, etc.

A "therapeutically effective dose" or "therapeutic dose" is an amount sufficient to effect desired clinical results (i.e., achieve therapeutic efficacy), e.g., increased insulin output. A therapeutically effective dose can be administered in one or more administrations. For purposes of this disclosure, a therapeutically effective dose of an anti-NMU/NMUR agent (e.g., an anti-NMU antibody) is an amount that is sufficient to palliate, ameliorate, stabilize, reverse, prevent, slow or delay the progression of the disease state (e.g., diabetes, obesity, PDAC). Thus, in some cases, a therapeutically effective dose of an anti-NMU/NMUR agent (e.g., an anti-NMU antibody) reduces the binding of circulating NMU to its receptor on the surface of cells at an effective dose for increasing insulin output in an individual.

A single therapeutically effective dose or a series of therapeutically effective doses would be able to achieve a desired result in an individual (e.g., increase circulating level of insulin). A therapeutically effective dose of an anti-NMU/NMUR agent (e.g., an anti-NMU antibody) can depend on the specific agent used, and in some cases can be 0.5 mg/kg body weight or more (e.g., 1 mg/kg or more, 2 mg/kg or more, 3 mg/kg or more, 4 mg/kg or more, 5 mg/kg or more, 6 mg/kg or more, 7 mg/kg or more, 8 mg/kg or more, 9 mg/kg or more, 10 mg/kg or more, 15 mg/kg or more, 20 mg/kg or more, 25 mg/kg or more, 30 mg/kg or more, 35 mg/kg or more, or 40 mg/kg or more) for each agent.

In some cases, a therapeutically effective dose of an anti-NMU/NMUR agent (e.g., an anti-NMU antibody) can be in a range of from 0.5 mg/kg to 100 mg/kg (e.g., from 0.5 to 90 mg/kg, from 0.5 to 90 mg/kg, from 0.5 to 80 mg/kg, from 0.5 to 70 mg/kg, from 0.5 to 60 mg/kg, from 0.5 to 50 mg/kg, from 0.5 to 40 mg/kg, from 0.5 to 30 mg/kg, from 0.5 to 20 mg/kg, from 0.5 to 10 mg/kg, from 1 to 100 mg/kg, from 1 to 90 mg/kg, from 1 to 90 mg/kg, from 1 to 80 mg/kg, from 1 to 70 mg/kg, from 1 to 60 mg/kg, from 1 to 50 mg/kg, from 1 to 40 mg/kg, from 1 to 30 mg/kg, from 1 to 20 mg/kg, from 1 to 10 mg/kg, from 3 to 100 mg/kg, from 3 to 90 mg/kg, from 3 to 90 mg/kg, from 3 to 80 mg/kg, from 3 to 70 mg/kg, from 3 to 60 mg/kg, from 3 to 50 mg/kg, from 3 to 40 mg/kg, from 3 to 30 mg/kg, from 3 to 20 mg/kg, from 3 to 10 mg/kg, from 5 to 100 mg/kg, from 5 to 90 mg/kg, from 5 to 90 mg/kg, from 5 to 80 mg/kg, from 5 to 70 mg/kg, from 5 to 60 mg/kg, from 5 to 50 mg/kg, from 5 to 40 mg/kg, from 5 to 30 mg/kg, from 5 to 20 mg/kg, from 5 to 10 mg/kg, from 10 to 100 mg/kg, from 10 to 90 mg/kg, from 10 to 90 mg/kg, from 10 to 80 mg/kg, from 10 to 70 mg/kg, from 10 to 60 mg/kg, from 10 to 50 mg/kg, from 10 to 40 mg/kg, from 10 to 30 mg/kg, from 10 to 20 mg/kg, from 20 to 100 mg/kg, from 20 to 90 mg/kg, from 20 to 90 mg/kg, from 20 to 80 mg/kg, from 20 to 70 mg/kg, from 20 to 60 mg/kg, from 20 to 50 mg/kg, from 20 to 40 mg/kg, or from 20 to 30 mg/kg) for each agent.

In some cases, a therapeutically effective dose of an anti-NMU/NMUR agent (e.g., an anti-NMU antibody) can be in a range of from 5 mg/kg to 50 mg/kg (e.g., from 5 to 40 mg/kg, from 5 to 30 mg/kg, from 5 to 20 mg/kg, from 10 to 50 mg/kg, from 10 to 40 mg/kg, from 10 to 30 mg/kg, or from 10 to 20 mg/kg) for each agent. In some cases, a therapeutically effective dose of an anti-NMU/NMUR agent (e.g., an anti-NMU antibody) can be in a range of from 10 mg/kg to 40 mg/kg (e.g., from 10 to 35 mg/kg, or from 10 to 30 mg/kg) for each agent.

The dose required to achieve a desired result can be proportional to the amount of time between doses and inversely proportional to the number of doses administered. Thus, as the frequency of dosing increases, the required dose decreases. The optimization of dosing strategies will be readily understood and practiced by one of ordinary skill in the art.

Dosage and frequency may vary depending on the half-life of the anti-NMU/NMUR agent (e.g., an anti-NMU antibody) in the patient. It will be understood by one of skill in the art that such guidelines will be adjusted for the molecular weight of the active agent, e.g. in the use of antibody fragments, in the use of antibody conjugates, in the use of RNAi agents, etc. The dosage may also be varied for localized administration, e.g. intranasal, inhalation, etc., or for systemic administration, e.g. i.m., i.p., i.v., and the like.

Co-Administration

Two of the above described anti-NMU antibodies can be co-administered, and antibody-based NMU inhibition could be readily combined with standard therapies for diseases like obesity and diabetes. As such, in some cases, a subject anti-NMU/NMUR agent (e.g., an anti-NMU antibody) is co-administered with another agent, e.g., a second anti-NMU/NMUR agent, or co-administered with another therapy for obesity and/or diabetes. The terms "co-administration", "co-administer", and "in combination with" include the administration of two or more therapeutic agents (e.g., two or more anti-NMU/NMUR agents such as two different anti-NMU antibodies, an anti-NMU antibody and an RNAi agent that targets NMUR1, an anti-NMU/NMUR agent and an agent for treating diabetes, etc.) either simultaneously, concurrently or sequentially within no specific time limits. In one embodiment, the agents are present in the cell or in the subject's body (in their blood stream) at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

In some cases, a subject an anti-NMU/NMUR agent (e.g., an anti-NMU antibody) (e.g., formulated as a pharmaceutical composition) is co-administered with a obesity and/or diabetes therapeutic drug, a therapeutic drug to treat a cancer such as PDAC, and the like. Such administration may involve concurrent (i.e. at the same time), prior, or subsequent administration of the drug/antibody with respect to the administration of an agent or agents of the disclosure. A person of ordinary skill in the art would have no difficulty determining the appropriate timing, sequence and dosages of administration for particular drugs and compositions of the present disclosure.

An anti-NMU/NMUR agent (e.g., an anti-NMU antibody) need not be, but is optionally formulated with one or more agents that potentiate activity, or that otherwise increase the therapeutic effect. These are generally used in the same dosages and with administration routes as used herein or from 1 to 99% of the employed dosages. In some embodiments, treatment is accomplished by administering a combination (co-administration) of a subject anti-NMU/NMUR agent and an agent that treats obesity. In some embodiments, treatment is accomplished by administering a combination (co-administration) of a subject anti-NMU/NMUR agent and an agent that treats diabetes. In some embodiments, treatment is accomplished by administering a combination (co-administration) of a subject anti-NMU/NMUR agent and an agent that treats a cancer such as PADC. Thus, also envisioned herein are compositions (and methods that use the compositions) that include: (a) an anti-NMU/NMUR agent (e.g., an anti-NMU antibody); and (b) at least one of: (i) an agent used for treatment of diabetes, (ii) an agent used for treatment of obesity, and (iii) an agent used for treatment of cancer, e.g., PDAC.

Delivery

An anti-NMU/NMUR agent (e.g., an anti-NMU antibody) can be administered by any suitable means (e.g., systemic or local), including topical, oral, parenteral, intravenous, intrapulmonary, and intranasal. Parenteral infusions include intramuscular, intravenous (bollus or slow drip), intraarterial, intraperitoneal, intrathecal or subcutaneous administration. An anti-NMU/NMUR agent (e.g., an anti-NMU antibody) can be administered in any manner which is medically acceptable. This may include injections (e.g., by parenteral routes such as intravenous, intravascular, intraarterial, subcutaneous, intramuscular, intratumor, intraperitoneal, intraventricular, or intraepidural), or others as well as oral, nasal, ophthalmic, rectal, or topical. Sustained release administration is also specifically included in the disclosure, by such means as depot injections or erodible implants.

As noted above, an anti-NMU/NMUR agent (e.g., an anti-NMU antibody) can be formulated with a pharmaceutically acceptable carrier (one or more organic or inorganic ingredients, natural or synthetic, with which a subject agent is combined to facilitate its application). A suitable carrier includes sterile saline although other aqueous and non-aqueous isotonic sterile solutions and sterile suspensions known to be pharmaceutically acceptable are known to those of ordinary skill in the art. An "effective amount" refers to that amount which is capable of ameliorating or delaying progression of the diseased, degenerative or damaged condition. In some cases, an effective amount is an amount that brings about a rise in circulating insulin levels in the individual. An effective amount can be determined on an individual basis and will be based, in part, on consideration of the symptoms to be treated and results sought. An effective amount can be determined by one of ordinary skill in the art employing such factors and using no more than routine experimentation.

An anti-NMU/NMUR agent (e.g., an anti-NMU antibody) is often administered as a pharmaceutical composition comprising an active therapeutic agent and another pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In some embodiments, pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

A carrier may bear the agents in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. A carrier may also bear an anti-NMU/NMUR agent (e.g., an anti-NMU antibody) by non-covalent associations, such as non-covalent bonding or by encapsulation. The nature of the carrier can be either soluble or insoluble for purposes of the disclosure. Those skilled in the art will know of other suitable carriers for binding anti-NMU/NMUR agents (e.g., one or more anti-NMU antibodies), or will be able to ascertain such, using routine experimentation.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethyl-benzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Compositions can be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the anti-NMU/NMUR agents (e.g., one or more anti-NMU antibodies) can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in further optimizing and/or defining a therapeutic dosage range and/or a sub-therapeutic dosage range (e.g., for use in humans). The exact formulation, route of administration and dosage can be chosen by the individual physician in view of the patients condition.

In some cases, a method treating an individual (e.g., one who is obese and/or has diabetes), includes, as described elsewhere herein, predicting whether an individual will benefit from such treatment (e.g., measuring an expression level of NMU, such as NMU protein in a biological sample such as serum from the individual, and determining whether the individual will benefit, where those with an increased NMU level, e.g., relative to a reference value, will benefit).

Evaluation Steps (Verify/Evaluate/Monitor Steps)

In addition to increasing insulin output, administration of a subject anti-NMU antibody can enhance output of crucial incretin hormones like glucagon-like peptide-1 (GLP-1) and gastric inhibitory peptide (GIP), further enhancing glucose regulation. Thus, in some cases, a subject method is a method of increasing GLP-1 and/or GIP; decreasing glucagon; and/or decreasing glucose level(s).

In some cases, a subject method (e.g. a treatment method) includes, after administration of an anti-NMU/NMUR agent to an individual (e.g., an anti-NMU antibody), a step of measuring one or more features of the individual (e.g., to verify that the agent produces a desired outcome). Suitable features that can be measured include, but are not limited to: insulin level (e.g., an amount of circulating insulin); blood glucose level; an expression level of GLP-1 (e.g., GLP-1 protein) and/or GIP (e.g., GIP protein); glucagon level; glucose tolerance; body fat mass; patient weight; a response to an overnight fast; a meal tolerance test (MTT); and the like. In some cases, such measurements can be made after a provocation (e.g., an overnight fast; a glucose challenge, a meal tolerance test (MTT), etc.).

In some cases, a subject method (e.g., a method of predicting, a treatment method, etc.) includes a step of measuring one or more of: insulin level (e.g., an amount of circulating insulin); blood glucose level; an expression level of GLP-1 (e.g., GLP-1 protein) and/or GIP (e.g., GIP protein); glucagon level; glucose tolerance; body fat mass; patient weight; a response to an overnight fast; a meal tolerance test (MTT); and the like. In some cases, such measuring can be used as an evaluation/monitoring step to test whether a treatment method (e.g., a method that includes administration of an anti-NMU/NMUR agent such as an anti-NMU antibody or fragment thereof) has produced the desired outcome. In some cases, such measurements can be made after a provocation (e.g., an overnight fast; a glucose challenge, a meal tolerance test (MTT), etc.).

In some cases, such measuring can be used as part of a prediction method (e.g., a method of predicting whether an individual will develop Diabetes, PDAC, and/or pancreatitis; a method of identifying an individual that would benefit from therapy with an anti-NMU/NMUR agent; etc.). For example, one can take into account an amount of measured NMU as well as an amount of measured insulin, glucagon, GLP-1, GIP, and/or glucose when formulating a prediction. In some cases, such measurements can be made after a provocation (e.g., an overnight fast; a glucose challenge, a meal tolerance test (MTT), etc.).

The invention now being fully described, it will be apparent to one of ordinary skill in the art that various changes and modifications can be made without departing from the spirit or scope of the invention.

Experimental

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXAMPLES

Example 1: Two-Way ELISA

A two-way enzyme-linked immunosorption assay (ELISA) was built to measure either human or mouse neuromedin U (NMU) using two newly made monoclonal antibodies (C578 and 2A16). Mouse hybridoma lines were generated that secrete monoclonal antibodies that bind human NMU. These antibodies were used to build the two-way ELISA, one for NMU capture and a separate one for detection. This assay permitted fast and sensitive detection directly from human serum or plasma.

Human NMU is a 25 amino acid hormone encoded by the gene NMU and produced from a processed pre-prohormone (Mitchell et al., Br J Pharmacol. 2009 September; 158(1):

87-103). NMU is produced in the gastrointestinal tract of humans and other mammals like mice. NMU has no known covalent modifications other than C-terminal amidation (a common feature of circulating peptide hormones), and the newly generated antibodies (C578 and 2A16) were generated against a bioactive form of circulating NMU. Two mouse hybridoma lines (C578 and 2A16) producing monoclonal antibodies that bind NMU at picomolar affinity were generated, and CDR sequences were obtained from these cells (e.g., to produce humanized versions of the antibodies) (See FIG. 10 for sequence information). The anti-NMU antibodies were used to build a two-way ELISA that can measure NMU in serum samples (e.g., in mouse serum and in human serum).

NMU potently suppresses pancreatic islet secretion of insulin and also suppresses gastrointestinal secretion of the incretin hormones GLP-1 and GIP. NMU also stimulates secretion of the islet hormone glucagon. Insulin, incretins and glucagon are each fundamental regulators of metabolism in humans. Thus, identifying NMU functions in metabolism and gastrointestinal physiology was focused on. This has led to the discovery that NMU levels are consistently elevated in metabolic disorders like obesity and diabetes (e.g., see data presented in the other examples below). The two way-ELISA assay for measuring human NMU disclosed herein has revealed increased circulating NMU levels in pathological states like obesity and pancreas cancer in humans (e.g., see examples below). This two-way ELISA provides several clear advantages over existing technology, which use a 'one-way' competitive ELISA requiring NMU binding to a single 'capture' antibody, competition with a prefabricated NMU standard linked to biotin, and subsequent detection of biotin with avidin-conjugated peroxidase. The one-way competitive ELISA takes a longer assay time (>5 hours) and requires sample concentration steps that introduce significant variability. Moreover, the currently available assay fails to measure NMU in serum samples. Thus, it has been (erroneously) reported previously that NMU does not circulate (Mitchell et al., Br J Pharmacol. 2009 September; 158(1):87-103).

Obesity and Type 2 Diabetes Mellitus

Consistent with NMU signaling suppressing insulin output in vivo, compensatory increases of insulin and GLP-1 were found in mice with diet-induced obesity (DIO) or genetic insulin resistance (mutant db/db mice), and were accompanied by reduced serum NMU levels. However, with advancing age, these mice develop a well-recognized but poorly-understood beta-cell failure, accompanied by reduced insulin secretion, reduced serum insulin levels and impaired glucose control. These changes were strikingly accompanied by increased serum NMU levels. Glucose intolerance was eliminated and insulin output enhanced in these older obese mice with NMU antibody injection, or by genetic NMU signaling blockade.

These findings identify obesity as a pathological state accompanied by NMU excess, are supported by the finding that serum NMU levels were increased in obese humans (FIG. 4A), and support the view that NMU antibodies can ameliorate metabolic consequences of obesity in vivo. Thus, NMU regulation may be impaired in subsets of obese humans, and elevated NMU levels are a biomarker of susceptibility to complications of obesity, including impaired glucose tolerance and frank diabetes mellitus. Moreover, these findings suggest that attenuation of NMU signaling by antibody blockade in humans (e.g., obese humans) can ameliorate or reverse complications of obesity including impaired insulin output, hyperglycemia or frank diabetes mellitus.

Other common but poorly understood human disease states may reflect NMU excess, including diabetes in lean subjects (as observed in Asians, the elderly, and chronic pancreatitis), or refractory hyperglycemia after bariatric surgery. Thus, prospective measures of NMU levels and regulation may permit a new kind of disease stratification, and identify patient subsets who may be responsive to targeted NMU signaling attenuation using agents like NMU-neutralizing antibodies.

Antibody-based reduction of NMU signaling has possible therapeutic applications in a potentially large group of subjects with excessive systemic NMU signaling or levels. Our studies show NMU elevation in (1) patients with pre-diabetes states like obesity or with established diabetes, (2) patients recognized to have 'lean' diabetes, including subjects with advanced age (>60 y.o.), exocrine pancreas diseases like cystic fibrosis, familial or idiopathic pancreatitis, or the recently recognized 'type 3c' diabetes mellitus, (3) patients with advanced cancer states, like late stage pancreatic cancer and a debilitating complication called cancer cachexia.

Chronic Pancreatitis, Type 3c Diabetes Mellitus and Cancer

Epidemiological studies show that chronic pancreatitis is linked to increased risk of diabetes mellitus and pancreas cancer. Using archived human samples, we have now discovered that NMU is mis-produced in areas of cell metaplasia in a subset of human pancreatitis (without detectable adenocarcinoma), and that serum levels of NMU are elevated in pancreatitis and significantly further elevated in PDAC (e.g., see examples below). Thus, NMU production can be used as a biological marker of cell metaplasia (pre-cancer) and diabetes risk in the pancreas. Because NMU both circulates and has biological activity (suppresses insulin and incretin secretion, promotes glucagon secretion), NMU excess in pancreatitis, or early stage pancreas cancer could promote a form of diabetes called 'type 3c.' Thus, NMU may be a long-sought molecular link between diabetes and pancreas cancer.

Two-Way ELISA

Using the two-way ELISA disclosed herein, mouse Nmu and human NMU were detected in a range of from 0.1 to 20 ng/mL. Serum NMU levels were increased in humans with increasing BMI (FIG. 4A), an association that is statistically significant. In mice and humans without known disease, an approximately 20-fold range of NMU levels in serum was observed. The mechanisms underlying increased serum NMU levels in obesity remain unclear. This may reflect a response to suppress feeding (e.g., NMU over-expression in mice can induce hypophagia). Alternately, this may reflect pathological mechanisms leading to inappropriate NMU secretion.

Example 2

Figure 1E:
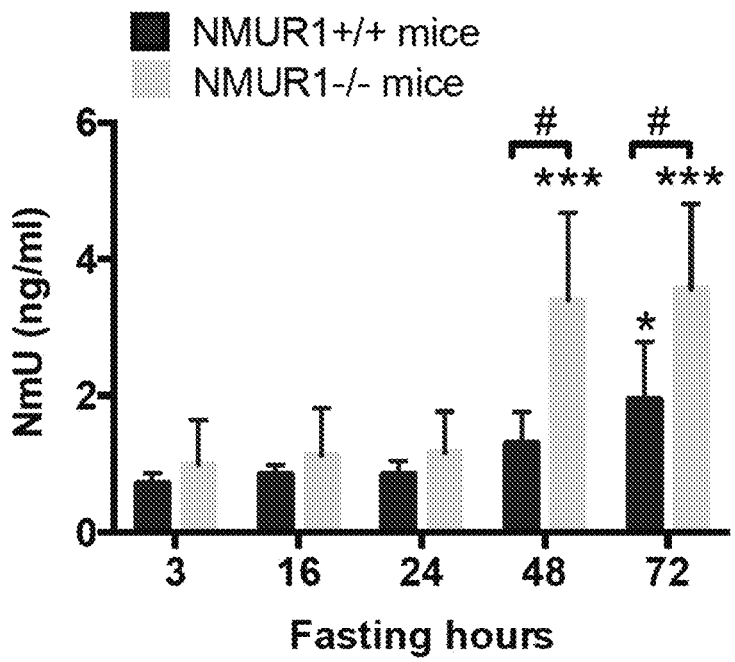

FIG. 1A-1E: Physiological Dynamics of Human and Mouse NMU In Vivo Revealed by Nmu ELISA Assays.

neuromedin U (NMU) is the mammalian ortholog of limostatin, a starvation-induced peptide hormone identified in the fruit fly *Drosophila*. NMU is an enteroendocrine hormone that regulates human insulin output by acting through its receptor, NMUR1, expressed on pancreatic beta-cells (Alfa et al., Cell Metab. 2015 Feb. 3; 21(2):323-33). Consistent with this view, while circulating glucose (FIG. 1A) and insulin (FIG. 1B) levels decrease during prolonged fasting in a human subject, NMU signaling is increased as reflected by elevation of circulating NMU levels in human (FIG. 1C) and mice (FIG. 1D) fasted for up to 72 hours. Loss of peripheral NMU signaling in mice lacking NMUR1 induced an additional accumulation of NMU in plasma of mice fasted for 48 and 72 hours (FIG. 1E). Thus, NMU signaling in fasting is conserved. In addition, these data demonstrate that the two-way ELISA assay (and kit) described herein is a new tool that can measure NMU in vivo in the serum of humans and mice. The two-way ELISA assay used in the experiments of this figure included the antibodies C578 and 2A16 (both of which are described herein).

FIG. 2A-2F: Evidence that NMU Suppresses Post-Prandial Output in Humans and Mice.

Human serum insulin levels rise rapidly by 30 minutes after oral glucose challenge, then fall over the ensuing 150 minutes (FIG. 2A), leading to glucose disposal. By contrast human NMU levels rapidly decreased by 30 minutes after oral glucose challenge, then gradually increased over the next 150 minutes (FIG. 2B), demonstrating reciprocal regulation of these two hormones upon enteral nutrient intake. In mice, circulating NMU levels were increased within 30 minutes after a meal tolerance test (MTT) and reached a maximum peak at 120 minutes. Then the NMU levels remained high in a plateau and returned back to basal levels within 5 h post meal challenge (FIG. 2C). It was confirmed that 30 minutes after an oral bolus of glucose, plasma NMU levels increase (FIG. 2D) whereas an intraperitoneal bolus of glucose did not trigger serum NMU dynamics, demonstrating that the secretion of decretin hormone is regulated by nutrient sensing mechanisms in gastrointestinal tract (FIG. 2E). Mice were subjected to serial oral glucose challenges leading to expected dynamic insulinemic and glycemic responses. NMU levels were significantly higher in the systemic circulation of mice at 30 minutes after the first oral glucose challenged and stayed in a plateau. Upon second glucose challenge at 60 minutes, rapid reduction of NMU levels was observed in plasma within 2 minutes followed by a sustained NMU increase for at least 4 hours (FIG. 2F). Thus, circulating NMU levels are acutely regulated in the post-prandial setting. In both humans and mice, oral glucose challenge can induce an initial fall then a sustained rise of NMU serum levels. These excursions are reciprocal to the rise then fall of serum insulin.

FIG. 3A-3F: In Vivo Loss of NMUR1 Signaling Pathway Improves Glucose Clearance During Prolonged Fasting.

Figure 3A:
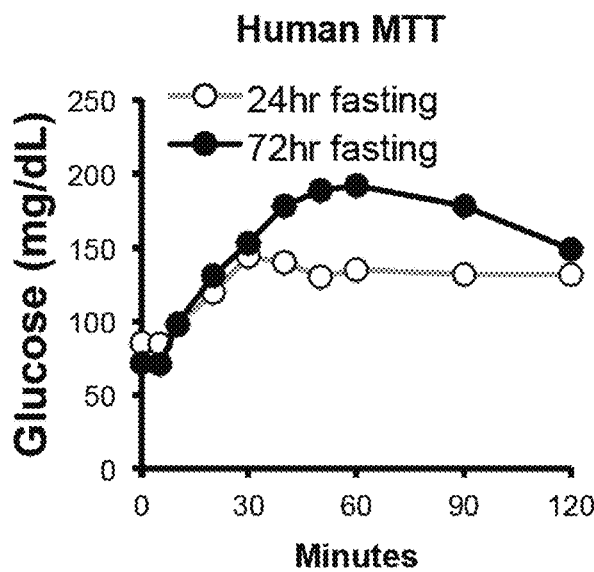
FIG. 3A-3F. Depicts data related to in vivo loss of NMUR1 signaling pathway improving glucose clearance during prolonged fasting.
Figure 3B:
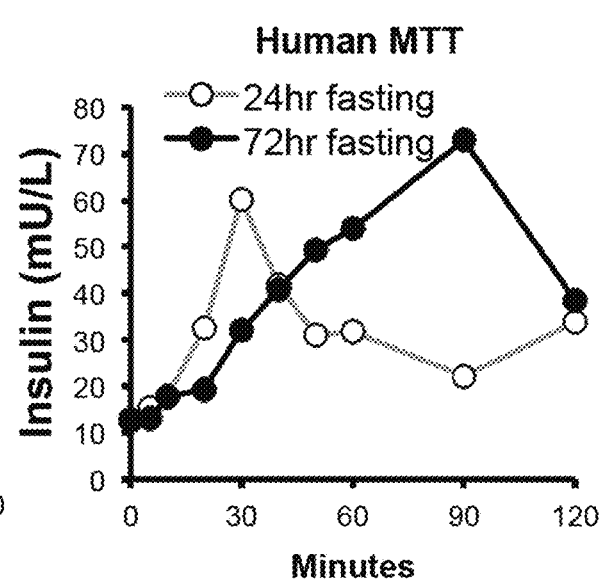
Figure 3C:
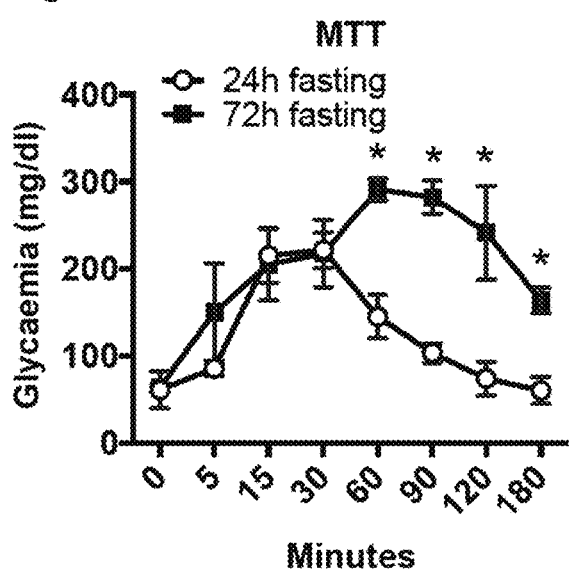
Figure 3D:
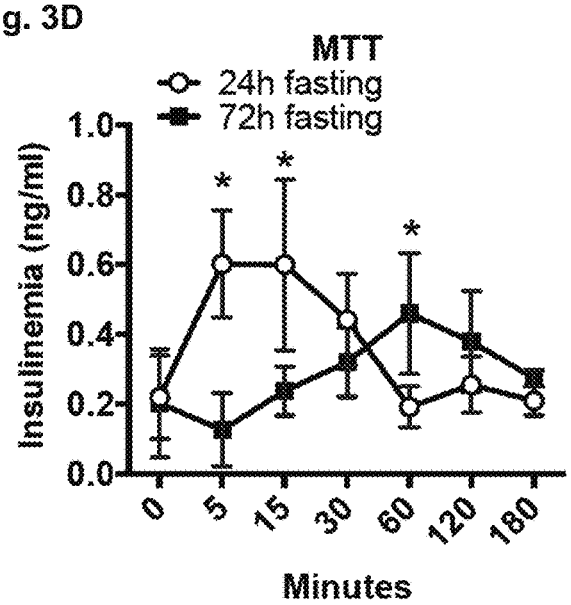
Figure 3E:
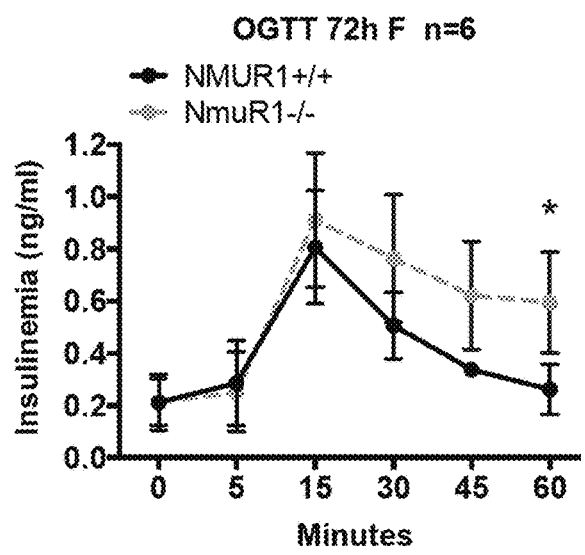
Figure 3F:
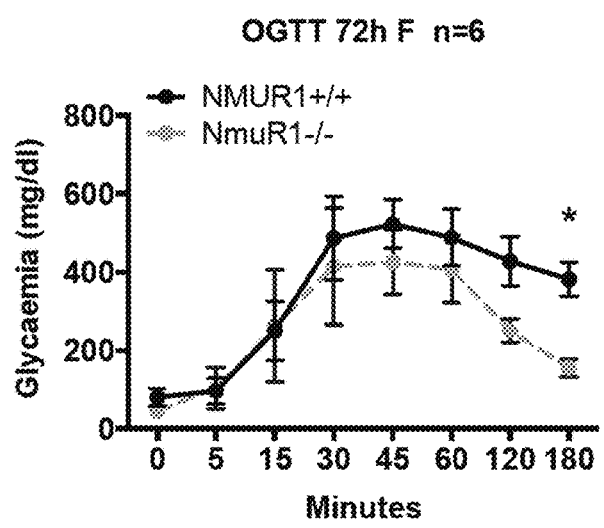

After prolonged fasting, refeeding has been shown to lead to starvation diabetes as was observed in fasted humans (FIGS. 3A-B) and mice (FIGS. 3C-D) challenged with glucose or meal. In mice and humans 72 hour fasting induced a right shift of insulin excursion and significant hyperglycemia (FIGS. 3A-D). To determine the significance of NMU during fasting, NMUR1 mutant mice were generated which lack NMU receptor 1. Fasted NMUR1−/− mutant mice challenged with an oral glucose bolus, displayed a higher insulin response and a better glucose clearance (FIGS. 3E-F). Thus, deletion of NMUR1 signaling prevented starvation diabetes. Thus, in vivo attenuation of NMU signaling improved glucose tolerance and insulin output to prevent diabetes.

Figure 4A:
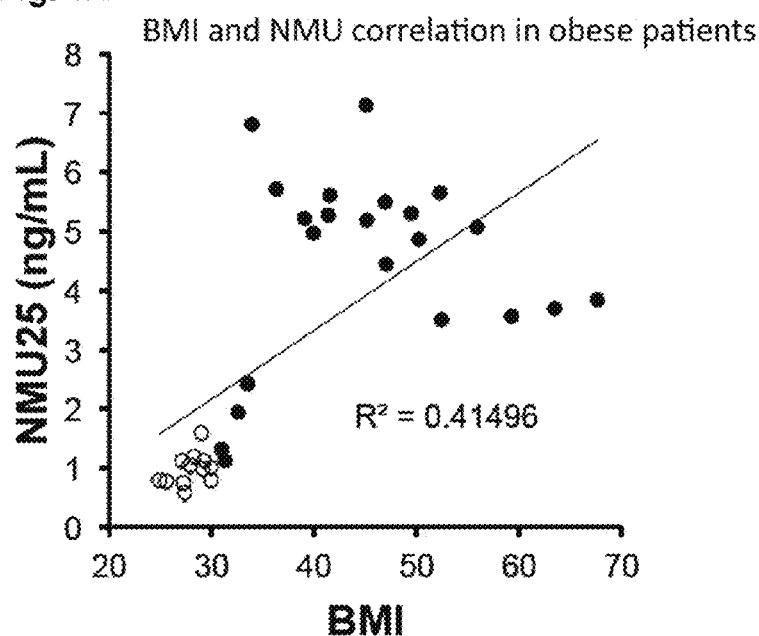
FIG. 4A-4C. Depicts data related to NMU dynamics in the pathological setting of obesity.
Figure 4B:
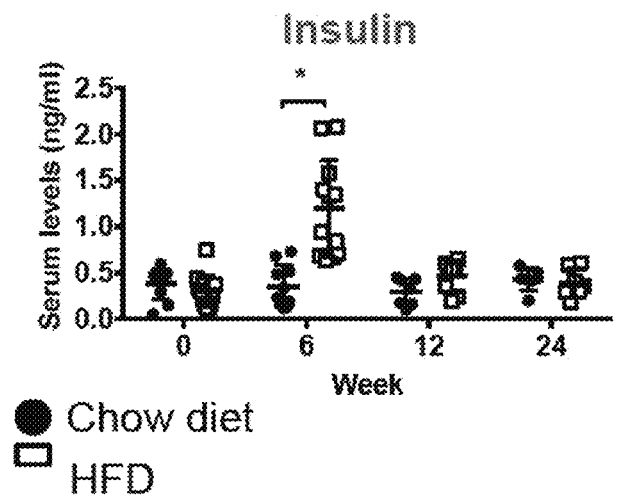
Figure 4C:
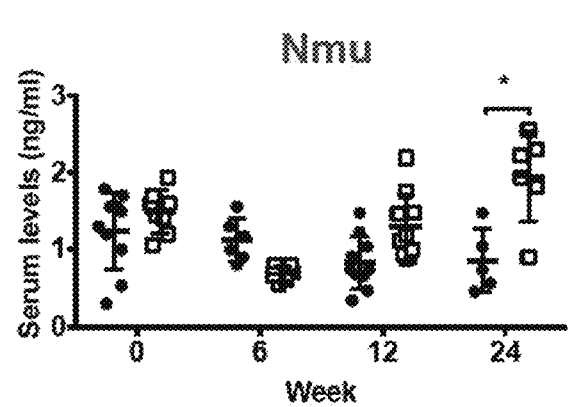

FIG. 4A-4C: NMU Dynamics in the Pathological Setting of Obesity.

Obese and pre-diabetic human subjects often develop relative insulin deficiency and glucose intolerance. Given the data presented here from mice and humans that correlate NMU with reduced insulin excursion, it was hypothesized that NMU might be dysregulated in obesity and pre-diabetic states associated with glucose intolerance. Serum NMU levels were increased in obese humans (FIG. 4A, BMI>30, $R^2$=0.41, P<0.001). Diet-induced obesity from high fat diet (HFD) challenge in mice is accompanied by a compensatory hyperinsulinemia lasting 6-10 weeks. In that period, circulating NMU levels were reduced (FIG. 4B). After 12-24 weeks of HFD, plasma NMU levels increased significantly while basal insulin levels were no longer high (FIG. 4C) and wildtype animals displayed impaired glucose clearance in response to an oral glucose challenge.

FIG. 5A-5C: Loss of NMU Signaling In Vivo Improves Metabolism in Obesity.

Null mutant mice lacking NMUR1 were more prone to gain weight when fed a high-fat diet compared to wild type mice (FIG. 5A). However, NMUR1 genetic deletion in diet-induced obese mice improved insulin excursion and glucose tolerance in response to a glucose challenge (FIG. 5B-C). Thus in obesity states, NMU signaling attenuation improves insulin output and glucose control.

FIG. 6A-6E: NMU is a Novel Regulator of GLP1 and GIP.

Figure 6A:
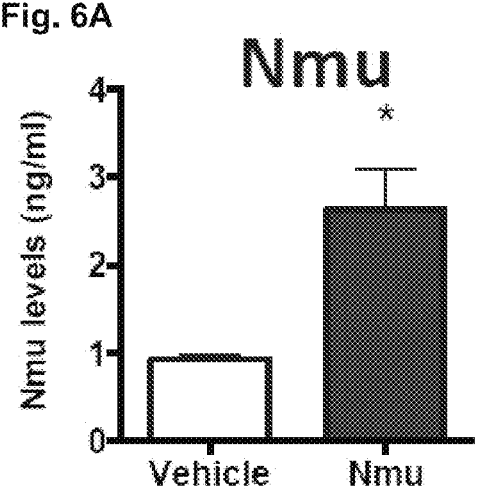
FIG. 6A-6E. Depicts data related to NMU as a novel regulator of GLP1 and GIP.
Figure 6B:
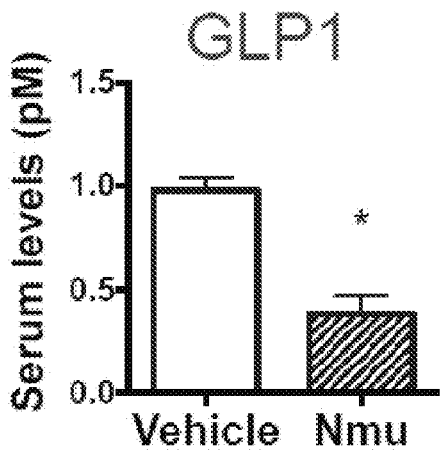
Figure 6C:
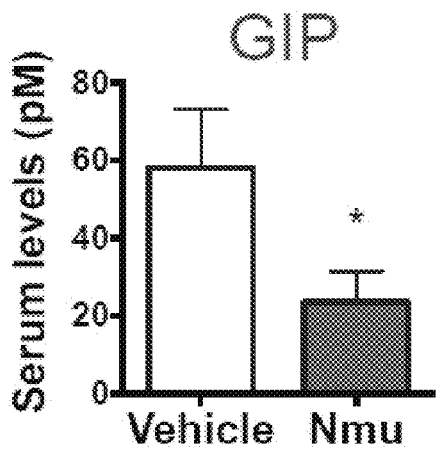
Figure 6D:
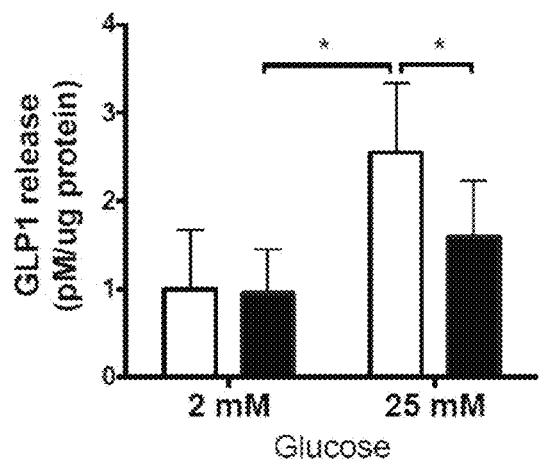
Figure 6E:
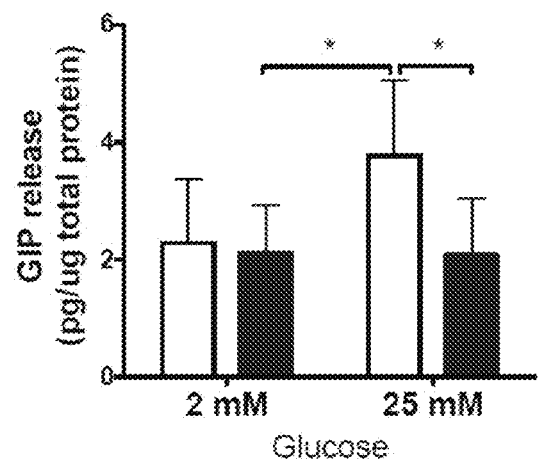

The increased circulating levels of NMU observed in mice during fasting were reproduced with a single intraperitoneal dose of NMU (FIG. 6A). Enhanced NMU reduced basal levels of circulating incretin levels, GLP1 and GIP (FIG. 6B-C). GLP1 and GIP are produced and secreted from the intestinal tract, including the ileum. Using a mouse ileum culture system, glucose-induced secretion of GLP1 and GIP were suppressed by NMU (FIG. 6D-E).

FIG. 7A-7D: NMU Signaling Attenuation Enhances Incretin Output.

Figure 7A:
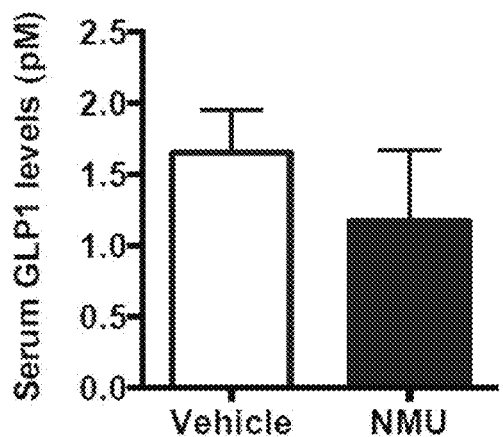
FIG. 7A-7D. Depicts data related to NMU signaling attenuation enhancing incretin output.
Figure 7B:
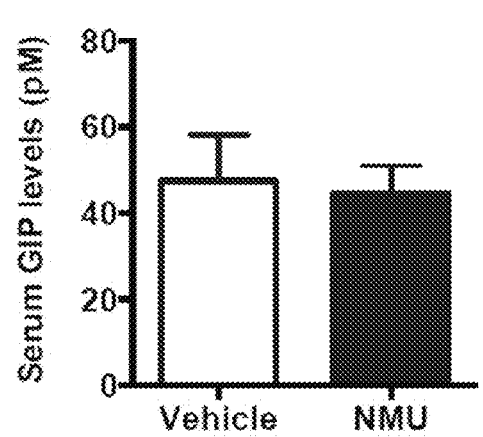
Figure 7C:
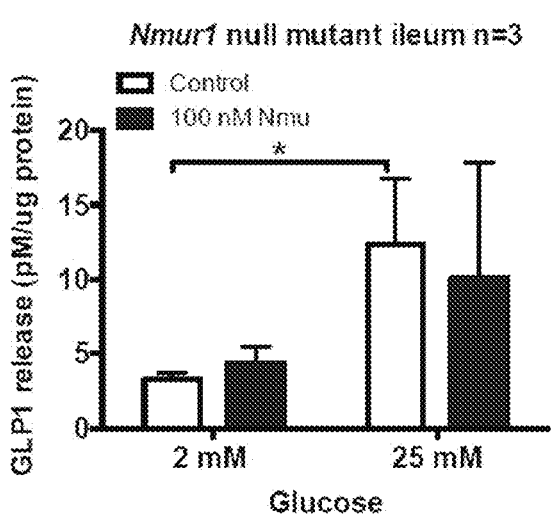
Figure 7D:
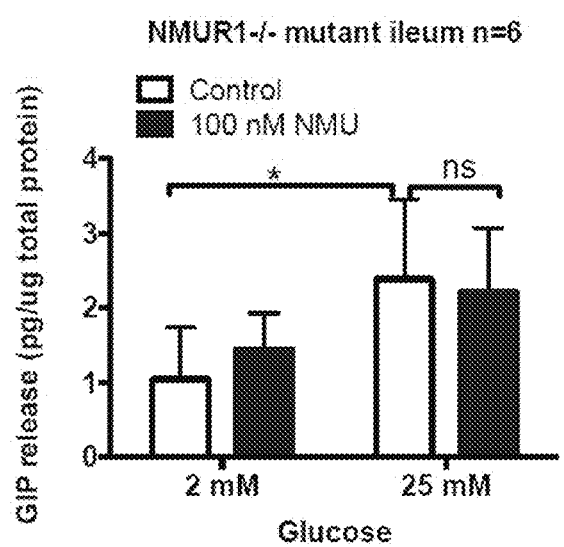

In NmuR1 null mutant mice, NMU inhibition of glucose-induced GLP1 and GIP output was lost in vivo (FIG. 7A-7B: compare to FIG. 6B-FIG. 6C). In cultured ileum from NmuR1 null mutant mice, NMU inhibition of glucose-induced GLP1 and GIP output was lost (FIG. 7C-7D; compare to FIG. 6D-6E).

Figure 8A:
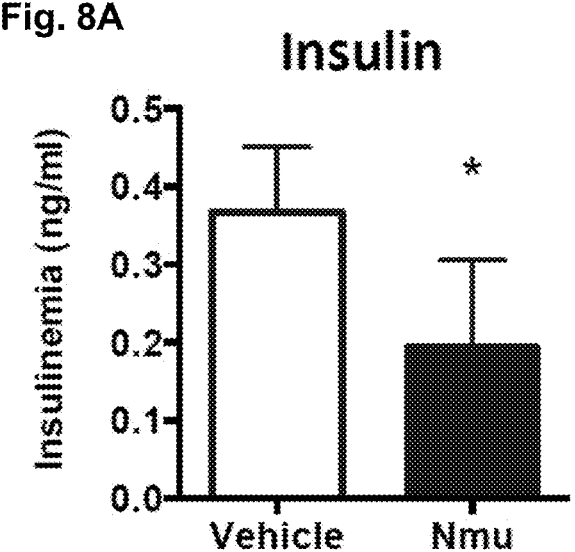
FIG. 8A-8B. Depicts data related to NMU signaling decreasing insulin and increasing glucagon output in vivo.
Figure 8B:
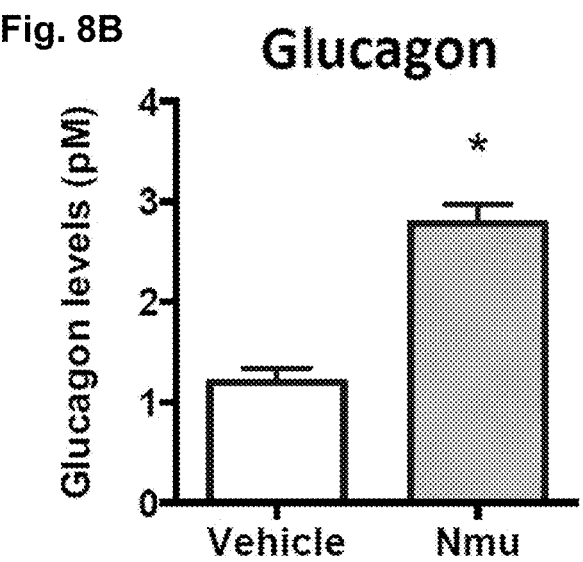

FIG. 8A-8B: NMU Signaling Decreases Insulin and Increase Glucagon Output in Vivo.

Increased plasma NMU in mice lowered basal insulinemia (FIG. 8A) and enhanced glucagonemia (FIG. 8B).

Figure 9A:
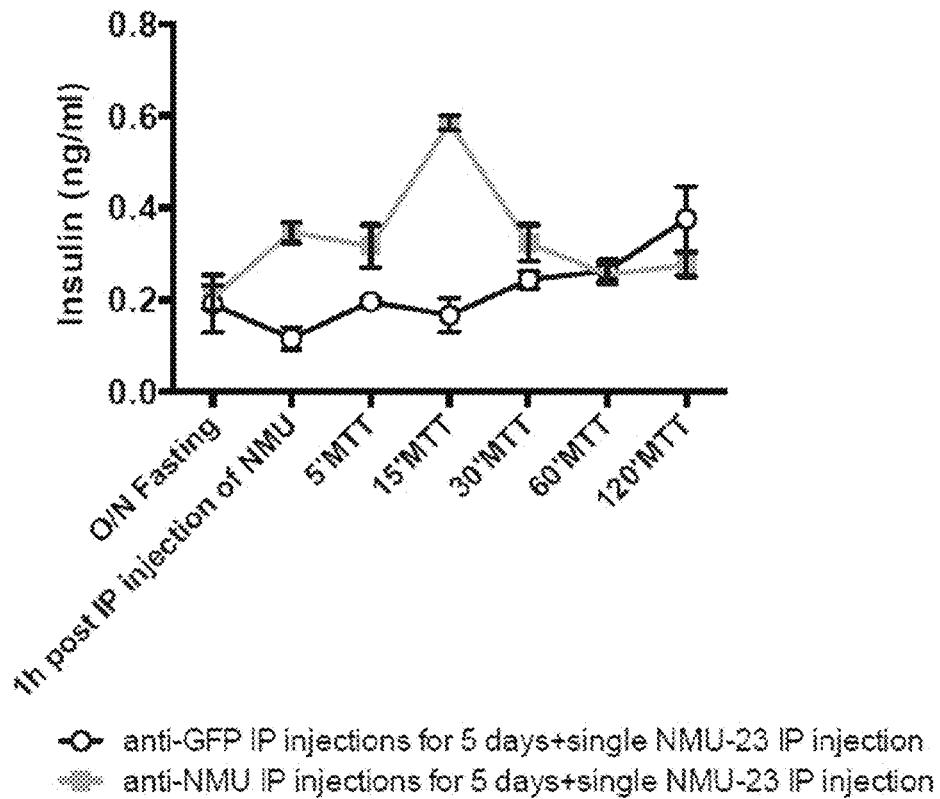
FIG. 9A-9B. Depicts data related to anti-NMU antibody therapy promoting insulin secretion and eliminating NMU-induced glucose intolerance.
Figure 9B:
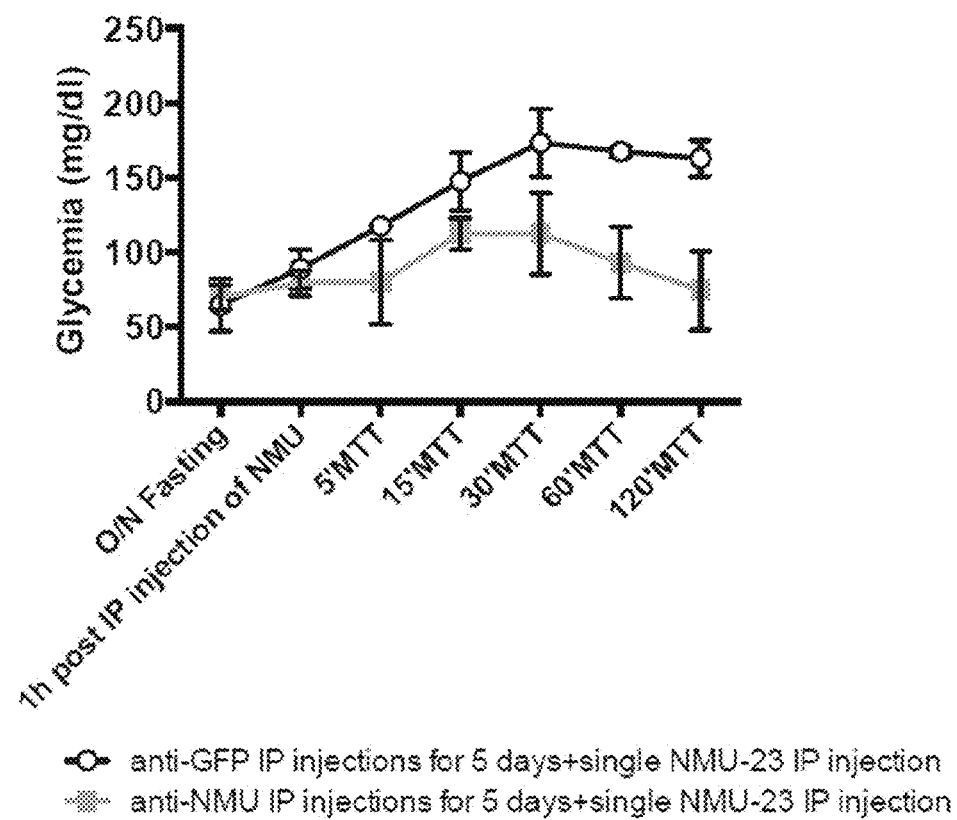

FIG. 9A-9B: Anti-NMU Antibody Therapy Promotes Insulin Secretion and Eliminates NMU-Induced Glucose Intolerance.

A single injection of NMU impaired insulin excursion in response to a meal challenge and led to hyperglycemia over 120 minutes. Co-injection with an anti-NMU monoclonal antibody that binds to a region common to mouse and human NMU (antibody C578, see FIG. 10) neutralized circulating NMU levels, restored insulin secretion (FIG. 9A) and improved glucose clearance (FIG. 9B).

FIG. 10.

CDR sequences were obtained from both light and heavy chains of newly generated anti-NMU antibodies (2A16, C578) that bind to human NMU (C578 binds to both human and mouse NMU).

Example 3 Neuromedin Signaling Basis of Diabetes in Chronic Pancreatitis and Pancreatic Ductal Adenocarcinoma Investigating the Neuromedin Signaling Basis of Diabetes in Chronic Pancreatitis and Pancreatic Ductal Adenocarcinoma Neuromedin U (NMU) is a peptide hormone produced by enteroendocrine cells and CNS neurons. In pre-clinical studies, NMU is a potent suppressor of insulin secretion by human islets. NMU also suppresses secretion of the incretin hormone GLP-1. The data and investigations provided herein demonstrate that NMU is mis-expressed in the pancreas in humans with chronic pancreatitis, and established pancreatic ductal adenocarcinoma, and that serum NMU levels are elevated in subsets of subjects with PDAC or pancreatitis. Thus, ectopic pancreatic NMU may promote pancreatogenic diabetes mellitus (T3cDM) and serum NMU levels can be a biomarker of chronic pancreatitis, pancreatic metaplasia or neoplasia.

Nmu is a Hormone that Suppresses Insulin Secretion by Pancreatic Islets

A secreted hormone, Limostatin (Lst), suppresses insulin secretion and production following starvation in Drosophila (Alfa et. al., Cell Metab. 2015 Feb. 3; 21(2):323-33). Lst is produced and secreted by fly corpora cardiaca cells, best known as cells that also secrete adipokinetic hormone (AKH), a functional orthologues of glucagon. Many neuropeptides signal through G protein-coupled receptors. All known orphan GPCRs were screened in Drosophila and Computed Gene #9918 (CG9918) was identified as a GPCR expressed in IPCs that negatively regulates insulin expression and secretion in the adult fly. Pharmacogenetic findings indicated that Lst regulates insulin secretion directly in IPCs, and support the view that CG9918 encodes a Lst receptor. The transmembrane domains encoded by the fly Lst receptor have highest sequence homology to the mammalian neuromedin U receptor 1 (NmuR1). Nmu encodes a pre-prohormone expressed in the brain (including hypothalamic nuclei) and in peripheral organs, including abundant expression in gastrointestinal organs. Thus, mouse NMU and human NMU production in gastrointestinal organs was assessed. In humans, NMU immunoreactivity was localized to scattered enteroendocrine cells that co-expressed Chromogranin B and were distributed in the gastrointestinal tract, prominently in stomach pyloric mucosa, duodenum and ileum (FIG. 11A-11B). Consistent with these results, Nmu mRNA expression was detected prominently in human stomach, duodenum, jejunum, ileum and colon. A similar distribution of Nmu$^+$ cells was detected in the adult mouse gastrointestinal tract. In the stomach, the greatest number of Nmu$^+$ cells was found in the cardia and greater curvature. Based on the intestinal segment lengths, the mouse and human ileum contains the greatest number of Nmu$^+$ cells. By contrast there was little to no detectable NMU production in mouse or human pancreas.

Figure 12A:
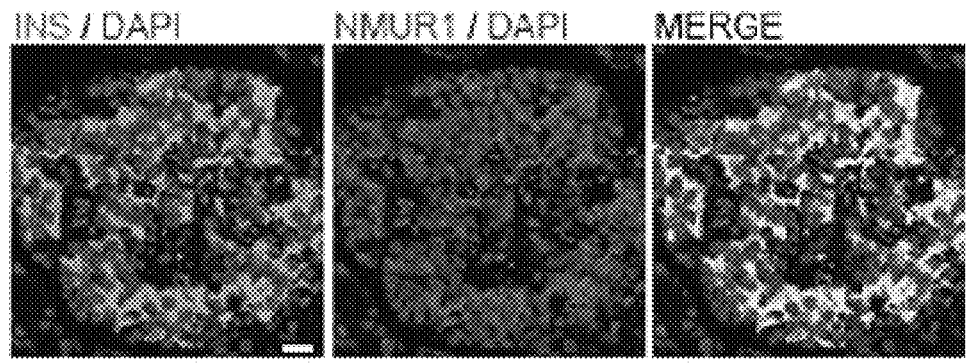
FIG. 12A-12C.
Figure 12B:
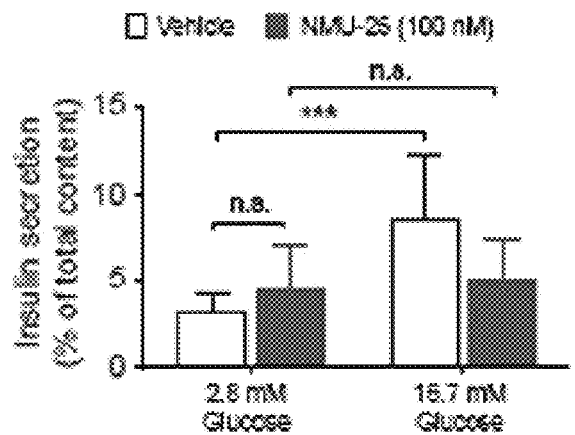
Figure 12C:
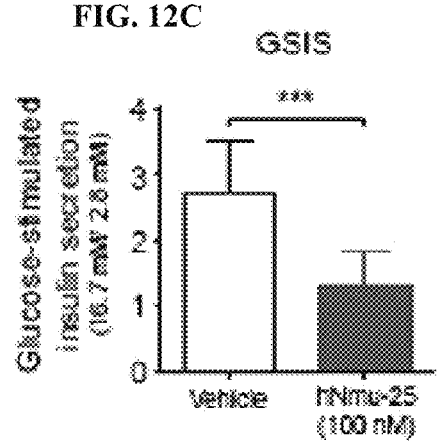

In humans and other mammals, peripheral effects of Nmu are mediated by NmuR1, while NmuR2 is primarily expressed in the CNS. mRNA encoding NmuR1 but not NmuR2 was readily detected by qPCR and in situ hybridization in isolated human and mouse islet β-cells. NmuR1 production was restricted to insulin$^+$ β cells (FIG. 12A). Little to no signal was detected in glucagon$^+$ α cells, somatostatin$^+$ δ cells or exocrine ducts and acinar cells. To test directly if NMU can suppress insulin secretion, islets were isolated and glucose-stimulated insulin secretion (GSIS) was assessed at a concentration of NMU reported to elicit physiological responses (Jones et. al., Regul Pept. 2006 Sep. 11; 136(1-3):109-16). Human NMU potently suppressed glucose-stimulated insulin secretion from human islets in static batch culture assays (FIGS. 12B-12C) and islet perifusion experiments. An NMU R165W allele that encodes a mutant peptide was previously found to co-segregate in an autosomal dominant pattern with early-onset obesity and hyperinsulinemia. In human islet perifusion assays, the R165W NMU variant failed to suppress insulin secretion compared to wild-type NMU. These data suggest that the human NMU R165W mutation represents a hypo-morphic loss-of-function allele, and that impaired regulation of insulin secretion by NMU underlies metabolic changes in carriers of this allele. Collectively, the data presented here shows that NMU is produced in the gastrointestinal tract (but not in the pancreas) and that nanomolar levels of NMU strongly inhibit insulin secretion by β-cells in mouse and human islets.

Nmu Infusion In Vivo Regulates Insulin, GLP-1 and Glucagon Output, and Glucose Tolerance The ability to measure serum NMU protein in mice (e.g., using the two-way ELISA disclosed in herein) permitted studies to investigate the impact of in vivo NMU infusion on crucial regulators of metabolism like insulin and glucagon. It was confirmed that a simple schedule of daily infusion by intraperitoneal injection led to a two-fold increase of mean serum NMU levels (FIG. 13A). Serum insulin and GLP-1 levels were reduced, while glucagon levels were increased (FIG. 13B-13D). Consistent with these findings, reduced insulin secretion and impaired glucose tolerance were detected after oral glucose tolerance testing in mice infused with NMU (compared to vehicle-infused controls; FIG. 13E-13F). Thus, acute NMU infusion leading to a doubling of serum concentration was sufficient to evoke changes of Insulin, GLP-1 and Glucagon that promote a diabetes-like state. Based on these findings, it was hypothesized that states of relative NMU excess in humans may affect multiple hormones, including insulin, GLP-1 and glucagon.

NMU Protein is Mis-Expressed in Human Chronic Pancreatitis and PDAC

NMU protein is not detectable in human pancreatic duct, acinar or islet cells of subjects without known pancreatic diseases, and using immunohistology no NMU was detected in islets, ducts or acinar cells of pancreas tissue from such donors (FIG. 14A). In the spectrum of injury and inflammation leading to metaplasia and progression to neoplasia in visceral organs, ectopic expression of hormones can lead to 'para-neoplastic' syndromes, like in small cell lung cancer pathogenesis. To investigate the possibility of using NMU as a biomarker of chronic pancreas injury, the possibility that NMU may be mis-expressed by pancreatic cells in chronic pancreatitis or pancreatic ductal adenocarcinoma was assessed. In ⅔ cases of chronic pancreatitis, immunohistology studies revealed ectopic NMU production in ductal epithelium (FIG. 14B). Likewise in 2/2 cases of PDAC, NMU expression in duct-like cells was observed (FIG. 14C-14D). By contrast, in areas without evidence of tumor infiltration in both PDAC cases, or in 2 cases of acute pancreatitis, NMU production in the pancreas was not observed.

Figure 15:
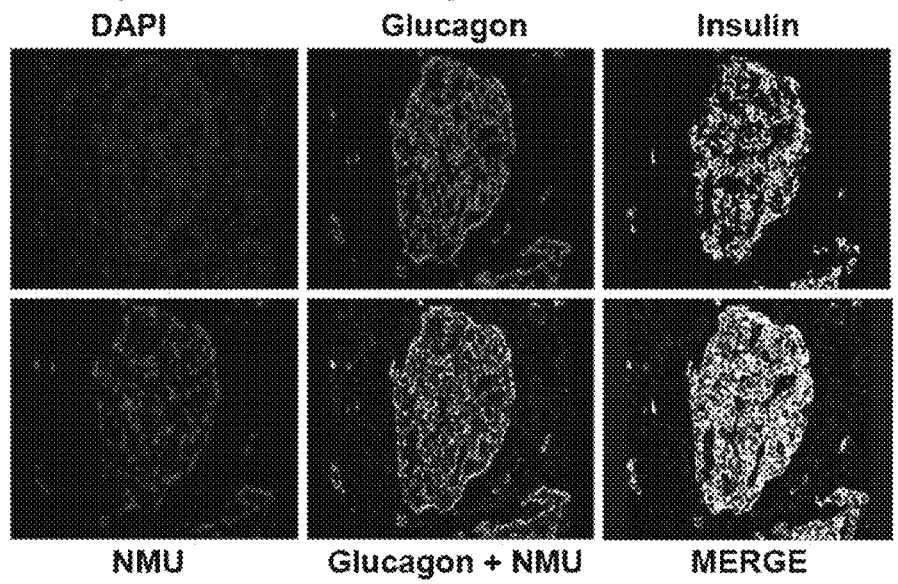
FIG. 15. Depicts data related to co-labelling with antibodies specific for NMU, Insulin and Glucagon, which demonstrated that Glucagon$^+$ cells (but not Insulin$^+$ cells) mis-expressed NMU.

NMU is not normally detected in human islets. Surprisingly, in a subset of islets adjacent to areas of obvious neoplasia in both PDAC cases, NMU immunostaining was observed in islet cells. Co-labelling with antibodies specific for NMU, Insulin and Glucagon demonstrated that Glucagon$^+$ cells (but not Insulin$^+$ cells) mis-expressed NMU (FIG. 15). These findings suggest that subsets of human islets may be influenced by PDAC, leading to ectopic production of NMU in islets. Together, the data are consistent with pancreatogenic NMU in chronic pancreatitis or PDAC being a biomarker and promoter of disease progression.

Meta-Analysis of NMU mRNA Expression in PDAC

Figure 16:
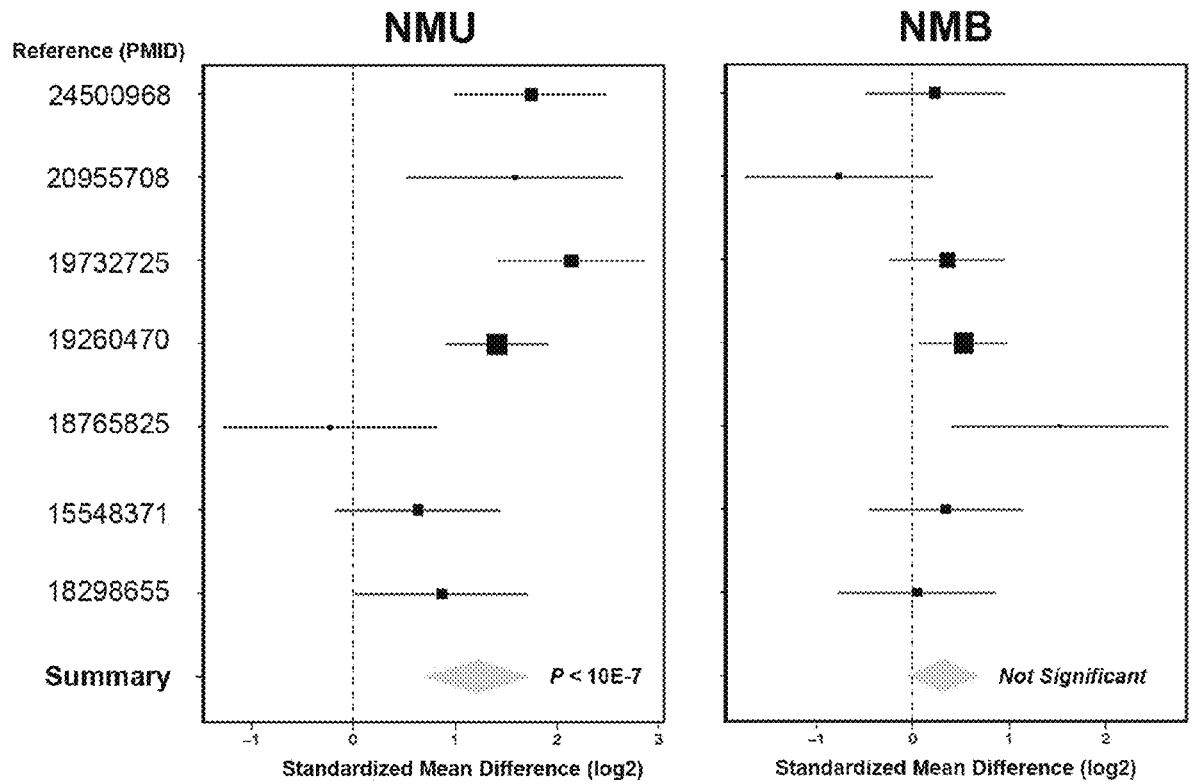
FIG. 16. Depicts data related to levels of mRNA encoding NMU in patients with PDAC. Depicted results are of a meta-analysis: NMU mRNA expression is increased in PDAC. The x-axis represents the standardized mean difference, effect size from each dataset, between PDAC and normal in log 2 scale. The size of the square is proportional to weighted inverse of the variance, of each study-specific effect size. The whiskers are the 95% confidence interval of the effect size of each study. The yellow diamond and its width represent the pooled effect size and the 95% confidence interval for a given gene, respectively.

To assess whether NMU mRNA levels are elevated in PDAC existing genome-scale expression profiles from human PDAC were analyzed. Briefly, meta-analysis approaches were used to assess data sets from a total of 264 PDAC and 91 normal expression profiles normalized using gcRMA (Khatri et al, Ann Intern Med. 2013 Jan. 1; 158(1):

35-46; Chen et al., Cancer Res. 2014 May 15; 74(10):2892-902). Hedges' adjusted g test was used for each gene to combined effect sizes (black squares) from each dataset into a pooled effect size (yellow diamond) to estimate the amount of change in expression across all datasets. A pooled effect size and standard error were obtained by combining effect sizes from each dataset using the random effects inverse-variance technique. P value was computed from the z-statistics, and adjusted using the Benjamini Hochberg method. This revealed a significant increase of mRNA encoding NMU in this sampling ($P<10^{-7}$), but not mRNA encoding neuromedin B (NMB: FIG. 16). Thus, a set of independent data supports the hypothesis that pancreatic NMU expression is abnormally increased in PDAC.

Figure 17:
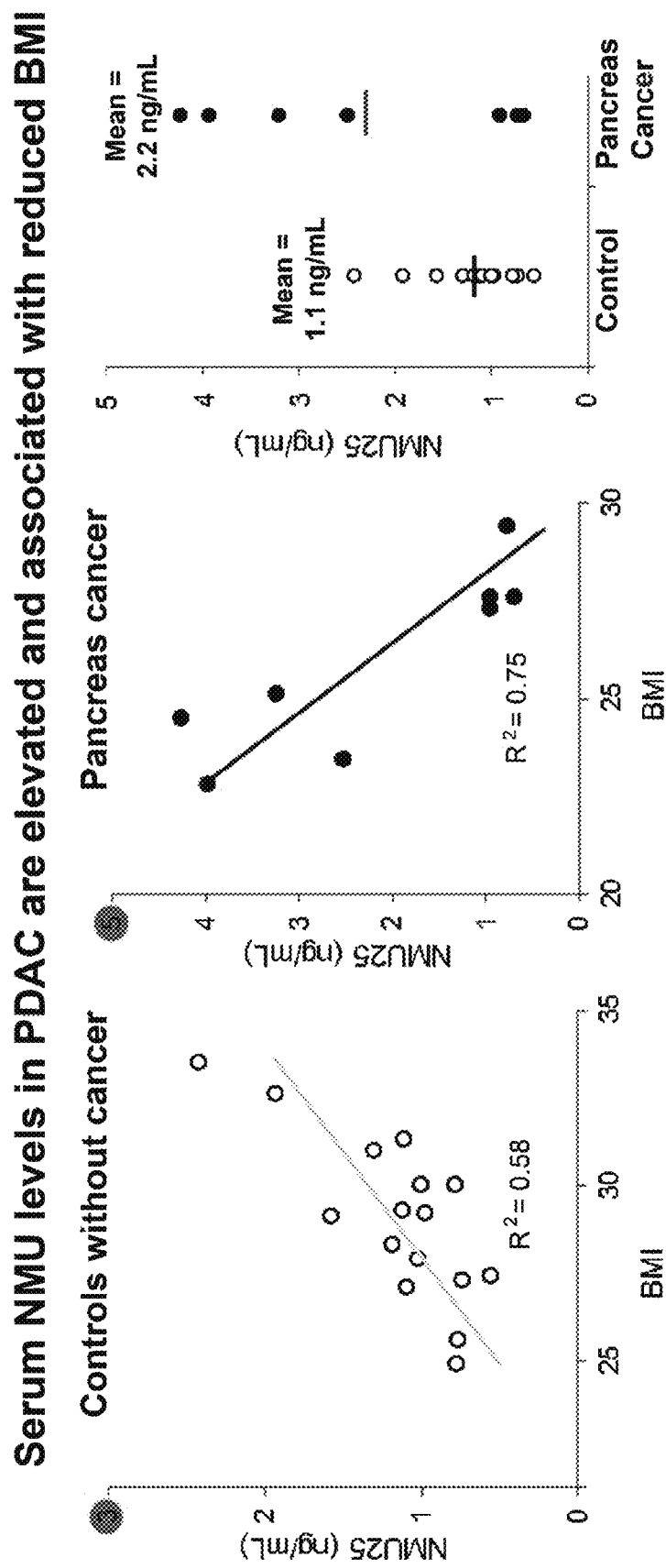
FIG. 17. Depicts data related to measurements of serum NMU using a subject two-way ELISA. NMU was measured in serum from control subjects without cancer or from subjects with advanced pancreatic ductal adenocarcinoma (PDAC).

NMU ELISAs Reveal Elevated NMU Levels in PDAC Associated with Reduced BMI and Cachexia ELISAs for mouse and human NMU are sold commercially, but have significant limitations. In fact, prior reports claim that NMU was undetectable in rodent serum, leading to the incorrect conclusion that NMU chiefly functions as a paracrine signal (Mitchell et al., Br J Pharmacol. 2009 September; 158(1):87-103). In the 'competitive' one-way assays, blood and other biological samples require purification and lyophilization of >1 milliliter of serum to reduce the impact of endogenous biotinylated macromolecules, and this concentration step introduces significant variation or irreproducibility. In another set of 'two-way' ELISAs, the immunogen was pre-proNMU and these kits do not detect processed bioactive human NMU in serum. To overcome this, a new 2-way ELISA assay was built with novel monoclonal antibodies. This has significantly improved assay reproducibility, and permits use of 10 microliters of serum, without a concentration step. Mouse NMU protein and human NMU protein can now be detected at 0.1 to 20 ng/mL (FIG. 17). Detection of NMU in human or mouse serum does not require addition of protease inhibitors as required for stabilizing GLP-1.

With this new human ELISA serum NMU was measured in control subjects without cancer or with advanced pancreatic ductal adenocarcinoma (PDAC). In controls without known pancreatic disease or T2DM (type 2 diabetes), NMU levels increased with BMI, an association that was statistically significant (FIG. 17: Spearmann Rank=0.69). By contrast two striking features of NMU levels in PDAC patients were observed. First, mean serum NMU levels were elevated about two-fold compared to controls (FIG. 17: note the differing Y-axis scales). This finding is consistent with the analysis that revealed increased pancreatic NMU mRNA expression in PDAC, and indicates that this ectopic pancreatic expression may result in elevated serum NMU levels. In turn, this supports the view that the para-neoplastic effects of NMU may be both paracrine and endocrine. Excluded from this analysis of PDAC are two subjects in whom very high levels of NMU were observed, including one subject with PDAC and diabetes mellitus whose NMU level was 19.5 ng/mL (NMU level>3 SD above mean). Although these differences are not yet statistically significant, this likely reflects the relatively small number of patients analyzed in the preliminary studies. Second, unlike in controls, a striking increase of NMU levels was observed in patients with low BMI, an association that was statistically significant (FIG. 17; Spearmann Rank=-0.83; P=0.00015). In the subset of patients with highest NMU and lowest BMI, there was clinical evidence of tumor cachexia. In prior studies of transgenic mice, systemic NMU overproduction was found to reduce body mass, decrease adiposity and food intake, resulting in lean mice. Thus, NMU over-production can produce states mimicking pre-cachexia. Using the systems discussed above, it was shown that doubling of serum NMU levels is sufficient to impair insulin and incretin output, and disrupted glucose regulation (e.g., see FIG. 13 above). It is suggested here that ectopic pancreatic NMU is a para-neoplastic factor that can promote diabetes, cachexia and other metabolic alterations.

Evidence for Increased Serum NMU Levels in Subjects with Chronic Pancreatitis

Figure 18:
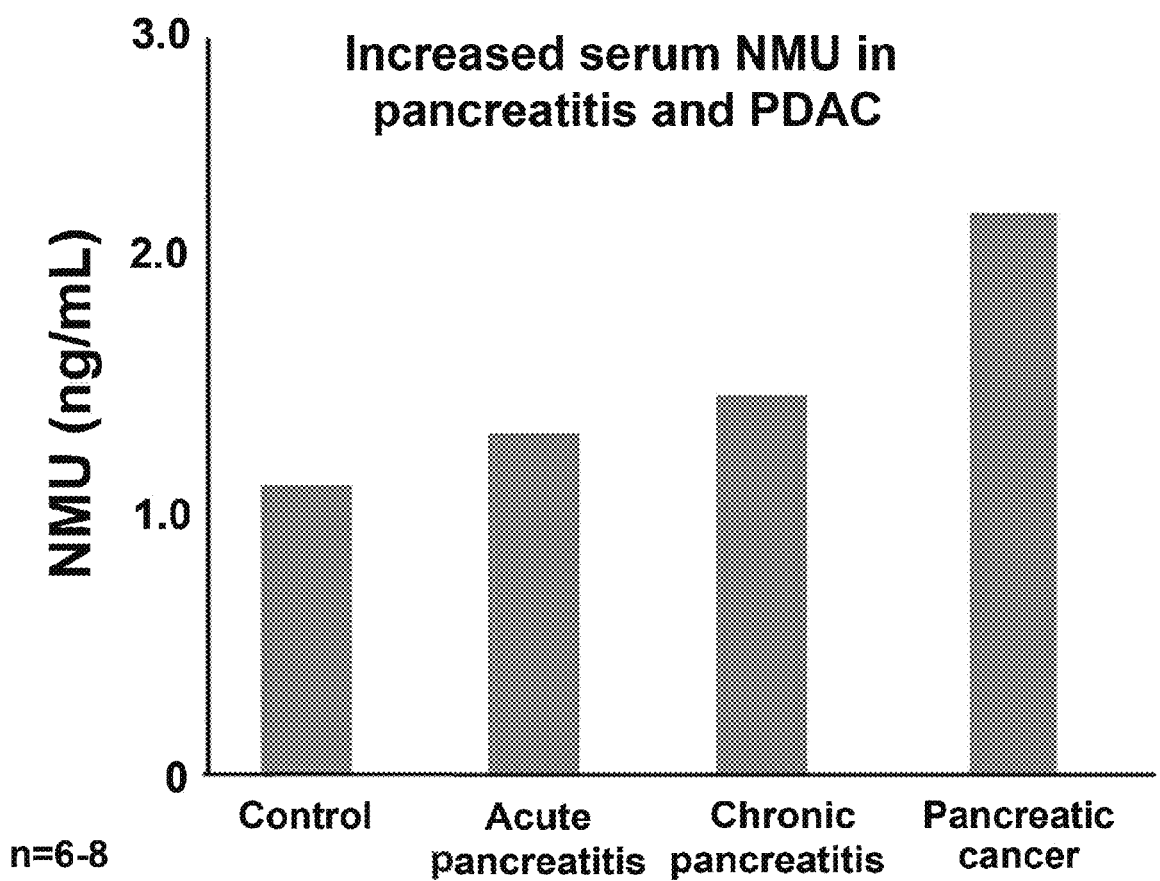
FIG. 18. Depicts serum levels of NMU measured from subjects.

The studies presented here related to gene expression and NMU protein production in pancreatitis suggested that serum levels of NMU might be detectably increased in this setting. To test this, feasibility studies of patients with acute and chronic pancreatitis were performed. Clear trends were observed indicating that the mean serum levels of NMU were increased in subjects with chronic pancreatitis (and pancreatic cancer), compared to those with acute pancreatitis or control subjects without exocrine pancreas disease (FIG. 18). These findings highlight the dynamic range of the two-way ELISA serum assay disclosed herein, and indicate that the assay can identify elevated NMU levels in pancreatitis and PDAC.

An interesting link of these findings comes from the observation that production of cytokines like IL-6 in macrophages is regulated by NMU. Thus, a pro-inflammatory role for NMU is implicated via its ability to induce synthesis and release of Th2 cytokines. Studies in mice suggest that Th2 cytokines and IL-4R□ signaling activates pancreatic stellate cells, promoting the characteristic fibrogenesis observed in chronic pancreatitis progression. These results are substantiated by findings from human ex-vivo co-cultures of PSCs and macrophages. Thus ectopic expression of NMU in chronic pancreatitis and PDAC (FIG. 14, FIG. 15) could amplify Th2 signaling to perpetuate progression of disease.

Figure 19A:
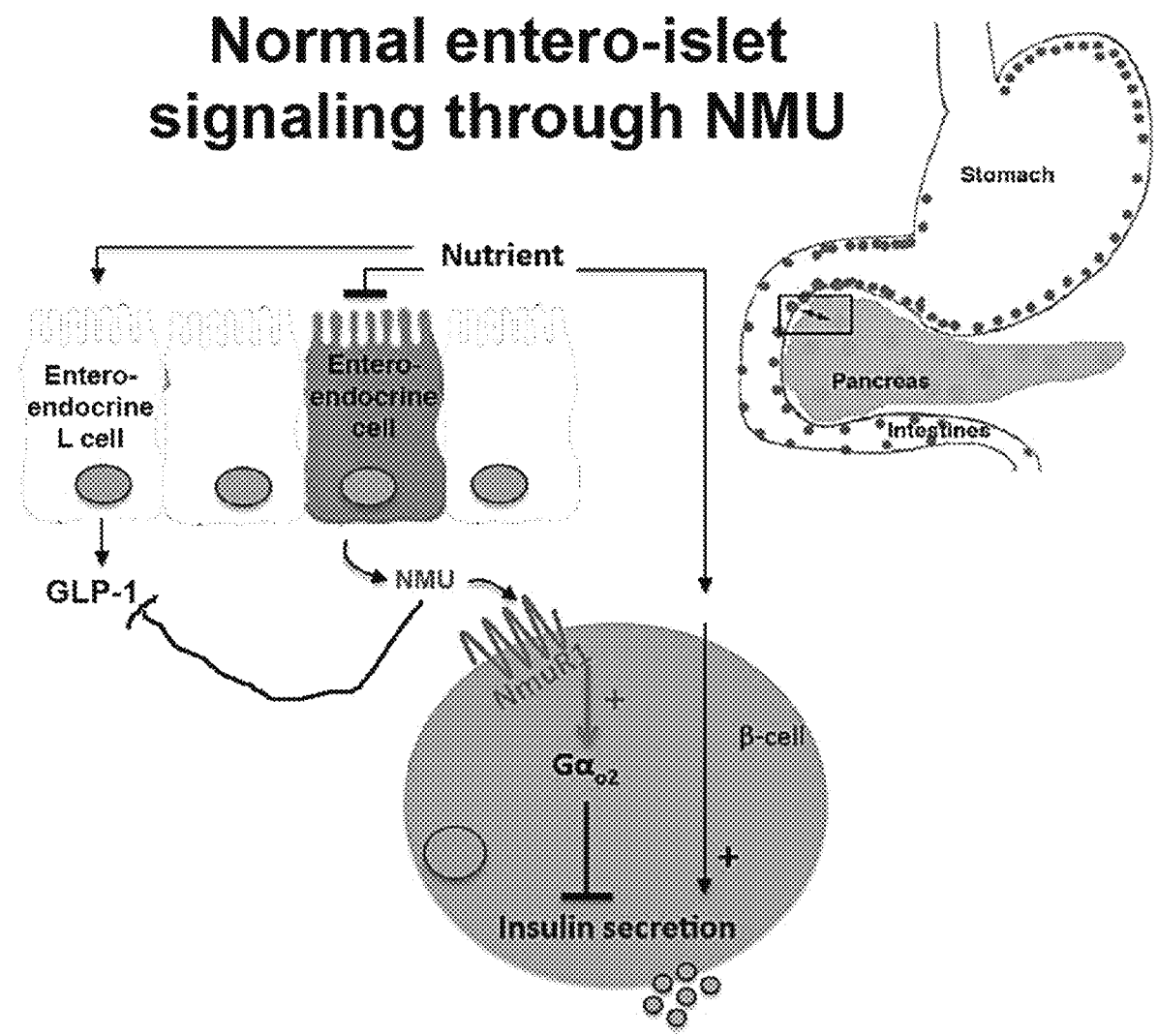
FIG. 19A-19B. Depict schematic representations of NMU signaling in normal and diseased states.
Figure 19B:
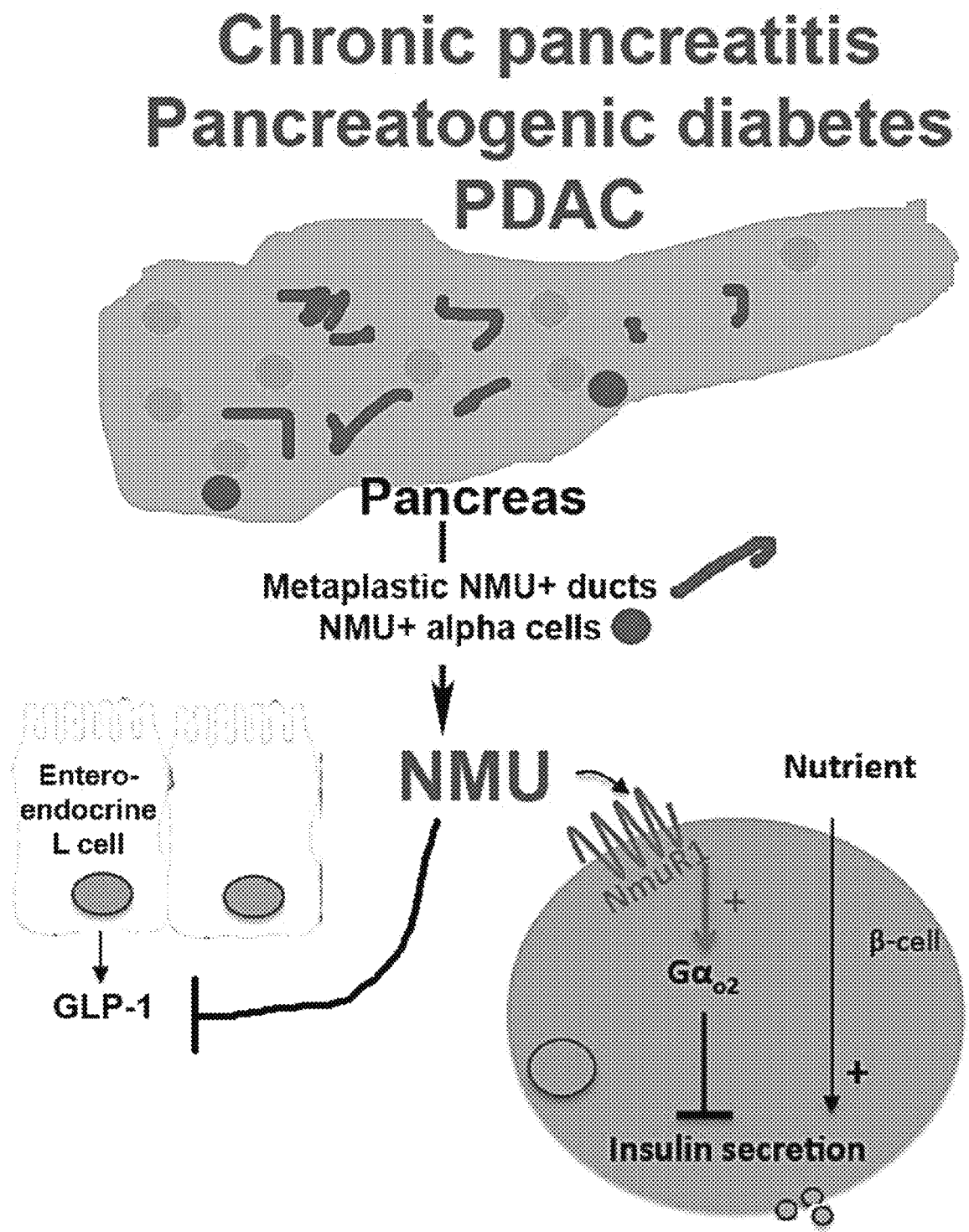

The investigations of NMU signaling presented herein suggest (1) that circulating NMU regulates a physiological signaling pathway that controls insulin and GLP-1 output in vivo (FIG. 19A), and (2) this pathway is perturbed in common chronic exocrine pancreas diseases like pancreatitis and pancreas adenocarcinoma. In these diseases, the data show that NMU expression (mRNA and protein production) are abnormally increased in the human pancreas, where NMU is not normally produced (FIG. 19B). Sites of ectopic NMU production may include metaplastic ducts, neoplastic cells and islet cells. Based on the finding that NMU circulates, and is measurable by the two-way ELISA disclosed herein, elevated NMU levels in chronic pancreatitis and PDAC can be detected in subsets of patients, and NMU likely suppresses output of insulin and incretins like GLP-1, leading to dysregulated glucose homeostasis. Thus, pancreatogenic NMU may reflect ongoing cellular metaplasia or neoplasia in these diseases and thereby promote phenotypes found in pancreatogenic diabetes, including relative hypoinsulinemia, hypoincretinemia, and impaired glucose regulation.

Example 4

Mouse Nmu is produced in enteroendocrine cells in the stomach, duodenum, ileum and colon, while NmuR1 is expressed in islet β-cells. Based on the findings presented in this disclosure, we suggest that enteroendocrine Nmu serves as a crucial nexus between nutrient status, the gastrointestinal tract, and islet hormones to control metabolism. We suggested that Nmu signaling from gut to pancreas islets constitutes a new, physiologically important inter-organ signaling axis regulating mammalian metabolism.

Nmu is produced both in the CNS and peripheral tissues, particularly in the gastrointestinal tract. Nmu inhibits pancreatic insulin secretion. Nmu receptor1 (NmuR1) is a G protein-coupled receptor expressed in mouse and human islet β-cells. Factors that regulate β-cell insulin secretion, including the hormones somatostatin and galanin, and pertussis toxin, require the inhibitory G-protein $G_o2$ for proper secretory regulation. Mutations in human NMU are linked to hyperinsulinemia and obesity.

Starvation and feeding are potent selective forces, and hormonal responses to maintain metabolic balance in the face of nutrient restriction or abundance appear to be highly conserved in all animals. In mammals, powerful mechanisms potentiate insulin-secreting cell responses to the incoming glucose load before glucose levels rise. For example, incretin hormones such as glucagon-like peptide-1 (GLP-1) are secreted by enteroendocrine cells following a meal, and enhance glucose-stimulated insulin production and secretion from pancreatic β cells.

Prior to the work described in this disclosure, an enteroendocrine hormone induced by fasting that decreases insulin output (a "decretin") had not been identified. Loss of such a hormone has been postulated as one basis for the rapid resolution of diabetes phenotypes in obese patients following gastric bypass surgery (Rubino et al 2009), an increasingly common intervention.

Nmu is Functional and Inhibits Insulin Secretion by Pancreatic Islets

Figure 20A:
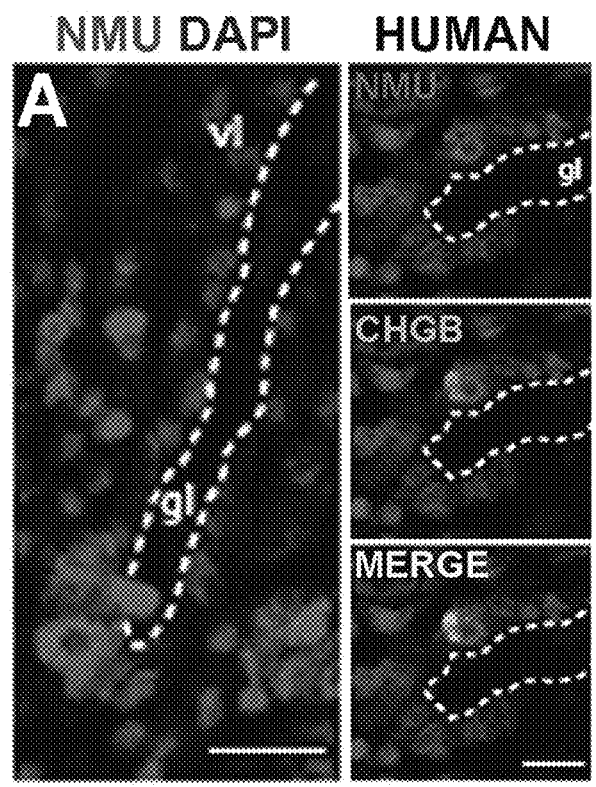
FIG. 20A-20C. Depict micrographs and schematic representations of NMU expression in humans and mice, and depicts data from RNA-Seq analysis of mouse duodenal and ileal Nmu-eGFP+ cells.
Figure 20B:
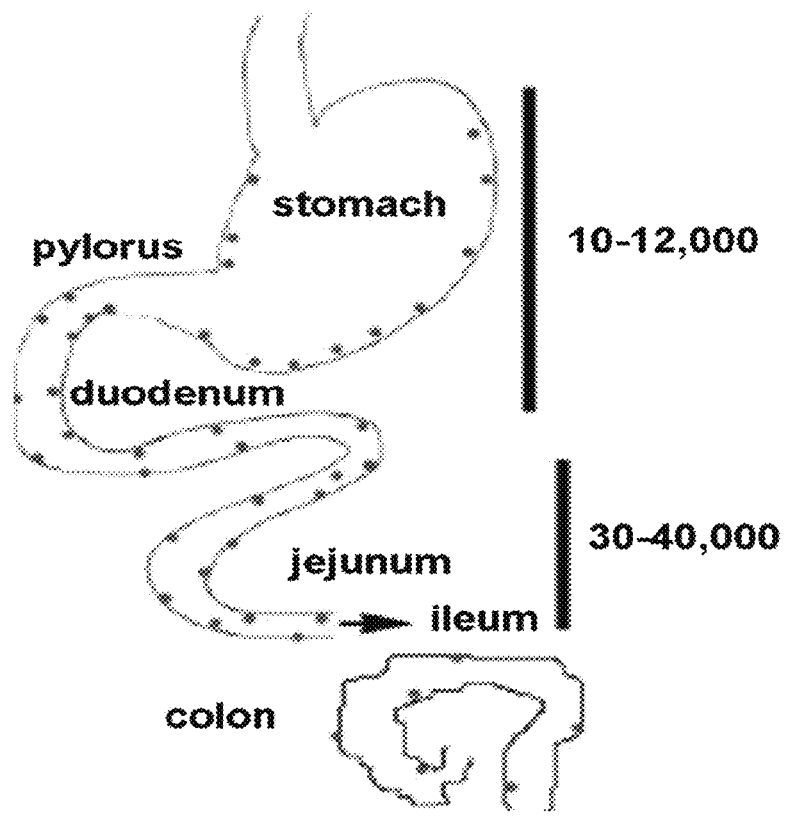
Figure 20C:
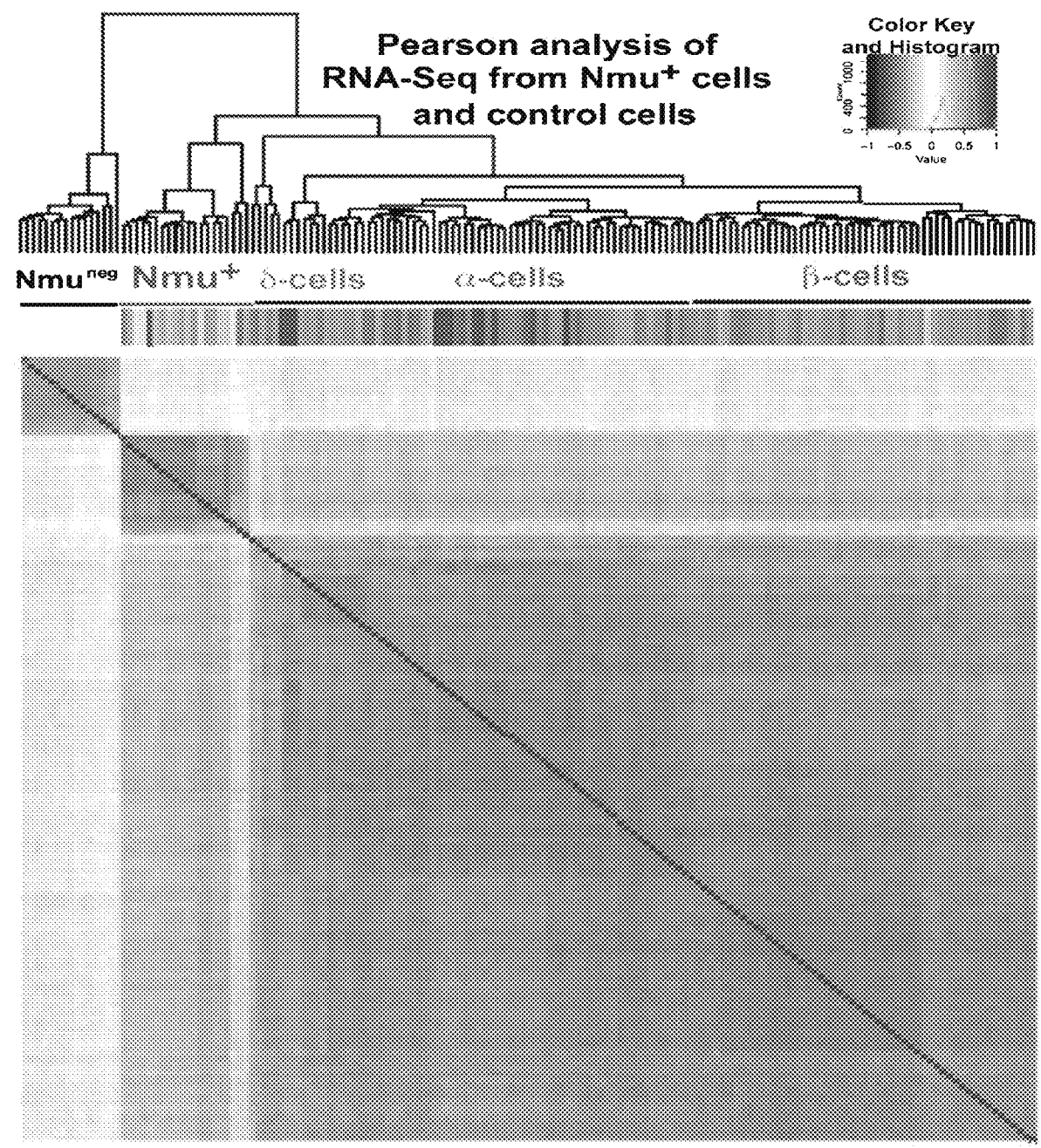

The transmembrane domains encoded by CG9918 have highest sequence homology to the mammalian Neuromedin U receptor 1 (NmuR1). Nmu encodes a pre-prohormone expressed in the brain (including hypothalamic nuclei) and in peripheral organs, including abundant expression in gastrointestinal organs. In mice, Nmu is a 23 amino acid peptide (Nmu-23); in human NMU is 25 amino acids (NMU-25). Mouse Nmu and human NMU production was assessed in gastrointestinal organs. In humans, NMU immunoreactivity was localized to scattered enteroendocrine cells that co-expressed Chromogranin B with a typical 'open type' morphology, and were distributed in the gastrointestinal tract, prominently in stomach pyloric mucosa, duodenum and ileum (FIG. 20A-B). Consistent with these results, NMU mRNA expression was detected prominently in human stomach, duodenum, jejunum, ileum and colon. To investigate mouse intestinal $Nmu^+$ cells, and understand mechanisms regulating Nmu production and secretion from enteroendocrine cells, mice were obtained that harbor a BAC transgene encoding an eGFP transgene 'knocked-in' to the Nmu locus. In adult mice, $Nmu\text{-}eGFP^+$ cells were readily detected by microscopy in stomach, duodenum, ileum, jejunum and colon (FIG. 20B). Standard methods were used to isolate and purify $Nmu\text{-}eGFP^+$ cells by fluorescence activated cell sorting (FACS). FACS isolation of $Nmu^+$ cells from stomach and small intestines yielded ~50,000 $Nmu^+$ cells per adult mouse, similar to the number of pancreatic islet α-cells. RNA-Seq analysis of duodenal and ileal $Nmu\text{-}eGFP^+$ cells (FIG. 20C) revealed co-expression of Nmu with enteroendocrine markers like ChgA, ChgB, Pcsk1, Cpe, NeuroD1, Lmx1a and Nkx2.2: none of these markers was detected in purified $Nmu^{neg}$ cells. $Nmu\text{-}eGFP^+$ cell expression was not detected for preproglucagon, GIP, Somatostatin, Motilin, Ghrelin or Insl5. Thus, Nmu cells appear to be distinct from $Nmu^{neg}$ cells, and from multiple known enteroendocrine cell types, including L-, K-, M- and D-cells. Comparison to mouse islet cell gene signatures by Pearson analysis revealed, as expected, that Nmu cells were distinct from $Nmu^{neg}$ cells and similar to islet cells, especially δ- and α-cells (FIG. 20C). Like other endocrine cells that depolarize in response to secretagogues, $Nmu^+$ cells expressed mRNAs encoding voltage-gated $Ca^{2+}$ channels like Cacna1a, voltage-gated sodium channels like Scn3a, and the glucose transporter Slc2a1 (Glut1). Consistent with these findings, an established primary ileal culture assay was used, and increased Nmu release was detected after exposure to 20 mM potassium chloride. FIG. 20: Human and mouse $NMU^+$ cells. (A) vl=mucosal villus, gl=gland.

Figure 21A:
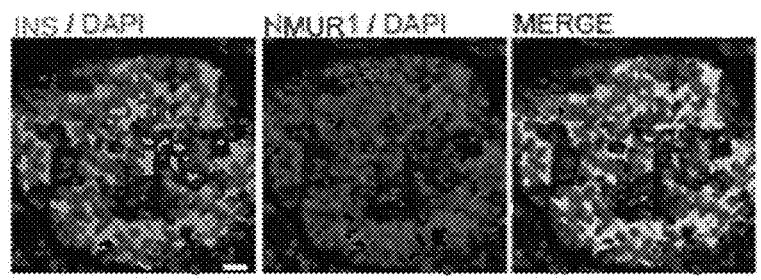
FIG. 21A-21C. Depict data showing NMUR1 expression in human β-cells and showing that NMU suppresses insulin secretion.
Figure 21B:
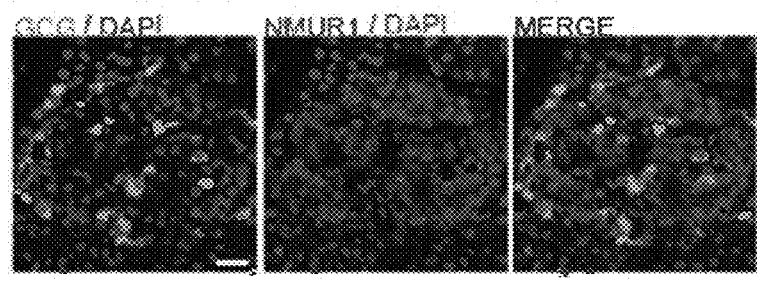
Figure 21C:
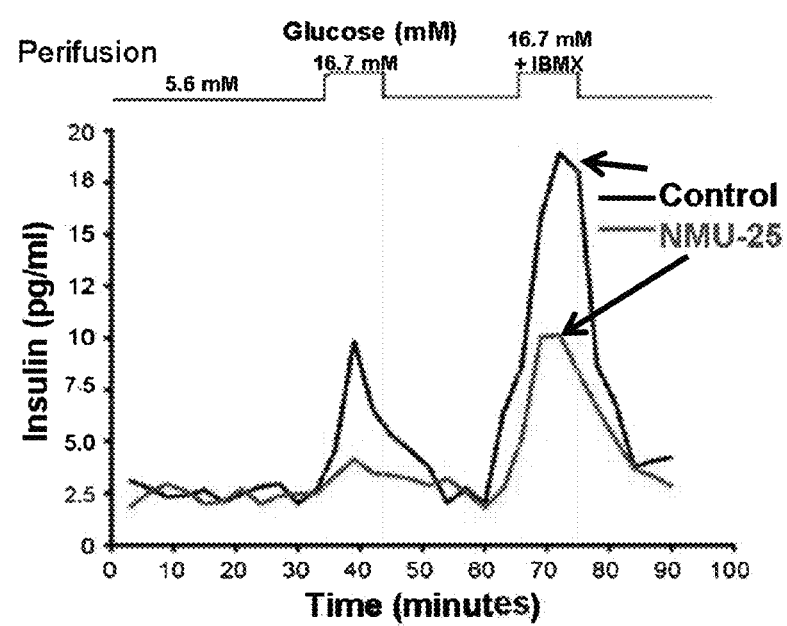
Figure 25:
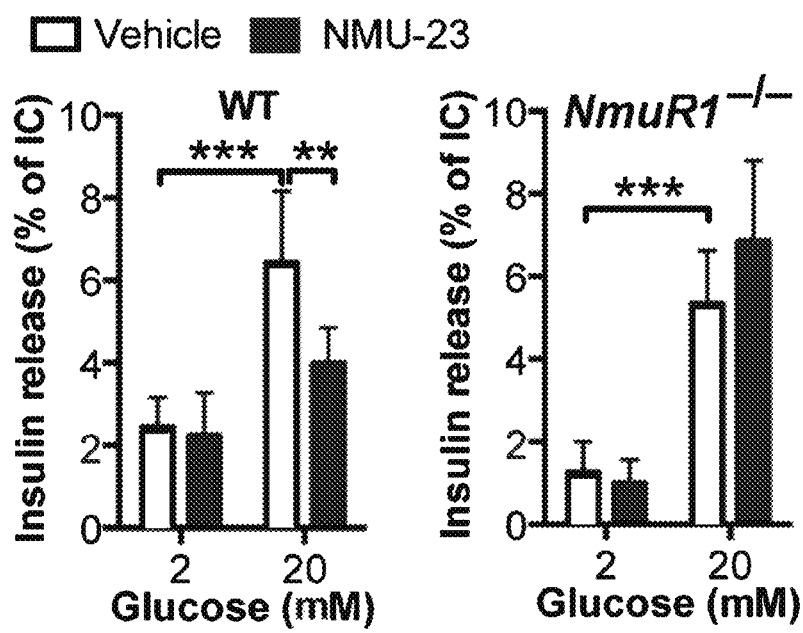
FIG. 25. Depicts data showing that NMU suppression of insulin secretion by cultured mouse islets requires NmrR1.

In humans and other mammals, peripheral effects of Nmu are mediated by NmuR1, while NmuR2 is primarily expressed in the CNS. mRNA encoding NmuR1 but not NmuR2 is readily detected by RNA-Seq, qPCR and in situ hybridization in isolated human and mouse islet β-cells, albeit at low levels (FIG. 21A). Little to no NmuR1 expression was detected in $glucagon^+$ α cells (FIG. 21B), $somatostatin^+$ δ cells or exocrine ducts and acinar cells. To test if NMU can suppress insulin secretion, human islets were isolated and glucose-stimulated insulin secretion at 50-100 nM, a concentration of NMU reported to elicit physiological responses, was assessed. Human NMU potently suppressed glucose-stimulated insulin secretion from human islets in perifusion experiments (FIG. 21C). Similar effects were observed with mouse Nmu and purified mouse islets (FIG. 25). Collectively, the work disclosed herein show that NMU is produced in the gastrointestinal tract (but not islets), and that nanomolar levels of NMU strongly inhibit insulin secretion by β-cells in mouse and human islets. FIG. 21: (A-B) Human NMUR1 is expressed in islet β-cells (A) but not in α-cells (B) or δ-cells. (C) Human islet perifusion shows NMU-25 suppresses insulin secretion.

Figure 22A:
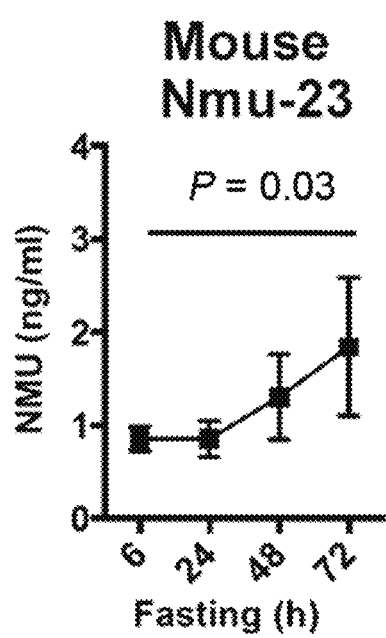
FIG. 22A-22C. Depict data showing serum NMU levels in mice and humans.
Figure 22B:
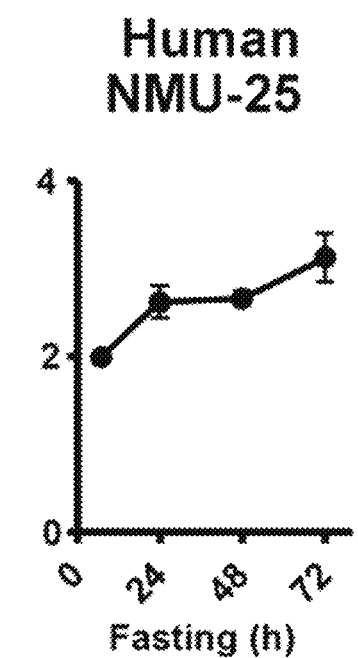

Commercially-available ELISA assays have not previously achieved reliable measures of circulating NMU in mouse or human serum; hence it was not clear that NMU was a bona fide endocrine hormone. To address this deficit, new 2-way ELISAs with newly generated monoclonal antibodies were built to measure NMU in these species. This new setup allows the use only 1-2 microliters of serum, without a hydrophobic-resin column concentration step. The new ELISAs detect mouse and human NMU in a working range spanning 0.2 to 900 ng/mL (FIG. 22). Nmu is detectable in mouse serum during ad libitum feeding, and Nmu levels increase after 48-72 hours fasting (FIG. 22A: n=3). Insulin levels decline throughout this period, reflecting regulation both by nutrient restriction and circulating factors. Circulating Nmu in fasted mice fell to baseline levels within one hour after enteral feeding but not after intraperitoneal glucose injection. Similar changes are observed in human volunteers fasted 72 hours (FIG. 22B: n=2). Thus, NMU levels increased during fasting in mice and humans. Together, these findings further support the concept that Nmu is a mammalian decretin.

Figure 22C:
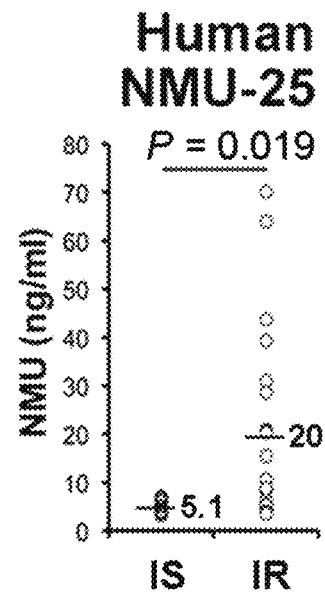

To assess whether human serum NMU levels can be detected in more common physiological settings, serum NMU was measured in human subjects stratified by insulin suppression testing. Age- and BMI-matched lean, non-diabetic women were stratified into insulin-resistant (IR: n=14) and insulin-sensitive (IS: n=7) groups on the basis of their steady-state plasma glucose (SSPG) concentration following a 180-minute infusion of octreotide, exogenous insulin, and glucose. Significant elevation of average serum NMU was observed in the IR group (FIG. 22C: 5.0 vs. 20, P=0.019). Thus, this work reveals increased circulating NMU levels in humans with impaired metabolism.

Figure 23A:
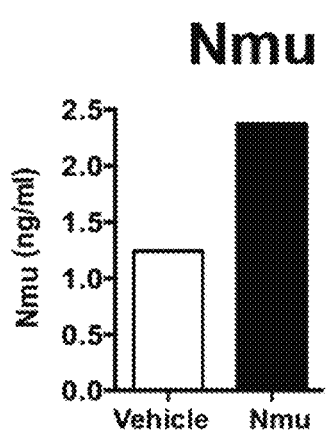
FIG. 23A-23F. Depict data related to in vivo NMU-23 infusion in mice.
Figure 23B:
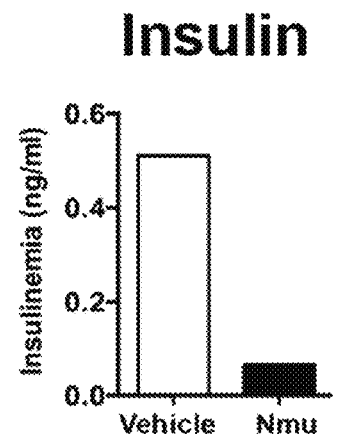
Figure 23C:
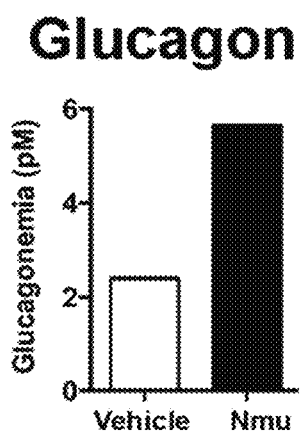
Figure 23D:
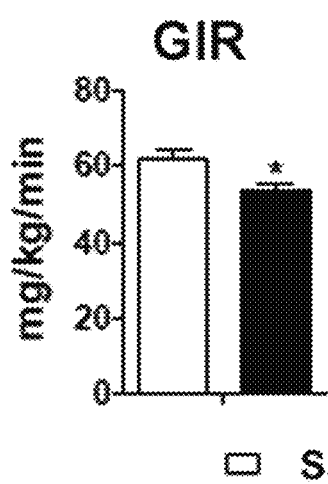
Figure 23E:
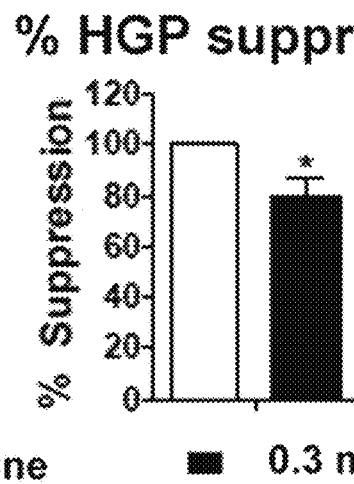
Figure 23F:
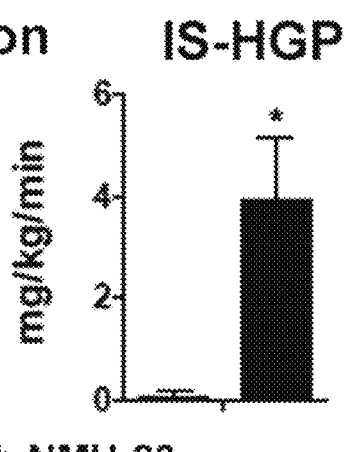
Figure 27A:
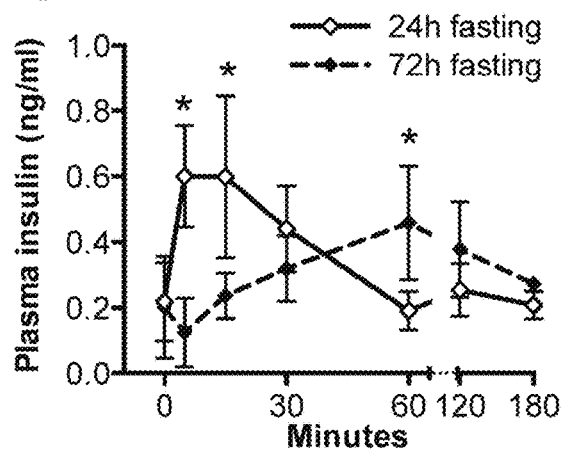
FIG. 27A-27D. Depicts data related to starvation diabetes and NMU injection.
Figure 27B:
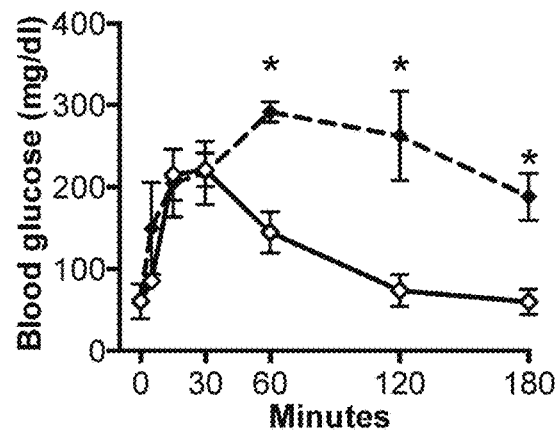
Figure 27C:
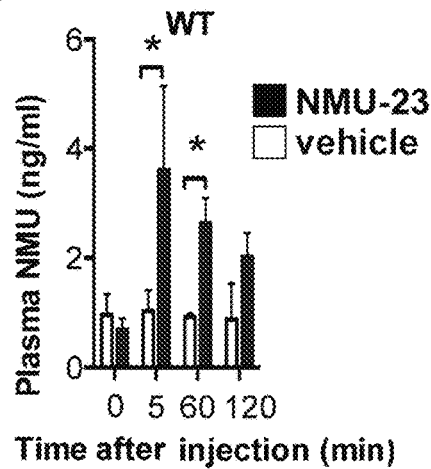
Figure 27D:
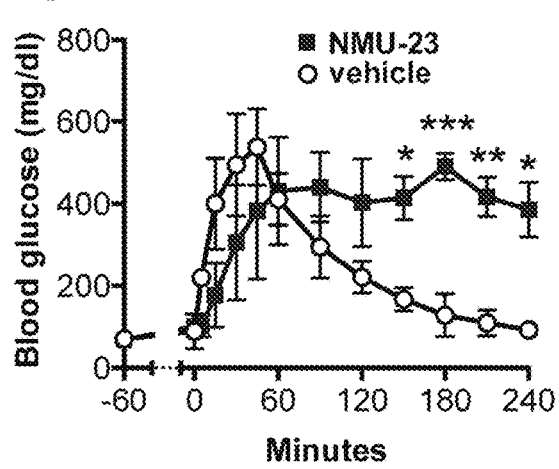

Nmu Infusion In Vivo Regulates Insulin and Glucagon Output, and Glucose Tolerance Identification of the normal range of serum NMU levels in mice guided studies to investigate the impact of physiologically-relevant increases of Nmu-23 after in vivo infusion (n=4). A doubling of NMU levels was detected within 10 minutes after IP infusion in 10 week-old B6J male mice fasted 12 hours (FIG. 23A). Serum insulin levels were reduced, while glucagon levels were doubled (FIG. 23B-C) after Nmu injection. The regulation of glucagon by Nmu is likely to be indirect, since NmuR1 or NmuR2 expression has not been detected in mouse or human α-cells. Consistent with these findings, insulin secretion was reduced and glucose tolerance was impaired after oral glucose tolerance testing in mice infused with Nmu (compared to vehicle-infused controls; FIG. 27C). Relative hyperglucagonemia from Nmu infusion could enhance hepatic glucose production. To investigate this, hyper-insulinemic clamp studies were performed. Compared to 10 week-old B6J male controls (n=7), isogenic mice infused with mouse Nmu-23 (0.3 mg/kg/hour; n=9) required reduced glucose infusion rate (GIR), and had reduced insulin-sensitive suppression of hepatic glucose production (HGP), consistent with relative hyperglucagonemia (FIG. 23D-F). FIG. 23: *P<0.05

Figure 24A:
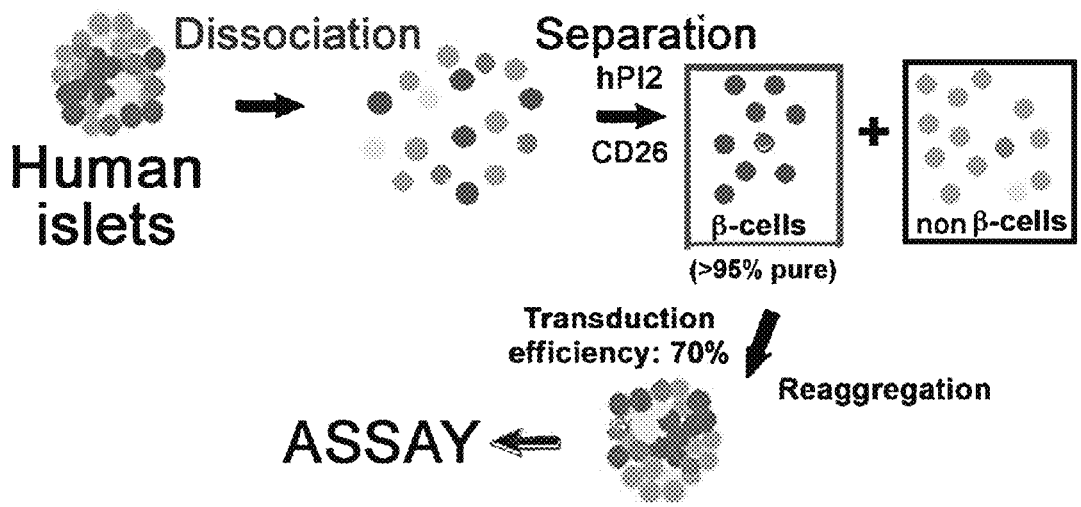
FIG. 24A-24F. Depict data related to genetics with primary human islet cells (e.g., using lentiviral vectors to express transgenes), and assays in pseudoislets.
Figure 24B:
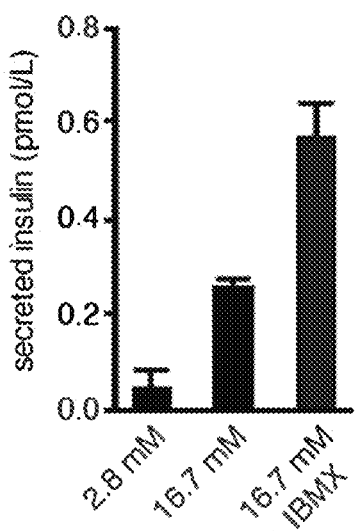

Efficient Genetic Transduction and Functional Assessment of Primary Human Islet Cells Transgenes were expressed in human primary islet cells, by dispersing islets to single cell suspensions, and then reaggregated into clusters. Islet cell clusters after re-aggregation (also called 'pseudoislets') remained responsive to glucose and other secretion signals like IBMX. After transplantation in mice, pseudoislets vascularized and achieved regulated insulin secretion (FIG. 24). Lentiviral vectors were used to infect human islet cells, to achieve expression of transgene-encoded products like nuclear Green Fluorescent Protein (nGFP). Less than 10% of islet cells were transfected when intact cultured islets were infected. By contrast, nGFP production was detected in 75% of islet cells after dispersion, lentiviral infection and re-aggregation (FIG. 24A). Immuno-panning and magnetic bead-based separation was used to purify dispersed β-cells and non-β-cells. This strategy achieved 140-fold purification and >95% purity of $CD26^{neg}$ $hPI2^+$ β-cells (FIG. 24A). This purification step allowed the targeting of primary human β-cells or α-cells using lentivirus, prior to reaggregation in pseudoislets. After lentiviral transduction and reaggregation, human pseudoislet insulin secretion in vitro remained regulated (FIG. 24B).

Figure 24C:
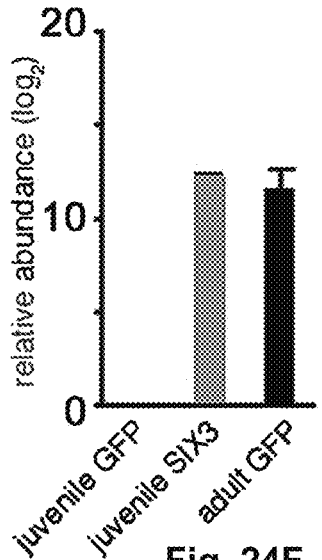
Figure 24D:
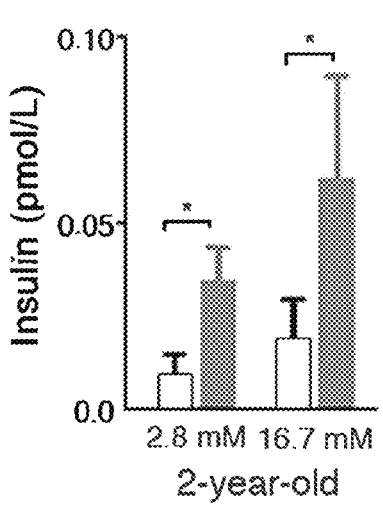
Figure 24E:
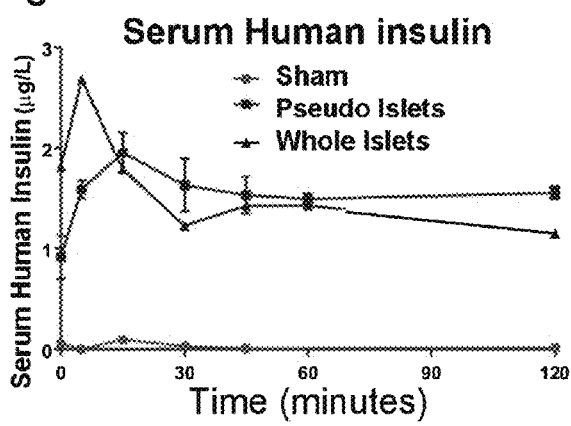
Figure 24F:
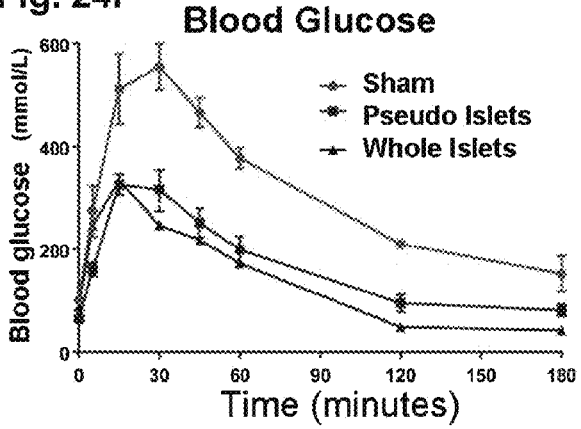

This system was used to mis-express factors like SIX3, a homeodomain transcription factor related to the *Drosophila* factor sine oculis. Remarkably, SIX3 expression in 2-year-old human pseudoislets enhanced basal and glucose-stimulated insulin secretion (FIG. 24C-D). After pseudoislet transplantation in immuno-compromised mice, insulin secretion after glucose challenge also remains regulated and robust, comparable to secretion from matched human islet controls (FIG. 24E). Consequently, glucose tolerance was improved similarly by transplanted control islets or pseudoislets compared to sham-transplanted controls (FIG. 24F).

NMU Suppression of Insulin Secretion is Eliminated by PTX

Figure 26:
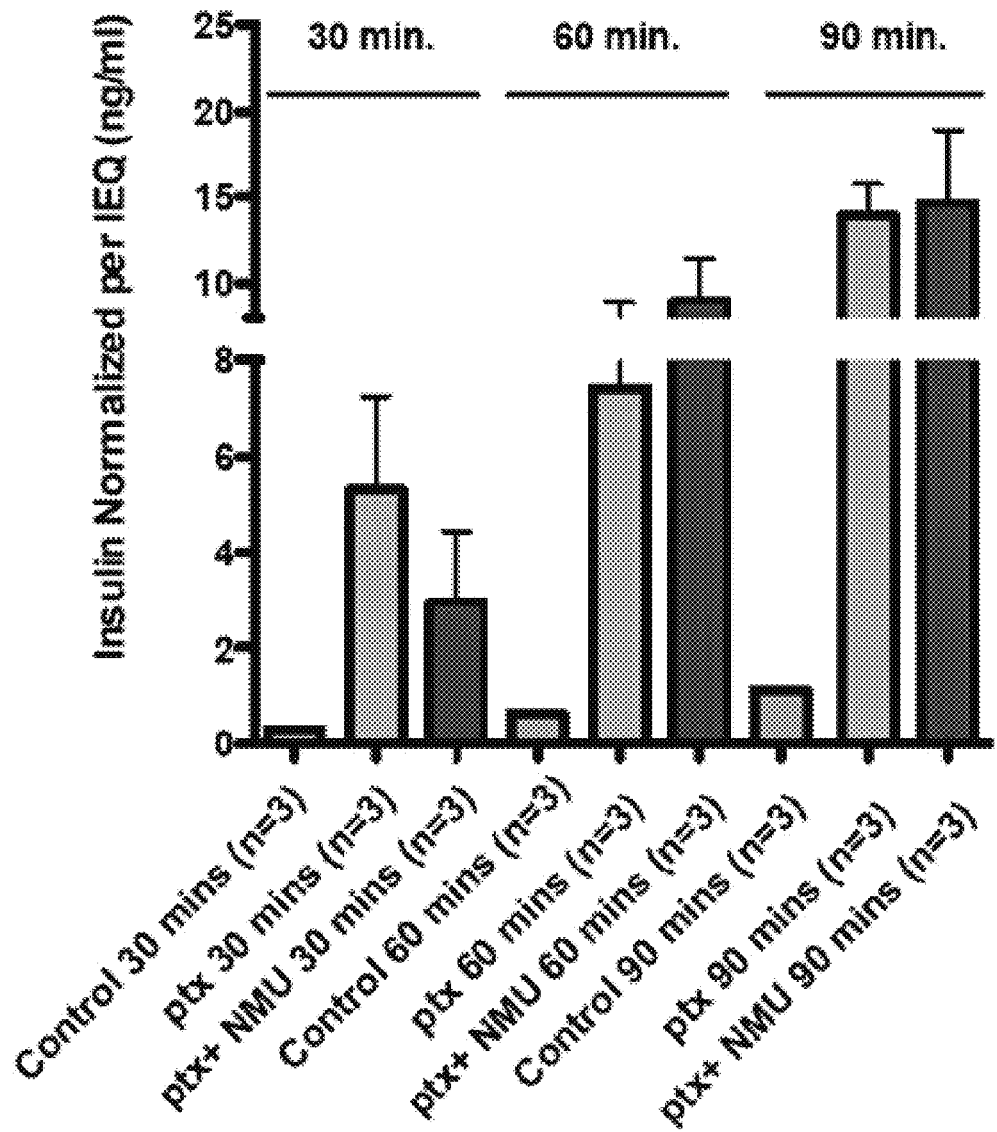
FIG. 26. Depicts data showing that NMU fails to suppress stimulation of insulin secretion by pertussis toxin.

Mouse islets exposed to pertussis toxin (PTX) had robust increases of insulin secretion, both at basal and increased glucose concentrations (FIG. 26), an effect thought to reflect PTX-induced degradation of the inhibitory G-protein $G_o2$. Importantly, PTX-treated mouse islets become insensitive to mouse Nmu mediated suppression of insulin secretion (FIG. 26). This supports the view that Nmu signaling requires $G_o2$ activity, FIG. 27: Batch assay with mouse islets.

Reconstituting Starvation Diabetes in Mice with Nmu Infusion

To identify effects of Nmu elevation on metabolism, glycemic and insulin regulation were studied in 10 week-old B6J mice with elevated serum Nmu after fasting. After intraperitoneal glucose tolerance testing (IPGTT) male or female mice fasted 72 hours (except for ad libitum water) had prolonged hyperglycemia compared to matched control mice with IPGTT after 24 hr. fasting (FIGS. 27A-B) and blunted serum insulin levels 5 minutes (0.16±0.1 vs 0.5±0.2 ng/ml, P<0.05: n=7 male mice) and 15 minutes after glucose challenge. Thus, starvation provoked hallmark features of 'starvation diabetes'. FIG. 28: Data for male mice shown.

Starvation provokes complex cellular and metabolic adaptations including multiple hormone responses. The doubling of circulating Nmu levels in starvation (FIG. 22A) suggested that Nmu might be sufficient to suppress insulin output in vivo. To test this possibility without the complexity of starvation responses, mice were injected intraperitoneally with NMU after 12 hour fasting and insulin and glucose responses were measured. Serum NM levels rose 5 minutes after intraperitoneal injection and remained two-fold greater than (basal) fasting levels at 60 minutes (FIG. 27C), recapitulating the degree of Nmu increase seen after 72 hr. fasting in mice. Oral glucose challenge after Nmu injection in wildtype mice resulted in marked hyperglycemia (FIG. 27D) accompanied by suppression of insulin levels. Thus, acute Nmu injection reconstituted hallmark features of starvation diabetes.

What is claimed is:

1. A protein that binds specifically to neuromedin U (NMU) and comprises an antigen binding region that comprises:
   (i) a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28, respectively; or
   (ii) a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12, respectively.

2. The protein of claim 1, wherein the antigen binding region comprises a light chain that comprises the amino acid sequence set forth in any one of SEQ ID NOs: 17 and 38, and a heavy chain that comprises the amino acid sequence set forth in any one of SEQ ID NOs: 25 and 39.

3. The protein of claim 1, wherein the protein is a single chain polypeptide.

4. The protein of claim 1, wherein the antigen binding region comprises a light chain that comprises the amino acid sequence set forth in any one of SEQ ID NOs: 1 and 36, and a heavy chain that comprises the amino acid sequence set forth in any one of SEQ ID NOs: 9 and 37.

5. The protein of claim 1, wherein the protein is an antibody.

6. The protein of claim 5, wherein the antibody is a mouse or human antibody.

7. The protein of claim 6, wherein the antibody is a humanized antibody.

8. A kit for detecting neuromedin U (NMU), comprising a first anti-NMU antibody and a second anti-NMU antibody, wherein the first and second anti-NMU antibodies bind to non-overlapping amino acids of NMU, and wherein one of the first and second anti-NMU antibody antibodies comprises:
   (a) a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28, respectively; or
   (b) a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12, respectively.

9. The kit of claim 8, wherein:
   (i) one of the first and second anti-NMU antibodies comprises a light chain comprising a CDR-L1, CDR-L2, and CDR-L3 comprising the amino acid sequences set forth in SEQ ID NOs: 18-20, respectively, and a heavy chain comprising a CDR-H1, CDR-H2, and CDR-H3 comprising the amino acid sequences set forth in SEQ ID NOs: 26-28, respectively; and
   (ii) the other of the first and second anti-NMU antibodies comprises a light chain comprising a CDR-L1, CDR-L2, and CDR-L3 comprising the amino acid sequences set forth in SEQ ID NOs: 2-4, respectively, and a heavy chain comprising a CDR-H1, CDR-H2, and CDR-H3 comprising the amino acid sequences set forth in SEQ ID NOs: 10-12, respectively.

10. The kit of claim 8, wherein the first anti-NMU antibody is immobilized on a solid surface.

11. The kit of claim 10, wherein the solid surface is a bead or a surface of a well of a multi-well plate.

12. The kit of claim 8, wherein at least one of the first and second anti-NMU antibodies detectably labeled.

13. The kit of claim 8, wherein at least one of the first and second anti-NMU antibodies is conjugated to a fluorophore, a fluorescent protein, or an enzyme that is indirectly detectable.

14. A protein that binds specifically to neuromedin U (NMU) and comprises an antigen binding region that comprises:
  (i) a first CDR comprising the amino acid sequence set forth in SEQ ID NO: 18, a second CDR comprising the amino acid sequence set forth in SEQ ID NO: 19, a third CDR comprising the amino acid sequence set forth in SEQ ID NO: 20, a fourth CDR comprising the amino acid sequence set forth in SEQ ID NO: 26, a fifth CDR comprising the amino acid sequence set forth in SEQ ID NO: 27, and a sixth CDR comprising the amino acid sequence set forth in SEQ ID NO: 28; or
  (ii) a first CDR comprising the amino acid sequence set forth in SEQ ID NO: 2, a second CDR comprising the amino acid sequence set forth in SEQ ID NO: 3, a third CDR comprising the amino acid sequence set forth in SEQ ID NO: 4, a fourth CDR comprising the amino acid sequence set forth in SEQ ID NO: 10, a fifth CDR comprising the amino acid sequence set forth in SEQ ID NO: 11, and a sixth CDR comprising the amino acid sequence set forth in SEQ ID NO: 12.

15. The protein of claim 14, wherein the protein is a humanized antibody.

* * * * *